(12) United States Patent
Vermaas

(10) Patent No.: US 8,753,840 B2
(45) Date of Patent: Jun. 17, 2014

(54) MODIFIED CYANOBACTERIA

(75) Inventor: Willem F. J. Vermaas, Tempe, AZ (US)

(73) Assignee: Arizona Board of Regents on behalf of Arizona State University, Scottsdale, AZ (US)

(*) Notice: Subject to any disclaimer, the term of this patent is extended or adjusted under 35 U.S.C. 154(b) by 1015 days.

(21) Appl. No.: 12/446,441

(22) PCT Filed: Oct. 19, 2007

(86) PCT No.: PCT/US2007/082000
§ 371 (c)(1),
(2), (4) Date: Oct. 29, 2010

(87) PCT Pub. No.: WO2008/130437
PCT Pub. Date: Oct. 30, 2008

(65) Prior Publication Data
US 2011/0053216 A1    Mar. 3, 2011

Related U.S. Application Data

(60) Provisional application No. 60/853,285, filed on Oct. 20, 2006.

(51) Int. Cl.
C12P 21/06 (2006.01)
C12N 5/04 (2006.01)
C12N 1/20 (2006.01)

(52) U.S. Cl.
USPC .............. 435/69.1; 435/419; 435/252.3

(58) Field of Classification Search
None
See application file for complete search history.

(56) References Cited

U.S. PATENT DOCUMENTS

| | | | |
|---|---|---|---|
| 4,242,455 A | 12/1980 | Muller et al. | 435/162 |
| 4,350,765 A | 9/1982 | Chibata et al. | 435/161 |
| 4,413,058 A | 11/1983 | Arcuri et al. | 435/161 |
| 4,458,066 A | 7/1984 | Caruthers et al. | 536/27 |
| 4,683,202 A | 7/1987 | Mullis | 435/91 |
| 5,220,007 A | 6/1993 | Pederson et al. | 536/231 |
| 5,221,605 A | 6/1993 | Bard et al. | 435/4 |
| 5,238,808 A | 8/1993 | Bard et al. | 435/4 |
| 5,284,760 A | 2/1994 | Feinstone et al. | 435/172.3 |
| 5,322,783 A | 6/1994 | Tomes et al. | 435/172.1 |
| 5,354,670 A | 10/1994 | Nickoloff et al. | 435/91.53 |
| 5,366,878 A | 11/1994 | Pederson et al. | 435/91.3 |
| 5,380,721 A | 1/1995 | Johnson et al. | 514/183 |

(Continued)

FOREIGN PATENT DOCUMENTS

WO   WO88/09379 A2   1/1988
WO   WO94/09699 A1   11/1994

(Continued)

OTHER PUBLICATIONS

Guo et al., Protein tolerance to random amino acid change, 2004, Proc. Natl. Acad. Sci. USA 101: 9205-9210.*

(Continued)

*Primary Examiner* — Alexander Kim
(74) *Attorney, Agent, or Firm* — Fulbright & Jaworski LLP

(57) ABSTRACT

Disclosed is a modified photoautotrophic bacterium comprising genes of interest that are modified in terms of their expression and/or coding region sequence, wherein modification of the genes of interest increases production of a desired product in the bacterium relative to the amount of the desired product production in a photoautotrophic bacterium that is not modified with respect to the genes of interest.

6 Claims, 13 Drawing Sheets

(56) References Cited

U.S. PATENT DOCUMENTS

| | | | |
|---|---|---|---|
| 5,384,253 A | 1/1995 | Krzyzek et al. | 435/172.3 |
| 5,389,514 A | 2/1995 | Taylor | 435/6 |
| 5,538,877 A | 7/1996 | Lundquist et al. | 435/172.3 |
| 5,538,880 A | 7/1996 | Lundquist et al. | 435/172.3 |
| 5,550,318 A | 8/1996 | Adams et al. | 800/205 |
| 5,563,055 A | 10/1996 | Townsend et al. | 435/172.3 |
| 5,580,859 A | 12/1996 | Felgner et al. | 514/44 |
| 5,589,466 A | 12/1996 | Felgner et al. | 514/44 |
| 5,610,042 A | 3/1997 | Chang et al. | 435/172.3 |
| 5,635,377 A | 6/1997 | Pederson et al. | 435/91.3 |
| 5,656,610 A | 8/1997 | Shuler et al. | 514/44 |
| 5,702,932 A | 12/1997 | Hoy et al. | 435/172.3 |
| 5,736,524 A | 4/1998 | Content et al. | 514/44 |
| 5,780,448 A | 7/1998 | Davis | 514/44 |
| 5,789,166 A | 8/1998 | Bauer et al. | 435/6 |
| 5,789,208 A | 8/1998 | Sharon | 435/91.41 |
| 5,789,215 A | 8/1998 | Berns et al. | 435/172.3 |
| 5,830,650 A | 11/1998 | Crea | 435/6 |
| 5,945,100 A | 8/1999 | Fick | 424/93.21 |
| 5,981,274 A | 11/1999 | Tyrrell et al. | 435/320.1 |
| 5,994,624 A | 11/1999 | Trolinder et al. | 800/278 |
| 6,667,171 B2 | 12/2003 | Bayless et al. | 435/292.1 |
| 6,699,696 B2 | 3/2004 | Woods et al. | 435/161 |
| 7,033,806 B2 | 4/2006 | Lagarias et al. | 435/191 |
| 7,385,123 B2 | 6/2008 | Sauer et al. | 435/254.3 |
| 2005/0108790 A1 | 5/2005 | Kaplan et al. | 800/920 |
| 2006/0019352 A1 | 1/2006 | Blanche et al. | 435/86 |
| 2006/0078973 A1 | 4/2006 | Renz et al. | 800/281 |

FOREIGN PATENT DOCUMENTS

| | | | |
|---|---|---|---|
| WO | WO95/06128 A2 | 2/1995 | |
| WO | WO 96/32484 | 10/1996 | |
| WO | WO 00/78782 | 12/2000 | |
| WO | WO/03/074715 | * 9/2003 | C12N 15/82 |
| WO | WO 2004/007727 | 1/2004 | |

OTHER PUBLICATIONS

Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from *Escherichia coli*, 1998, Biochem. Biophys. Res. Comm. 244:573-577.*
Wacey et al., Disentangling the perturbational effects of amino acid substitutions in the DNA-binding domain of p53., Hum Genet, 1999, vol. 104, pp. 15-22.*
Kaneko et al., Sequence analysis of the genome of the unicellular cyanobacterium *Synechocystis* sp. strain PCC6803. I. Sequence features in the 1 Mb region from map positions 64% to 92% of the genome., DNA Res., (1995), vol. 31, pp. 191-198.*
Lopez-Rodas et al., Adaptation of cyanobacteria and microalgae to extreme environmental changes derived from anthropogenic pollution., Limnetica, (2006), vol. 25, pp. 403-410.*
Reddy et al., Polyhydroxyalkanoates: an overview., Bioresource Technology (2003), vol. 87, pp. 137-146.*
Thelwell et al., An SmtB-like repressor from *Synechocystis* PCC 6803 regulates a zinc exporter, PNAS (Sep. 1, 1998), vol. 95 No. 18, pp. 10728-10733.*
*Synechocystis* sp. PCC6803 (last modified May 5, 2003).*
Davis et al., Overproduction of Acetyl-CoA Carboxylase Activity Increases the Rate of Fatty Acid Biosynthesis in *Escherichia coli*., The Journal of Biological Chemistry, (2000), vol. 275, pp. 28593-28598.*
Chauvat et al., A host-vector system for gene cloning in the cyanobacterium *Synechocystis* PCC 6803 Molecular and General Genetics MGG, vol. 204, No. 1 (1986), pp. 185-191.*
Frigaard et al., Photosynthesis Research Protocols, Methods in Molecular Biology, 2004, vol. 274, 325-340.*
Zang et al., Optimum Conditions for Transfromation of *Synechocystis* sp. PCC6803., The Journal of Micorbiology, Jun. 2007, vol. 45, pp. 241-245.* accA_SYNY (1999).*
accB_SYNY (1999).*
accC_SYNY (1999).*
accD_SYNY (1997).*
Westphal et al., Vipp1 deletion mutant of *Synechocystis*: A connection between bacterial phage shock and thylakoid biogenesis?, PNAS (Mar. 27, 2001), vol. 98 No. 7, pp. 4243-4248.*
Kroll et al., VIPP1, a nuclear gene of *Arabidopsis thaliana* essential for thylakoid membrane formation., PNAS (2001), vol. 98, pp. 4238-4242.*
Office Communication, issued in Chinese Patent Application No. 200780046148, dated Mar. 14, 2011. (English translation).
Office Communication, issued in Israeli Patent Application No. 198205, dated May 24, 2011. (English translation).
Kang et al., "Effects of co-expression of two higher plants genes ALD and TPI in *Anabaena* sp. PCC7120 on photosynthetic $CO_2$ fixation," *Enzyme and Microbiol. Technology*, 36: 600-604, 2005.
Ma et al., "Exogenous expression of the wheat chloroplastic fructose-1,6-bisphosphatase gene enhances photosynthesis in the transgenic cynaobacterium, *Anabaena* PCC7120," *Journal of Applied Phycology*, 17: 273-280, 2005.
Omata et al., "Identification of an ATP-binding cassette transporter involved in bicarbonate uptake in the cynaobacterium *Synechococcus* sp. strain PCC 7942," *PNAS*, 96 (23): 13571-13576, 1999.
Supplementary European Search Report, issued in Int. App. No. EP 07874515, mailed Oct. 28, 2009.
Disch et al., "Distribution of the mevaolonate and gylceraldehyde phosphate/pyruvate pathways for isoprenoid biosynthesis in unicellular algae and the cyanobacterium *Synechocystis* PCC 6714," *Biochemical Journal*, 333(1):381-388, 1998.
Lindberg et al., "Engineering a platform for photosynthetic isoprene production in cynabacteria, using *Synechocystis* as the model organism," *Metabolic Engineering*, 12(1):70-79, 2010.
Ma et al., "Exogenous expression of the wheat chloroplastic fructose-1,6-bisphosphatase gene enhances photosynthesis in the transgenic cyanobacterium, *Anabaena* PCC7120,"*Journal of Applied Phycology*, 17(3):273-280, 2005.
McKay et al., "Emissions of hydrocarbons from marine phytoplankton: Some results from controlled laboratory experiments," *Atmospheric Environment*, 30(14):2583-2593, 1996.
Miller et al., "First isolation of an isoprene synthase gene from poplar and successful expression of the gene in *Escherichia coli*," *Planta*, 213(3):483-487, 2001.
Omata et al., "Identification of an ATP-binding cassette transporter involved in bicarbonate uptake in the cyanobacterium *Synechococcus* sp. Strain PCC 7942," *Proceedings of the National Academy of Sciences of USA*, 96(23):13571-13576, 1999.
Partial European Search Report issued in European application No. 12156403.3, dated May 11, 2012.
Poliquin et al., "Inactiviation of sl11556 in *Synechocystis* strain PCC 6803 impairs isoprenoid biosynthesis from pentose phosphate cycle substrates in vitro," *Journal of Bacteriology*, 186(14):4685-4693, 2004.
Sasaki et al., "Gene expression and characterization of isoprene synthase from *Populus alba*," *FEBS Letters*, 579(11):2514-2518, 2005.
Aichi et al., "Role of NtcB in Activation of Nitrate Assimilation Genes in the Cyanobacterium *Synechocystis* sp. Strain PCC 6803," *J. Bacteriol.*, 183:5840-5847, 2001.
Allen, "Cyanobacterial cell inclusions," *Ann. Rev. Microbiol.*, 38:1-25, 1984.
Amichay et al., "Restoration of the wild-type locus in an RuBP carboxylase/oxygenase mutant of *Synechocystis* PCC 6803 via targeted gene recombination,"Mol. Gen. Genetics, 235:247-252, 1992.
Anderson and Dawes, "Occurrence, Metabolism, Metabolic Role, and Industrial Uses of Bacterial Polyhydroxyalkanoates," *Microbiol. Rev.*, 54:450-472, 1990.
Aresta et al., "Production of biodiesel from macroalgae by supercritical CO2 extraction and thermochemical liquefaction," *Environ. Chem. Ltrs.*, 3(3):136-139, 2005.
Asada et al., "Photosynthetic accumulation of poly-(hydroxybutyrate) by cyanobacteria—the metabolism and potential for CO2 recycling," Int J. Biol Macromol., 25:37-42, 1999.

(56) References Cited

OTHER PUBLICATIONS

Asato and Ginoza, "Separation of small circular DNA molecules from the blue-green alga *Anacystis nidulans*," Nat. New Biol., 244(135):132-133, 1973.
Ausubel et al. (eds.), Current Protocols in Molecular Biology, John Wiley & Sons, Inc., NY, 2001.
Ballard et al., In: Recent Advances in Mechanistic and Synthetic Aspects of Polymerization, Fontanille and Guyot (Eds.), 215:293-314. Reidel (Kluwer) Publishing Co., Lancaster, U.K., 1987.
Barringer et al., "Blunt-end and single-strand ligations by *Escherichia coli* ligase: influence on an in vitro amplification scheme," Gene, 89:117, 1990.
Beaucage et al., "Deoxynucleoside phosphoramidites—a new class of key intermediates for deoxypolynucleotide synthesis," Tetra. Lett., 22:1859-1862, 1981.
Bergmeyer, "New values for molar extinction coefficients of NADH and NADPH for use in routine laboratories," Klin. Chem. Klin. Biochem., 13:507-508, 1975.
Billi et al., "Gene Transfer to the Dessication-Tolerant Cyanobacterium *Chroococcidiopsis*," J. Bacteriol., 183(7):2298-2305, 2001.
Blackburn et al., "Apolipoprotein A-I decreases neutrophil degranulation and superoxide production," J. Lipid Res., 32(12):1911-1918, 1991.
Boocock et al., "Fast Formation of High-Purity Methyl Esters from Vegetable Oils," J. Am. Oil Chemists Soc. 75:1167-1172, 1998.
Boothman et al., "Identification and Characterization of X-Ray-induced Proteins in Human Cells," Cancer Res., 49(11):2871-2878, 1989.
Borek, "Oncogenes and Cellular Controls in Radiogenic Transformation of Rodent and Human Cells," Carcinog. Compr. Surv., 10:303-316, 1985.
Bowtell and Sambrook, DNA microarrays: a molecular cloning manual, Cold Spring Harbor Laboratory Press, Cold Spring Harbor, NY, 19898.
Brock, Biotechnology: A Textbook of Industrial Microbiology, Second Edition (1989) Sinauer Associates, Inc., Sunderland, Mass.
Brown et al., "Chemical Synthesis and Cloning of a Tyrosine tRNA Gene," Meth. Enzymol., 68:109-151, 1979.
Bryant et al., "Normalisation of sister chromatid exchange frequencies in Bloom's syndrome by euploid cell hybridisation," Nature, 279(5716):795-796, 1979.
Burks et al., "In vitro scanning saturation mutagenesis of an antibody binding pocket," Proc. Natl. Acad. Sci. USA, 94(2):412-417, 1997.
Burton and Barbas, "Human Antibodies from Combinatorial Libraries," Adv. Immunol., 57:191-280, 1994.
Cadwell and Joyce, "Randomization of Genes by PCR Mutagenesis," PCR Methods Appl., 2(1):28-33, 1992.
Campbell et al., "Accumulation of Poly-3-Hydroxybutyrate in *Spirulina platensis*," J. Bacteriol., 149:361-363, 1982.
Carbonelli et al., "A plasmid vector for isolation of strong promoters in *Escherichia coli*," FEMS Microbiol. Lett., 177(1):75-82, 1999.
Carr, "The occurrence of poly-p-hydroxybutyrate in the blue-green alga, *Chlorogloea fritschii*," Biochem. Biophys. Acta, 120:308-310, 1966.
Chandler, "RNA splicing specificity determined by the coordinated action of RNA recognition motifs in SR proteins," Proc. Natl. Acad. Sci. USA, 94(8):3596-601, 1997.
Chen and Okayama, "High-Efficiency Transformation of Mammalian Cells by Plasmid DNA," Mol. Cell Biol., 7(8):2745-2752, 1987.
Cisneros et al., "Recovery in aqueous two-phase systems of lutein produced by the green microalga *Chlorella protothecoides*," J. Chrom. B-Anal. Tech. Biomed. Life Sci., 807(1):105-110, 2004.
Cocea, "Duplication of a region in the mulitple cloning site of a plasmid vector to enhance cloning-mediated addition of restriction sites to a DNA fragment," Biotechniques, 23(5):814-816, 1997.
Cooley and Vermaas, "Succinate dehydrogenase and other respiratory pathways in thylakoid membranes of *Synecheystis* sp. Strain PCC 6803: Capacity comparisons and physiological function," J. Bacteriol., 183:4251-4258, 2001.
Cooley et al., "Succinate:Quinol Oxidoreductases in the Cyanobacterium *Synechocystis* sp. Strain PCC 6803: Presence and Function in Metabolism and Electron Transport," J Bacteriol., 182:714-722, 2000.
Cooley et al., "Insertional Mutagenesis of the *Drosophila* Genome with Single P Elements," Science, 239(4844):1121-1128, 1988.
Cunningham and Wells, "High-Resolution Epitope Mapping of hGH-Receptor Interactions by Alanine-Scanning Mutagenesis," Science, 244(4908):1801-1085, 1989.
Dahlqvist et al., "Phospholipid:diacylglycerol acyltransferase: An enzyme that catalyzes the acyl-CoA-independent formation of triacylglycerol in yeast and plants," Proc. Natl. Acad. Sci. USA, 97(12):6487-92, 2000.
Dawes and Senior, "The role and regulation of energy reserve polymers in micro-organisms," Adv. Microb. Physiol., 10:135-266, 1973.
De Philippis, "Factors affecting poly-β-hydroxybutyrate accumulation in cyanobacteria and in purple non-sulfur bacteria," FEMS Microbiol Rev., 103:187-194, 1992.
De Philippis, "Glycogen and poly-β-hydroxybutyrate synthesis in *Spirulina maxima*," J. Gen. Microbiol, 138:1623-1628, 1992.
Despande, "Ethanol production from cellulose by coupled saccharification/fermentation using *Saccharomyces cerevisiae* and cellulase complex from *Sclerotium rolfsii* UV-8 mutant,"Appl. Biochem. Biotechnol., 36(3):227-34, 1992.
Deutscher (ed.), Guide to Protein Purification. Methods in Enzymology, vol. 182, Academic Press, Inc., NY, 1990.
Edwards and Gantt, "Phycobilisomes of the thermophilic blue-green alga *Synechococcus lividus*," J. Cell Biol., 50(3):896-900, 1971.
Fechheimer et al., "Transfection of mammalian cells with plasmid DNA by scrape loading and sonication loading," Proc. Natl. Acad. Sci. USA, 84:8463-8467, 1987.
Fraley et al., "Entrapment of a bacterial plasmid in phospholipid vesicles: Potential for gene transfer," Proc. Natl. Acad. Sci. USA, 76:3348-3352, 1979.
Gantt and Conti, "Ultrastructure of Blue-Green Algae," J. Bacteriol., 97(3):1486-1493, 1969.
Goeddel (ed.), Gene Expression Technology: Methods in Enzymology, 185, Academic Press, San Diego, Calif., 1990.
Gopal, "Gene Transfer Method for Transient Gene Expression, Stable Transformation, and Cotransformation of Suspension Cell Cultures," Mol. Cell Biol., 5:1188-1190, 1985.
Graham and Van Der Eb, "A New Technique for the Assay of Infectivity of Human Adenovirus 5 DNA," Virology, 52:456-467, 1973.
Grigorieva and Shestakov, "Transformation in the cyanobacterium *Synechocystis* sp. 6803," FEMS Microbiol. Lett., 13:367-370, 1982.
Guatelli et al., "Isothermal, in vitro amplification of nucleic acids by a multienzyme reaction modeled after retroviral replication," Proc. Natl. Acad. Sci. USA, 87:1874, 1990.
Hall et al., "Radiation Response Characteristics of Human Cells in Vitro," Radial. Res., 1 14(3):415-424 1988.
Harland and Weintraub, "Translation of Is Specifically mRNA Injected into *Xenopus* Inhibited by Antisense RNA Oocytes," J. Cell Biol., 101(3):1094-1099, 1985.
He et al., "Expression of a higher plant light-harvesting chlorophyll a/b-binding protein in *Synechocystis* sp. PCC 6803," Europ. J. Biochem., 263(2):561-570, 1999.
Hein et al., "*Synechocystis* sp. PCC6803 possesses a two-component polyhydroxyalkanoic acid synthase similar to that of anoxygenic purple sulfur bacteria," Arch. Microbiol, 170:162-170, 1998.
Herrero et al., "Regulation of Nitrate Reductase Levels in the Cyanobacteria *Anacystis nidulans*, *Anabaena* sp. Strain 7119, and *Nostoc* sp. Strain 6719," J. Bacteriol., 145:175-180, 1981.
Hilton et al., "Saturation Mutagenesis of the WSXWS Motif of the Erythropoietin Receptor," J. Biol. Chem., 271(9):4699-4708, 1996.
Howitt and Vermaas, "Quinol and Cytochrome Oxidases in the Cyanobacterium *Synechocystis* sp. PCC 6803," Biochemistry, 37:17944-17951, 1998.
Howitt et al., "Type 2 NADH Dehydrogenases in the Cyanobacterium *Synechocystis* sp. Strain PCC 6803 Are Involved in Regulation Rather Than Respiration," J. Bacteriol., 181:3994-4003, 1999.
Howitt et al., "A Strain of *Synechocystis* sp. PCC 6803 without photosynthetic oxygen evolution and respiratory oxygen consump-

(56) References Cited

OTHER PUBLICATIONS tion: implications for the study of cyclic photosynthetic electron transport," Planta, 214:46-56, 2001.
Innis et al., PCR Protocols. A Guide to Methods and Application, Academic Press, Inc., San Diego, 1990.
International Search Report and Written Opinion issued in International Application No. PCT/US2007/82000, mailed Mar. 3, 2009.
Inouye and Inouye, "Up-promoter mutations in the Ipp gene of *Escherichia coli*," Nucleic Acids Res., 13:3101-3109, 1985.
Jensen and Sicko, "Fine Structure of Poly-3-Hydroxybutyric Acid Granules in a Blue-Green Alga, *Chlorogloea fritschii*," J. Bacteriol., 181:3994-4003, 1999.
Jordan and Ogren, "Species variation in the specificity of ribulose biphosphate carboxylase/oxygenase," Nature, 291:513-515, 1981.
Kaneda et al., "Increased Expression of DNA Cointroduced with Nuclear Protein in Adult Rat Liver," Science, 243:375-378, 1989.
Kaneko et al., "Sequence Analysis of the Genome of the Unicellular Cyanobacterium *Synechocystis* sp. Strain PCC6803. II. Sequence Determination of the Entire Genome and Assignment of Potential Protein-coding Regions," DNA Res. 3(3):109-136, 1996.
Kato et al., "Expression of Hepatitis B Virus Surface Antigen in Adult Rat Liver," J. Biol. Chem., 266:3361-3364, 1991.
Klaidman et al., "High-Performance Liquid Chromatography Analysis of Oxidized and Reduced Pyridine Dinucleotides in Specifc Brain Regions," Anal. Biochem., 228:312-317, 1995.
Koksharova et al., "Genetic and biochemical evidence for distinct key functions of two highly divergent GAPDH genes in catabolic and anabolic carbon flow of the cyanobacterium *Synechocystis* sp. PCC 6803," Plant Mol. Biol., 36:183-194, 1998.
Koncz et al., "Isolation of a gene encoding a novel chloroplast protein by T-DNA tagging in *Arabidopsis thaliana*," EMBO J., 9(5):1337-1346, 1990.
Kwoh et al., "Transcription-based amplification system and detection of amplified human immunodeficiency virus type 1 with a bead-based sandwich hybridization format," Proc. Natl. Acad. Sci. USA, 86:1173, 1989.
Lagarde et al., "Increased Production of Zeaxanthin and Other Pigments by Application of Genetic Engineering Techniques to *Synechocystis* sp. Strain PCC 6803," Appl. Environ. Microb., 66(1):64-72, 2000.
Lama et al., "Effect of growth conditions on endo-and exopolymer biosynthesis in *Anabaena cylindrica* 10 C," Phytochemistry, 42:655-659, 1996.
Lambert and Borek, "X-ray-Induced Changes in Gene Expression in Normal and Oncogene-Transformed Rat Cell Lines," J. Natl. Cancer Inst., 80(18):1492-1497, 1988.
Landegren et al., "A Ligase-Mediated Gene Detection Technique," Science, 241:1077-1080, 1988.
Lemoigne, "Produits de deshydration et de polymerization de l'acide β-oxybutyrique," Bull. Soc. Chim. Biol., 8:770-782, 1926. (English abstrat).
Levenson et al., "Internal Ribosomal Entry Site-Containing Retroviral Vectors with Green Fluorescent Protein and Drug Resistance Markers," Hum. Gene Ther., 9(8):1233-1236, 1998.
Li and Golden, "Enhancer activity of light-responsive regulatory elements in the untranslated leader regions of cyanobacterial psbA genes," Proc. Natl. Acad. Sci. USA, 90:11673-11682, 1993.
Liebergesell et al., "Purification and characterization of the poly(hydroxyalkanoic acid) synthase from *Chromatium vinosum* and localization of the enzyme at the surface of the poly(hydroxyalkanoic acid) granule," Eur. J. Biochem., 226:71-80, 1994.
Lomell et al., "Quantitiative Assays Based on the Use of Replicatable Hybridization Probes," J. Clin. Chem., 35:1826, 1989.
Manchak and Page, "Control of polyhydroxyalkanoate synthesis in *Azotobacter vinelandii* strain UWD," Microbiol., 140:953-963, 1994.
Marks et al., "Bypassing Immunization: Human antibodies from V-gene Libraries Displayed on Phage," J. Mol. Biol., 222:581-597, 1991.

Marland et al., In: Global, Regional, and National $CO_2$ Fossil-Fuels Emissions. In Trends: A Compendium of Data on Global Change, 2006. (http://cdiac.esd.ornl.gov/trends/emis/overview.html).
McCann et al., "Detection of Carcinogens as Mutagens: Bacterial Tester Strains with R Factor Plasmids," Proc. Natl. Acad. Sci. USA, 72(3):979-983, 1975.
McCool and Cannon, "Polyhydroxyalkanoate Inclusion Body-Associated Proteins and Coding Region in *Bacillus megaterium*," J. Bacteriol., 181:585-592, 1999.
McGinn et al., "Inorganic Carbon Limitation and Light Control the Expression of Transcripts Related to the CO2-Concentrating Mechanism in the Cyanobacterium *Synechocystis* sp. Strain PCC6803," Plant Physiology, 132(1):218-229, 2003.
Merida et al., "Regulation of Glutamine Synthetase Activity in the Unicellular Cyanobacterium *Synechocystis* sp. Strain PCC 6803 by the Nitrogen Source: Effect of Ammonium," J. Bacteriol., 173:4095-4100, 1991.
Miyake et al., "Polyhydroxybutyrate Production from Cardon Dioxide by Cyanobacteria," Appl. Biochem. Biotech., 84:991-1002, 2000.
Miyake et al., "A Thermophilic Cyanobacterium, *Synechococcus* sp. MA19, Capable of Accumulating Poly-,&Hydroxybutyrate," J. Ferment. Bioeng., 82:516-518, 1996.
Mohamed et al., "Myxoxanthophyll Is Required for Normal Cell Wall Structure and Thylakoid Organization in the Cyanobacterium *Synechocystis* sp. Strain PCC 6803," J. Bacteriol., 187:6883-6892, 2005.
Nabel et al., "Recombinant Gene Expression in vivo within Endothelial Cells of the Arterial Wall," Science, 244(4910):1342-1344, 1989.
Nakamura et al., "Complete Genome Structure of the Thermophilic Cyanobacterium *Thermosynechococcus elongatus* BP-1," DNA Res., 9(4):123-130, 2002.
Nandi and Sengupta, "Microbial production of hydrogen: an overview," Crit. Rev. Microbiology, 24(1):61-84, 1998.
Narang et al., "Improved phosphotriester method for the synthesis of gene fragments," Meth. Enzymol., 68:90-99, 1979.
Nicolau and Sene, "Liposome-mediated DNA transfer in eukaryotic cells: Dependence of the transfer efficiency upon the type of liposomes used and the host cell cycle stage," Biochim. Biophys. Acta, 721:185-190, 1982.
Nicolau et al., "Liposomes as Carriers for in vivo gene transfer and expression," Methods Enzymol., 149:157-176, 1987.
Nobre et al., "Supercritical carbon dioxide extraction of astaxanthin and other carotenoids from the microalga *Haematococcus pluvialis*," Europ. Food Res. Technology, 223(6):787-790, 2006.
Oelkers et al., "A Lecithin Cholesterol Acyltransferase-like Gene Mediates Diacylglycerol Esterification in Yeast," J. Biol. Chem., 275:15609-12, 2000.
Ogawa, "A gene homologous to the subunit-2 gene of NADH dehydrogenase is essential to inorganic carbon transport of *Synechocystis* PCC6803," Proc. Natl. Acad. Sci. USA, 88:4275-4279, 1991.
Oppenheimer et al., "A myb gene required for leaf trichrome differentiation in *Arabidopsis* is expressed in stipules," Cell, 67(3):483-493, 1991.
Ostle and Holt, "Nile Blue a as a Fluorescent Stain for Poly-3-Hydroxybutyrate," Appl. Environ. Microbiol., 44:238-241, 1982.
Potter et al., "Enhancer-dependent expression of human Kc immunoglobulin genes introduced into mouse pre-B lymphocytes by electroporation," *Proc. Natl. Acad. Sci. USA*, 81:7161-7165, 1984.
Prince et al., "The Photobiological Production of Hydrogen: Potential Efficiency and Effectiveness as a Renewable Fuel," Crit. Rev. Microbiology, 31(1):19-31, 2005.
Reusch, "Low molecular weight complexed poly(3-hydroxybutyrate): a dynamic and versatile molecule in vivo," Can. J. Microbiol., 41:50-54, 1995.
Rippka et al., "Generic assignments, strin histories and properties of pure cultures of Cyanobacteria," J. Gen. Micro., 111:1-61, 1979.
Rippe et al., "DNA-Mediated Gene Transfer into Adult Rat Hepatocytes in Primary Culture," Mol. Cell Biol., 10:689-695, 1990.
Ris and Singh, "Electron Microscope Studies on Blue-Green Algae," J. Biophys. Biochem. Cytol., 9:63-80, 1961.

(56) References Cited

OTHER PUBLICATIONS

Rito-Palomares, "Practical application of aqueous two-phase partition to process development for the recovery of biological products," J. Chrom. B-Anal. Tech. Biomed. Life Sci., 807(1):3-11, 2004.
Robert, "Amplification of nucleic acid sequences.: The choices multiply," Journal of NIH Research, 3(2):81-94, 1991.
Roberts and Koths, "The blue-green alga agmenellum quadruplicatum contains covalently closed DNA circles," Cell, 9(4):551-557, 1976.
Rubio et al., "A cyanobacterial narB gene encodes a ferredoxin-dependent nitrate reductase," Plant Mol. Biol., 30:845-850, 1996.
Saka et al., "Non-catalytic biodiesel fuel production with supercritical methanol technologies," J. Scient. Indust. Res., 65(5):420-425, 2006.
Sambrook et al., Molecular Cloning, A Laboratory Manual. Cold Spring Harbor Press, Cold Spring Harbor, NY, 1989.
Schmidt et al., "Transposon Tagging and Molecular Analysis of the Maize Regulatory Locus opaque-2," Science, 238(4829):960-963, 1987.
Scopes, Protein Purification: Principles and practice, Springer-Verlag, NY; 1982.
Serrano-Carreon et al., "Production and biotransformation of 6-pentyl-α-pyrone by *Trichoderma harzianum* in two-phase culture systems," Appl. Microb. Biotech., 58(2):170-174, 2002.
Shi et al., "Effect of Modifying Metabolic Network on Poly-3-Hydroxybutyrate Biosynthesis in Recombinant *Escherichia coli*," J. Biosci. Bioeng., 87:666-677, 1999.
Smith, "Modes of cyanobacterial carbon metabolism," Ann. Microbiol., 134B:93-113, 1983.
Sommer et al., "Deficiens, a homeotic gene involved in the control of flower morphogenesis in *Antirrhinum majus*: the protein shows homology to transcription factors," EMBO J., 9(3):605-613, 1990.
Stal, "Poly(hydroxyalkanoate) in cyanobacteria—an overview," FEMS Micro. Rev., 103:169-180, 1992.
Stanier and Cohen-Bazire, "Phototrophic prokaryotes: the cyanobacteria," Annu. Rev. Microbiol., 31:225-274, 1977.
Steinbüchel and Füchtenbusch, "Diversity of bacterial polyhydroxyalkanoic acids," Trends Biotechnol., 16:419-427, 1998.
Steinbüchel and Valentin, "Bacterial and other biological systems for polyester production," FEMS Microbiol. Lett., 128:219-228, 1995.
Steinbüchel, "Polyhydroxyalknoic acids," in: Biomaterials: Novel materials from biological sources, Byrom (Ed), Macmillan, London, 123-213, 1991.
Sudesh, "Effect of increased PHA synthase activity on polyhydroxyalkanoates biosynthesis in *Synechocystis* sp. PCC6803," Int. J. Biol. Macromol., 30:97-104, 2002.
Takahashi et al., "Improved accumulation of poly-3-hydroxybutyrate by a recombinant cyanobacterium," Biotech. Lett., 20:183-186, 1998.
Taroncher-Oldenberg et al., "Identification and Analysis of the Polyhydroxyalkanoate-Specific β-Ketothiolase and Acetoacetyl Coenzyme A Reductase Genes in the Cyanobacterium *Synechocystis* sp. Strain PCC6803," Appl. Environ. Microbiol., 66:4440-4448, 2000.
Tasaka et al., "Targeted mutagenesis of acyl-lipid desaturases in *Synechocystis*: evidence for the important roles of polyunsaturated membrane lipids in growth, respiration and photosynthesis," EMBO J., 15(23):6416-6425, 1996.
Topal et al., "Extraction of Lycopene from Tomato Skin with Supercritical Carbon Dioxide: Effect of Operating Conditions and Solubility Analysis," J. Agric. Food Chem., 54(15):5604-5610, 2006.
Tur-Kaspa et al., "Use of Electroporation to Introduce Biologically Active Foreign Genes into Primary Rat Hepatocytes," Mol. Cell Biol., 6:716-718, 1986.
Van Brunt, "Amplifying genes: PCR and its alternatives," Biotechnology, 8:291-294, 1990.

Van De Meene et al., "The three-dimensional structure of the cyanobacterium *Synechocystis* sp. PCC 6803," Arch. Microbiol., 184(5):259-270, 2006.
Vincenzini et al., "Occurrence of Poly-,3-Hydroxybutyrate in *Spirulina* Species," J. Bacteriol., 172:2791-2792, 1990.
Vinnemeier et al., "Transcriptional analysis of the isiAB operon in salt-stressed cells of the cyanobacterium *Synechocystis* sp. PCC 6803," FEMS Microb. Ltrs, 169(2):323-330, 1998.
Wältermann et al., "Mechanism of lipid-body formation in prokaryotes: how bacteria fatten up," Mol. Microbiol. 55(3):750-63, 2005.
Wältermann et al., "*Rhodococcus opacus* strain PD630 as a new source of high-value single-cell oil? Isolation and characterization of triacylglycerols and other storage lipids," Microbiol., 146:1143-9, 2000.
Warren et al., "A Rapid Screen of Active Site Mutants in Glycinamide Ribonucleotide Transformylase," Biochemistry, 35(27):8855-8862, 1996.
White, The Physiology and Biochemistry of Prokaryotes, Oxford University Press, Inc., New York, 2000.
Williams, "Construction of specific mutations in photosystem II photosynthetic reaction center by genetic engineering methods in *Synechocystis* 6803," Methods Enzymol., 167:766-768, 1988.
Wilson et al., "Implantation of Vascular Grafts Lined with Genetically Modified Endothelial Cells," Science, 244:1344-1346, 1989.
Witte et al., "Effects of Irradiation on the Release of Growth Factors from Cultured Bovine, Porcine, and Human Endothelial Cells," Cancer Res., 49(18):5066-5072, 1989.
Wong, "Appearance of β-lactamase activity in animal cells upon liposome-mediated gene transfer," Gene, 10:87-94, 1980.
Wu and Wallace, "Specificity of the nick-closing activity of bacteriophage T4 DNA ligase," Gene, 76(2):245-254, 1989.
Wu and Wu, "Evidence for Targeted Gene Delivery to Hep G2 Hepatoma Cells in Vitro," Biochemistry, 27:887-892, 1988.
Wu and Wu, "Receptor-mediated in Vitro Gene Transformation by a Soluble DNA Carrier System," J. Biol. Chem., 262:4429-4432, 1987.
Wu et al., "Accumulation of poly-b-hydroxybutyrate in cyanobacterium *Synechocystis* sp. PCC6803," Bioresour. Technol., 76:85-90, 2001.
Wu et al., "Modification of carbon partitioning to enhance PHB production in *Synechocystis* sp. PCC6803," Enzyme Microb. Technol., 76:85-90, 2001.
Yagi, "Procaryotic complex I (NDH-1), an overview," Biochim. Biophys. Acta., 1364:125-133, 1998.
Yelton et al., "Affinity Maturation of the BR96 Anti-Carcinoma Antibody by Codon-Based Mutagenesis," J. Immunol., 155(4):1994-2004, 1995.
Zeng et al., "ATP-Binding Site of Human Brain Hexokinase As Studied by Molecular Modeling and Site-Directed Mutagenesis," Biochemistry, 35(40):13157-13164, 1996.
Zhang et al., "Photoautotrophic Growth of the Cyanobacterium *Synechocystis* sp. PCC 6803 in the Absence of Cytochrome c553 and Plastocyanin," J. Biolog. Chem., 269(7):5036-5042, 1994.
Zhang et al., "A Method for Determination of Pyridine Nucleotides Using a Single Extract," Ann. Biochem., 285:163-167, 2000.
Zhou et al., "Fermentation of 10% (w/v) sugar to D(−)-lactate by engineered *Escherichia coli* B," Biotech. LTRS, 27(23-24):1891-1896, 2005.
Zou et al., "The *Arabidopsis thaliana* TAG1 mutant has a mutation in a diacylglycerol acyltransferase gene," Plant J., 19(6):645-53, 1999.
Office Communication, issued in European Patent Application No. 07874515.5, dated Nov. 29, 2011.
Bugler, et al., *Microbiol.*, 140(8):1937-1944, 1994.
Delisa, et al., *Journal of Bacteriol*, 186(2):366-373, 2004,.
Kroll, et al., *PNAS*, 98(7):4238-4242, 2001.
Vothknecht, et al., *Gene*, 354:99-109, 2005, Abstract only.
Partial International Search Report from European Patent Application No. 12156382.9-2405, issued Sep. 27, 2012.

\* cited by examiner

MODIFIED CYANOBACTERIA

GOVERNMENT SUPPORT CLAUSE INSERTION

This invention was made with government support under Grant No. DE-FG03-01ER15251 awarded by the US Department of Energy. The government has certain rights in the invention.

CROSS-REFERENCE TO RELATED APPLICATIONS

This application is a national phase application under 35 U.S.C. §371 of International Application No. PCT/US2007/082000 filed Oct. 19, 2007, which claims the benefit of U.S. Provisional Application No. 60/853,285 filed Oct. 20, 2006. The entire contents of these applications are incorporated by reference.

BACKGROUND OF THE INVENTION

A. Field of the Invention

The present invention relates generally to the field of bacteriology. In certain aspects, the present invention is directed to modified photoautotrophic bacteria with overexpressed, down-regulated, introduced, deleted or modified genes of interest to produce a desired product. The desired product can be processed into a biofuel, bioplastic, animal feed additive, nutraceutical, food additive, fertilizer, etc.

B. Background

Two challenges facing the world today include the ongoing pollution of the environment with carbon dioxide which contributes to global warming and the increasing consumption of the world's natural energy resources such as fossil fuels. A problematic cycle exists where the increase in fossil fuel consumption correlates with an increase in carbon dioxide air pollution.

For instance, it has been estimated that the United States produces 1.7 billion tons of carbon dioxide annually from the combustion of fossil fuels (see U.S. Publication No. 2002/0072109). This pales in comparison to the global production of carbon dioxide from fossil fuel consumption which is estimated to be between 7-8 billion tons/year (Marland et al. 2006). An increase in carbon dioxide air pollution can lead to an increase in global warming and in turn can increase the frequency and intensity of extreme weather events, such as floods, droughts, heat waves, hurricanes, tornadoes, etc. Other consequences of global warming can include changes in agricultural yields, species extinctions, and increases in the ranges of disease vectors.

Methods for carbon dioxide remediation have been suggested. For instance, U.S. Publication No. 2002/0072109 discloses an on-site biological sequestration system that can decrease the concentration of carbon-containing compounds in the emissions of fossil-fuel powered power generation units. The system uses photosynthetic microbes such as algae and cyanobacteria which are attached to a growth surface arranged in a containment chamber that is lit by solar photons. The cyanobacteria uptake and utilize the carbon dioxide produced by the fossil-fuel powered power generation units.

As for the second challenge, global energy demand continues to increase which places a higher demand on the non-renewable fossil fuel energy supplies. Alternative sources for energy have recently been developed. For instance, agricultural products such as corn, soybeans, flaxseed, rapeseed, sugar cane, and palm oil are currently being grown for use in biofuel production. Biodegradable by-products from industries such as the agriculture, housing, and forestry industries can also be used to produce bioenergy. For example, straw, timber, manure, rice, husks, sewage, biodegradable waste and food leftovers can be converted into biogas through anaerobic digestion. However, plant productivity has a low yield of conversion of solar energy to biomass and biofuels, due to limitations in $CO_2$ diffusion and sequestration, growing season, and solar energy collection over the course of the year. A higher efficiency of solar energy conversion is achieved by algae and cyanobacteria.

Methods for using living organisms to produce ethanol have also been described. For instance, U.S. Pat. No. 4,242,455 to Muller et al. describes a continuous process in which an aqueous slurry of carbohydrate polymer particles, such as starch granules and/or cellulose chips, fibers, etc., are acidified with a strong inorganic acid to form a fermentable sugar. The fermentable sugar is then fermented to ethanol with at least two strains of *Saccharomyces*. U.S. Pat. No. 4,350,765 to Chibata et al. describes a method of producing ethanol in a high concentration by using an immobilized *Saccharomyces* or *Zymomonas* and a nutrient culture broth containing a fermentative sugar. U.S. Pat. No. 4,413,058 to Arcuri et al. describes a strain of *Zymomonas mobilis* which is used to produce ethanol by placing the microorganism in a continuous reactor column and passing a stream of aqueous sugar through said column.

PCT Application WO/88/09379 to Hartley et al. describes the use of facultative anaerobic thermophilic bacterial strains which produce ethanol by fermenting a wide range of sugars, including cellobiose and pentoses. These bacterial strains contain a mutation in lactate dehydrogenase. As a result, these strains which would normally produce lactate under anaerobic conditions, produce ethanol instead.

U.S. Publication 2002/0042111 discloses a genetically modified cyanobacterium that can be used to produce ethanol. The cyanobacterium includes a construct comprising DNA fragments encoding pyruvate decarboxylase (pdc) and alcohol dehydrogenase (adh) enzymes obtained from the *Zymomonas mobilis* plasmid pLOI295.

SUMMARY OF THE INVENTION

The present invention overcomes the deficiencies in the art by providing photoautotrophic bacteria that have been modified to introduce, delete and/or alter the sequence or expression level of gene(s) of interest to increase the production of a desired product. The desired product can be processed into several useful products such as biofuels, bioplastics, animal feed additives, valuable pigments or anti-oxidants, or organic fertilizers.

One embodiment of the present invention relates to modified photoautotrophic bacterium comprising one or more genes of interest whose expression has been altered and/or whose gene product function has been changed resulting in an increase in production of one or more products selected from the group consisting of fatty acids, lipids carotenoids, other isoprenoids, carbohydrates, proteins, biogases, or combinations thereof, in the bacterium relative to the amount of the one or more products in a photoautotrophic bacterium in which expression of the one or more genes of interest is not altered. In another embodiment, multiple alterations are introduced into one or more genes, wherein the multiple alterations collectively increase the production of the desired product. The modified photoautotrophic bacterium can be of a type that uptakes and fixes carbon dioxide. In certain aspects, the modified photoautotrophic bacterium is further defined as having increased uptake and fixation of carbon dioxide relative to an amount of uptake and fixation of carbon dioxide by a photoautotrophic bacterium in which expression of and/or gene product function of the one or more genes of interest has not been altered.

The expression of a gene of interest may be altered to cause the gene to be upregulated or down-regulated. In another embodiment, the expression may be altered from alteration of an endogenous gene, the deletion of an endogenous gene or the modification of the control sequences of an endogenous gene. In yet another embodiment, the expression of a gene of interest may be altered by the addition of one or more transgenic sequences to one or more unmodified genes.

The term "native photoautotrophic bacterium" as used in the specification and in the claims refers to a photoautotrophic bacterium that is found in nature and does not have gene functions altered in the manner disclosed in the current invention. However, of course, it is possible to practice the current invention by obtaining a bacterium previously altered to increase the production of a desired product. These previous alterations may include any manipulations made to the bacterium.

The current photoautotrophic bacterium of the current invention may be originally altered bacterium or may be progeny of any generation, so long as the alteration that results in the increase in production of one or more desired products in the bacterium relative to the amount of the one or more products in a photoautotrophic bacterium in which expression of the one or more genes of interest is not altered is carried to the progeny.

Non-limiting examples of photoautotrophic bacteria that can be used in the context of the present invention include cyanobacteria, green sulfur bacteria, green non-sulfur bacteria, heliobacteria, photosynthetic acidobacteria, purple sulfur bacteria, or purple nonsulfur bacteria. In certain aspects, the modified photoautotrophic bacterium is a cyanobacterium. The cyanobacterium can be of the order Chroococcales, Nostocales, Oscillatoriales, Pleurocapsales, Prochlorophytes, or Stigonematales. The order Chroococcales can include the species selected from the group consisting of *Aphanocapsa, Aphanothece, Chamaesiphon, Chroococcus, Crocosphaera, Cyanobacterium, Cyanobium, Cyanothece, Dactylococcopsis, Gloeobacter, Gloeocapsa, Gloeothece, Euhalothece, Halothece, Johannesbaptistia, Merismopedia, Microcystis, Rhabdoderma, Synechococcus*, and *Synechocystis*, and *Thermosynechococcus*. The order Nostocales can include the species selected from the group consisting of *Coleodesmium, Fremyella, Microchaete, Rexia, Spirirestis, Tolypothrix, Anabaena, Anabaenopsis, Aphanizomenon, Aulosira, Cyanospira, Cylindrospermopsis, Cylindrospermum, Nodularia, Nostoc, Richelia, Calothrix, Gloeotrichia*, and *Scytonema*. The order Oscillatoriales can include the species selected from the group consisting of *Arthrospira, Geitlerinema, Halomicronema, Halospirulina, Katagnymene, Leptolyngbya, Limnothrix, Lyngbya, Microcoleus, Oscillatoria, Phormidium, Planktothricoides, Planktothrix, Plectonema, Limnothrix, Pseudanabaena, Schizothrix, Spirulina, Symploca, Trichodesmium*, and *Tychonema*. The order Pleurocapsales can include the species selected from the group consisting of *Chroococcidiopsis, Dermocarpa, Dermocarpella, Myxosarcina, Pleurocapsa, Stanieria*, and *Xenococcus*. The order Prochlorophytes can include the species selected from the group consisting of *Prochloron, Prochlorococcus*, and *Prochlorothrix*. The order Stigonematales can include the species selected from the group consisting of *Capsosira, Chlorogloeopsis, Fischerella, Hapalosiphon, Mastigocladopsis, Mastigocladus, Nostochopsis, Stigonema, Symphyonema, Symphyonemopsis, Umezakia*, and *Westiellopsis*. In certain aspects, the cyanobacterium is *Synechocystis* sp. PCC 6803 or *Thermosynechococcus elongatus* strain BP-1.

In some embodiments where the gene(s) of interest is/are altered in their expression level, deleted, or introduced, the modified photoautotrophic bacterium is further defined as having increased production of one or more lipids relative to an amount of lipid production by a photoautotrophic bacterium in which expression of and/or gene product function of the one or more genes of interest has not been altered. The modified photoautotrophic bacterium may be further defined as having increased lipid content relative to a lipid content of a photoautotrophic bacterium in which expression of and/or gene product function of the one or more genes of interest has not been altered. The lipid content can be increased by 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99, 100% or more, or any range or integer derivable between any of these point. Further, the lipid content can be 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, or 99% or any range or integer derivable between any of these points of the theoretical dry weight of the organism as calculated by methods known to those of skill. The genes of interest that can be overexpressed and can lead to an increase in lipid production or lipid content can include a vesicle-inducing protein in plastids 1 (VIPP1) gene (sll0617), the similar pspA-type gene slr1188, the slr1471 gene that has similarity to yidC and oxaI that are important for thylakoid membrane formation and composition, acetyl-CoA carboxylase genes (sll0728, slr0435, sll0053, and sll0336), a transacetylase gene, fatty acid biosynthesis genes fabD (slr2023), fabH (slr1511), fabF (sll1069 and slr1332), fabG (slr0886), fabZ (sll1605), and fabI (slr1051), plastoglobulin/fibrillin genes (slr1024 and sll1568) coding for proteins that cover hydrophobic entities associated with fibrils or thylakoid membranes, a desaturase gene, sll1848 encoding 1-acylglycerol-3-phosphate acyl transferase, or phospholipid-glycerol acyltransferase genes such as slr2060. The lipid content of membranes may also be enhanced by overexpression of proteases that recognize proteins in membranes (including ftsH genes sll1463, slr0228, slr1390, and slr1604, clpB genes slr0156 and slr1641, and clpP genes slr0542, sll0534, and slr0165) and by metabolic engineering to increase the amount of fixed carbon that is used for lipid production (for example, by downregulation of sll0920, the PEP carboxylase gene, and sll0401, the citrate synthase gene, and/or deletion of genes involved in synthesis of storage compounds including slr1176 involved in glycogen biosynthesis, slr1829/1830 involved in polyhydroxybutyrate formation and metabolism, and slr2001/2002 involved in cyanophycin formation and metabolism). Moreover, the type of lipids produced by the organism can be altered by introduction of genes that allow formation of triglycerides (such as diacylglycerol acyltransferase from yeast (LRO1) or *Arabidopsis* (TAG1)) or that qualitatively or quantitatively alter the formation of glycolipids, sulfolipids, and phospholipids, or the degree of saturation of the fatty acids. Fatty acid desaturation in *Synechocystis* is catalyzed by DesA (Slr1350), DesB (Sll1441), DesC (Sll0541), and DesD (Sll0262), and regulation of expression of the corresponding genes modulates fatty acid desaturation levels that in turn modulate temperature tolerance of the cells. Differential expression of genes involved in pathway regulation or regulation of thylakoid membrane formation will also lead to increased lipid content or increased biofuel value. In certain embodiments, the genes of interest include the sll0336, sll0728, sll1568, sll1848, slr2060, sll0617, slr1471, sll1463, slr0228, slr1024, slr1390, slr1604, slr0156, slr1641, slr0542, slr0165, slr0435, sll0053, slr2023, slr1511, sll1069, slr1332, slr0886, sll1605, slr1051, slr1176, slr1188, slr1024, sll1568, slr1829, slr1830, slr2001, slr2002, slr1350, sll1441, sll0541, sll0262, sll0920, sll0401, and sll0534 of *Synechocystis* sp. PCC 6803. A person of ordinary skill in the art will recognize that homologues of these genes exist in other photoautotrophic bacteria. These homologues can also be altered, introduced or deleted in those species. Moreover, the type of lipids in a cell can be modified by introduction of genes that enable triacylglycerol synthesis. Triacylglycerol overproduction may lead to synthesis of lipid bodies in the cell that can be harvested and isolated.

Not to be bound to any particular theory, triacylglycerol is formed from phosphatidic acid (the Sll1848 product) by removal of the phosphate, yielding diacylglycerol, followed by addition of another acyl group by diacylglycerol acyl transferase. The enzyme responsible for removal of the phosphate from phosphatidic acid is phosphatidic acid phosphatase possibly encoded by sll0545 in *Synechocystis*. This gene can be overexpressed, in conjunction with phosphatidic acid phosphatases from high-triglyceride strains (such as *Rhodococcus opacus*). To form triglycerides, LRO1 from yeast or important diacylglycerol acyltransferases from other systems can be introduced. LRO1 is similar to the lecithin cholesterol acyltransferase gene in eukaryotes, and mediates the majority of triglyceride synthesis in yeast during exponential growth. Homologues are present in oilseed plants, and the acyl donor for this enzyme may be phospholipids. In addition, diacylglycerol acyltransferase from *Arabidopsis* (cDNA from the TAG1 locus) that is likely to use acyl-CoA as the acyl donor can be introduced. In this way, triglyceride formation in *Synechocystis* may be maximized. In prokaryotes, the produced triglycerides are usually stored as cytoplasmatic inclusions, similar to oil bodies in plant oil seeds that are small lipid droplets surrounded by a protein/phospholipids monolayer. They are essentially pure triglycerides with small amounts (1-2%) of phospholipids and proteins and are formed at membranes.

In some embodiments where the gene(s) of interest is/are altered in their expression level, deleted, or introduced, the modified photoautotrophic bacterium is further defined as having increased production of one or more carotenoids or other isoprenoids relative to an amount of carotenoid or other isoprenoid production by a photoautotrophic bacterium in which expression of and/or gene product function of the one or more genes of interest has not been altered. The modified photoautotrophic bacterium may be further defined as having increased carotenoid or other isoprenoid content relative to a carotenoid or other isoprenoid content of a photoautotrophic bacterium in which expression of and/or gene product function of the one or more genes of interest has not been altered. Non-limiting examples of carotenoids include beta-carotene, zeaxanthin, myxoxanthophyll, myxol, echinenone, and their biosynthetic intermediates. Non-limiting examples of other isoprenoids include isoprene, tocopherol, and their biosynthetic intermediates. The carotenoid content can be increased by 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99, 100% or more, or any range or integer derivable between any of these point. Further, the carotenoid content can be 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, or 99% or any range or integer derivable between any of these points of the theoretical dry weight of the organism as calculated by methods known to those of skill. A content of any other isoprenoids in the organism can be increased by 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99, 100% or more, or any range or integer derivable between any of these point. Additionally, some isoprenoids that may not be produced in a native organism can be produced in the modified organisms via the methods disclosed herein. The content of any isoprenoid can be 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, or 99% or any range or integer derivable between any of these points of the theoretical dry weight of the organism as calculated by methods known to those of skill. The genes of interest that can be modified and can lead to an altered expression in carotenoid production or carotenoid content can be genes that express or regulate production of the C5 compounds IPP and DMAPP which are carotenoid precursors (e.g., slr0348 from *Synechocystis* sp. PCC 6803); genes that express or regulate production of isopentenyl diphosphate isomerases (e.g., sll1556 from *Synechocystis* sp. PCC 6803); the crtP gene (e.g., slr1254 from *Synechocystis* sp. PCC 6803); the crtQ gene (e.g., slr0940 from *Synechocystis* sp. PCC 6803); the crtD gene (e.g., slr1293 from *Synechocystis* sp. PCC 6803); the crtL$^{diox}$ gene (e.g., sll0254 from *Synechocystis* sp. PCC 6803); and the crtR gene (e.g., sll1468 from *Synechocystis* sp. PCC 6803). To provide *Synechocystis* with the potential to synthesize isoprene, the gene of interest may be an isoprene synthase gene from a plant, such as a poplar variety, or a homologue thereof that is introduced into *Synechocystis* under a strong promoter. A person of ordinary skill in the art will recognize that homologues of these genes exist in other photoautotrophic bacteria. These homologues can also be overexpressed or altered in those species.

In some embodiments where the gene(s) of interest is/are altered in their expression level, deleted, or introduced, the modified photoautotrophic bacterium is further defined as having increased production of one or more carbohydrates relative to an amount of carbohydrate production by a photoautotrophic bacterium in which expression of and/or gene product function of the one or more genes of interest has not been altered. The modified photoautotrophic bacterium may be further defined as having increased carbohydrate content relative to a carbohydrate content of a photoautotrophic bacterium in which expression of and/or gene product function of the one or more genes of interest has not been altered. A content of a carbohydrate in the organism can be increased by 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99, 100% or more, or any range or integer derivable between any of these point. Additionally, some carbohydrates that may not be produced in a native organism can be produced in the modified organisms via the methods disclosed herein. The content of any one or more of the carbohydrates produced in the organism can be individually or collectively with other carbohydrates 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, or 99% or any range or integer derivable between any of these points of the theoretical dry weight of the organism as calculated by methods known to those of skill. Non-limiting examples of carbohydrates include monosaccharides and monosaccharide phosphates (e.g., glucose, fructose, galactose, xylulose-5-phosphate, ribulose-5-phosphate, ribose-5-phosphate, fructose-6-phosphate, glucose-6-phosphate, sedoheptulose-7-phosphate, erythrose-4-phosphate, sedoheptulose-bisphosphate, and fructose-bisphosphate), disaccharides (e.g., sucrose), oligosaccharides (e.g., fructo-oligosaccharides and mannan-oligosaccharides), and polysaccharides (e.g., glycogen and its derivatives). A person of ordinary skill in the art will recognize that genes for glycogen synthetases and the glycogen branching enzyme can be mutated (e.g. insertions or deletions) in a manner where the carbohydrates cannot be converted to glycogen but rather are converted into polylactic acid (PLA), poly-3-hydroxybutyrate (PHB) or another polyhydroxyalkanoate (PHA), or lipids or other biofuels. Alternatively, the gene may be one that is involved in central carbon metabolism.

In certain aspects, the genes of interest are operably linked to a constitutive promoter. Non-limiting examples of constitutive promoters include psbDII, psbA3, and psbA2 promoters. The genes of interest can be operably linked to an inducible promoter. Non-limiting examples of inducible promoters include nirA, isiAB, petE, nrsRS, nrsABCD, and ndhF3 promoters. Multiple genes can be introduced to be under the control of the same promoter.

In another embodiment of the present invention, there is disclosed a method of increasing the production of a desired product from a photoautotrophic bacterium. The method can include altering expression of one or more genes of interest and/or gene product function resulting in an increase in production of one or more product or one or more genes of interest in a photoautotrophic bacterium, wherein said altering results in increased production of the one or more product relative to the amount of that product produced by a photoautotrophic bacterium in which expression of the one or more genes of interest is not altered. The method can further include growing the photoautotrophic bacterium under suitable conditions to produce an increased amount of the desired product. This may include optimization of temperature (including temporal and spatial variation in temperature), nitrogen levels (including the specific chemical make-up of the nitrogen in terms of nitrate, nitrite, organic amines, ammonia, etc.), carbon dioxide levels, light intensities, light exposure times (or more generally temporal modulation of light intensities), light wavelengths (spectral modulation of light intensities), light distribution (spatial modulation of light intensities), phosphorous levels, sulfur levels (including specific levels of different forms of sulfur such as organic sulfur, sulfate, etc.), mineral levels (including the specific levels of individual metals such as iron, magnesium, manganese, zinc, etc.), mixing rates (including modulation of mixing as a function of time or position), bacterial density (how fast bacteria are harvested resulting in a particular steady state cell density), and the speed and temporal modulation of nutrient influx (carbon, nitrogen, sulfur, phosphorous, minerals, etc.) as well as other aspects of the environment that are important to the growth rate and composition of the bacteria. The photoautotrophic bacterium can be of a type that uptakes and fixes carbon dioxide. Modulating the level of expression of the genes of interest and/or deletion of native gene(s) and/or introduction of foreign gene(s) can increase the uptake and fixation of carbon dioxide relative to the amount of uptake and fixation of carbon dioxide by a photoautotrophic bacterium that does not have an altered expression level of the gene of interest and/or deletion of native gene(s) and/or introduction of foreign gene(s). The desired product can be (but is not limited to) a lipid (or mixture of lipids), a carbohydrate (or mixture of carbohydrates), the sugar composition of carbohydrates in general, a carotenoid (or mixture of carotenoids, for example, beta-carotene, zeaxanthin, myoxoxanthophyll, myxol, echinenone, and their biosynthetic intermediates), another isoprenoid (or mixture of isoprenoids), a protein (or mixture of proteins), the amino acid composition of protein in general, or the storage product cyanophycin (and related compounds). In the case of proteins, a specific mixture of proteins may be produced that is optimized for the purposes of animal feed, creating vaccines, or other valuable protein products. Also, specific proteins can be downregulated in their levels in the cell if they contaminate or reduce the yield of the desired product. The method can further include processing the desired product into a biofuel. Non-limiting examples of biofuel include biodiesel, bioalcohol (e.g., methanol, ethanol, propanol, and butanol), and biogas (hydrogen, isoprene, methane, ethane, propane, and butane). In other aspects, the method can include processing the desired product into a bioplastic. Non-limiting examples of bioplastics include polylactic acid (PLA), poly-3-hydroxybutyrate (PHB), or poly-3-hydroxyalkanoate (PHA). The desired product can be processed into an animal feed additive, or an organic fertilizer.

Suitable growth conditions for the photoautotrophic bacterium include those described throughout this specification and those known to persons of ordinary skill in the art. In one embodiment, for example, suitable growth conditions include providing the bacteria with a source of carbon dioxide. The source of carbon dioxide can vary. In one embodiment, the source is obtained from flue gas. In another embodiment, the source of carbon dioxide can be atmospheric. Suitable growth conditions can include providing the bacteria with a source of fixed nitrogen. The source of fixed nitrogen can vary. In one embodiment, the source is obtained from ground water, ammonia, sodium nitrate or ammonium nitrate. The amount of carbon dioxide provided to the photoautotrophic bacterium can be between 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 15, or 20% or more, with the % referring to the partial pressure of $CO_2$ in the gas provided to the culture. The amount of fixed-nitrogen provided to the photosynthetic bacterium can be between 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, or 95 mM or more in the medium. Suitable growth conditions can include growing the bacteria at a temperature range of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 80, 90° C., or more or any range or integer derivable therein. In certain aspects, the temperature range is between 10 and 55° C. Suitable growth conditions can also include subjecting the photoautotrophic bacterium to light (e.g., sunlight).

Another embodiment of the present invention includes a method for producing a desired product from a photoautotrophic bacterium. The method can include obtaining a modified photoautotrophic bacterium of the current invention or produced by the methods of the current invention in which altering expression of one or more genes of interest and/or gene product function results in an increase in production of one or more products or one or more genes of interest in a photoautotrophic bacterium, resulting in increased production of a desired product relative to the amount of the desired product produced by a photoautotrophic bacterium in which expression of the one or more genes of interest is not altered; growing the photoautotrophic bacterium under suitable conditions to produce the desired product; and isolating the desired product. The photoautotrophic bacterium can be of a type that uptakes and fixes carbon dioxide. Modifying the level of expression of the genes of interest and/or deletion of native gene(s) and/or introduction of foreign gene(s) can increase the uptake and fixation of carbon dioxide relative to the amount of uptake and fixation of carbon dioxide by a photoautotrophic bacterium that does not have a modified level of expression of the genes of interest and/or that do not carry a deletion of native gene(s) and/or an introduced foreign gene(s). Non-limiting examples of desired products include lipids, carbohydrates, carotenoids, other isoprenoids, pigments, anti-oxidants, other secondary metabolites, proteins, or a mixture thereof. Non-limiting examples of isolation steps include those described throughout this specification and those known to persons of ordinary skill in the art. Non-limiting examples include extraction with an organic solvent, with hairiness chemicals (for example, $CO_2$ or water) under super-critical conditions, or by two-phase partitioning. The method can further include processing the desired product into a biofuel, a bioplastic, a carotenoid, an animal feed, or a fertilizer by methods described in this specification and those known to persons of ordinary skill in the art.

Another embodiment of the present invention includes a method of fixing carbon dioxide. The method can include obtaining a modified photoautotrophic bacterium of the current invention or produced by the methods of the current invention that is capable of uptaking and fixing carbon dioxide, in which altering expression of one or more genes of interest and/or gene product function results an increase in the uptake and fixation of carbon dioxide relative to the amount of uptake and fixation of carbon dioxide by a photoautotrophic bacterium in which expression of the one or more genes of interest is not altered; growing the photoautotrophic bacterium under suitable conditions to uptake and fix carbon dioxide; and providing a carbon dioxide source to the modified photoautotrophic bacteria, wherein at least a portion of the carbon dioxide from the source is fixed by the modified photoautotrophic bacteria. A non-limiting source of the carbon dioxide source can be flue gas, atmospheric $CO_2$, or other $CO_2$ sources. The method can further include fixing at least a portion of the carbon dioxide in the flue gas.

It is contemplated that any embodiment discussed in this specification can be implemented with respect to any method or composition of the invention, and vice versa. Furthermore, compositions of the invention can be used to achieve methods of the invention.

The use of the word "a" or "an" in the claims and/or the specification may mean "one," but it is also consistent with the meaning of "one or more," "at least one," and "one or more than one."

The phrase "one or more" as found in the claims and/or the specification is defined as 1, 2, 3, 4, 5, 6, 7, 8, 9, 10, or more.

The phrase "one or more product" can be multiple products in a single class (i.e. 2 or more lipids; 2 or more biogases), single product in multiple classes (i.e. 1 lipid, 1 fatty acid, 1 carbohydrate, etc.), or a combination thereof.

The term "altered", for example relating to gene expression, includes any type of alteration, including (a) upregulation or down-regulation of expression; (b) alteration of naturally occurring gene (for example, by inducible promoter construct, etc.); (c) mutation in endogenous gene; alteration by transgenic construct (i.e. transgene) (naturally occurring in a different organism or mutated); (d) combinations thereof; etc.

Throughout this application, the terms "about" and "approximately" indicate that a value includes the inherent variation of error for the device, the method being employed to determine the value, or the variation that exists among the study subjects. In one non-limiting embodiment the terms are defined to be within 10%, preferably within 5%, more preferably within 1%, and most preferably within 0.5%.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 8C-F are electron micrographs of a mutant strain of *Synechocystis* sp. PCC 6803 cyanobacteria that overexpresses the VIPP1 gene encoding for a protein involved in thylakoid membrane biogenesis. FIG. 8C The amount of thylakoid membrane is significantly increased and appressed membranes (white asterisks) seem to diverge to single thylakoid sheets (white arrows). FIG. 8D Enlargement of FIG. 8C. FIG. 8E Shows the presence of lamellar structures (black asterisks) that have close association with the thylakoid membrane (black arrowheads) that are unique for this mutant strain. FIG. 8F Enlargement of FIG. 8E. Scale bars=200 nm.

FIG. 9A Wild-type cells in early exponential phase cultured in standard BG-11 medium. FIG. 9B Stationary phase wild-type cells cultured in N-limited medium (1.67 mM nitrate). FIG. 9C Early exponential phase wild-type cells cultured in modified BG-11 medium in which NaNO$_3$ (16.7 mM) was replaced with 10 mM NH$_4$Cl. FIG. 9D PS II-less/oxidase-less cells in mid-exponential phase. FIG. 9E Oxidase-less cells in mid-exponential phase. FIG. 9F. NDH-1-less cells in mid-exponential phase. All cultures were grown photoautotrophically except the PSII-less/oxidase-less culture. Bar size: 1 µm.

FIG. 10A wild type; FIG. 10B the oxidase-less strain; FIG. 10C the PS II-less/oxidase-less strain; and FIG. 10D wild type after N-starvation. The larger white spaces are due to PHA that has been washed out during preparation of the thin sections. Bar size 200 nm.

DETAILED DESCRIPTION

Figure 1:
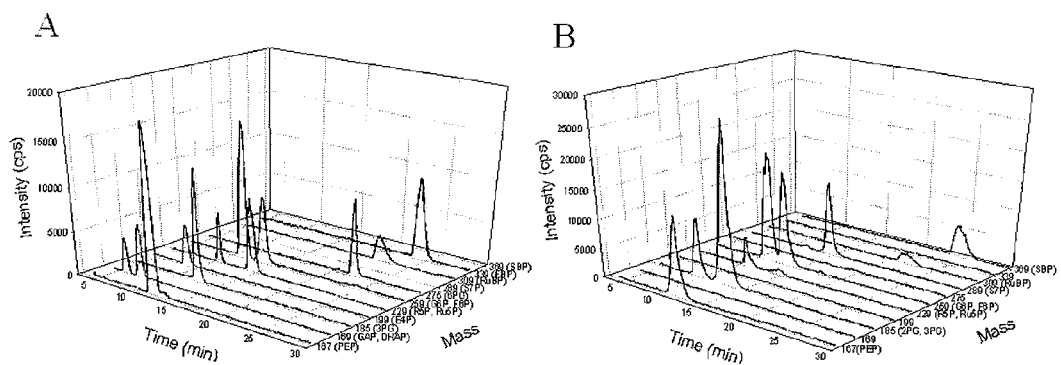
FIG. 1. LC/MS of sugar phosphate standards and *Synechocystis* extracts. The LC elution time is on the X axis, and sugar phosphate masses representing specific sugar phosphates are on the Y axis. The Z axis represents the intensity of the MS signal. A. Sugar phosphate standards at a concentration of 20 μM. B. LC/MS on cell extracts from photomixotrophically grown *Synechocystis* wild-type cultures monitoring the masses of specific sugar phosphates. Note that some intermediates were present in the extract at significant concentrations whereas others were essentially undetectable.

As noted above, there is an ongoing problem with polluting the environment with carbon dioxide. The global production of carbon dioxide from fossil fuel consumption which is estimated to be between 7-8 billion tons/year (Marland et al. 2006). Additionally, statistics show an ever increasing consumption of the world's fossil fuel resources. Although methods currently exist to reduce the amount of carbon dioxide pollution and use alternative sources for energy, these methods can often times be costly and inefficient.

Applicant's invention overcomes the current deficiencies in the art. For instance, the present invention discloses photoautotrophic bacteria, and corresponding methods of using these bacteria, that have been modified to include genes of interest that have been modified in their sequence or level of expression, and/or that have been deleted and/or that have been introduced from foreign sources, wherein the modification in the sequence or expression level or introduction or deletion of the genes of interest increase production of a desired product (e.g., lipid, a carotenoid, another isoprenoid such as isoprene or tocopherol, another secondary metabolite, a carbohydrate, cyanophycin, or a protein) in the bacterium relative to the amount of the desired product in a photoautotrophic bacterium that is not modified to alter the genes of interest. The modified photoautotrophic bacterium can be of a type that uptakes and fixes carbon dioxide. In certain aspects, altering the expression or sequence of the genes of interest or deleting or introducing genes of interest can also increase the uptake and fixation of carbon dioxide relative to the amount of uptake and fixation of carbon dioxide by a photoautotrophic bacterium that is not modified to alter the genes of interest.

These and other aspects of the present invention are described in the following sections in further detail.

A. Photoautotrophic Bacteria

Photoautotrophic bacteria include bacteria that are capable of synthesizing food using light as an energy source. Photoautotrophs are also capable of using carbon dioxide as its principal source of carbon. Non-limiting examples of photoautotrophic bacteria that can be used in the context of the present invention include cyanobacteria, green sulfur bacteria, green non-sulfur bacteria, heliobacteria, photosynthetic acidobacteria, purple sulfur bacteria, and purple non-sulfur bacteria. In particular embodiments, the photoautotrophic bacteria are cyanobacteria.

1. Cyanobacteria

In general, cyanobacteria can be found in several habitats around the world. For instance, this type of bacteria has been found in oceans, fresh water, bare rock, and soil. Typically, cyanobacteria include unicellular, colonial, and filamentous forms. Some filamentous colonies show the ability to differentiate into vegetative cells and photosynthetic cells. In some instances, a thick-walled heterocyst that contains the enzyme nitrogenase (used for nitrogen fixation) can form when fixed nitrogen is at low concentration. Heterocyst-forming species are specialized for nitrogen fixation and are able to fix nitrogen gas into ammonia ($NH_3$), nitrites ($NO_2^-$), or nitrates ($NO_3^-$) which can subsequently be converted to proteins and nucleic acids. Cyanobacteria typically include a thick cell wall which stains Gram-negative.

The study of cyanobacterial cell structure, organization, function, and biochemistry has been the subject of many investigations. Work from the early 1960s through the 1980s led to insights about the general intracellular organization of many cyanobacterial species and identified several cellular structures such as light-harvesting antennae, the phycobilisomes (Gantt and Conti 1969; Edwards and Gantt 1971; Bryant et al. 1979), polyphosphate bodies, cyanophycin granules, polyhydroxyalkanoate (PHA) granules (Jensen and Sicko 1971), carboxysomes/polyhedral bodies, lipid bodies, thylakoid centers, DNA-containing regions (Asato and Ginoza 1973; Roberts and Koths 1976), and ribosomes (Ris and Singh 1961).

For instance, cyanobacteria include a highly organized system of internal membranes which function in photosynthesis. Photosynthesis in cyanobacteria generally uses water as an electron donor and produces oxygen as a by-product. Cyanobacteria can uptake carbon dioxide and reduce it to form carbohydrates, lipids, and other carbon containing by-products. In most cyanobacteria, the photosynthetic machinery is embedded into an internal membrane system (i.e., thylakoid membranes).

There are over a thousand different cyanobacterial species known. For instance, cyanobacteria can be classified into at least the following orders Chroococcales, Nostocales, Oscillatoriales, Pleurocapsales, Prochlorophytes, or Stigonematales. Non-limiting examples of cyanobacterial genera of the order Chroococcales include *Aphanocapsa, Aphanothece, Chamaesiphon, Chroococcus, Crocosphaera, Cyanobacterium, Cyanobium, Cyanothece, Dactylococcopsis, Gloeobacter, Gloeocapsa, Gloeothece, Euhalothece, Halothece, Johannesbaptistia, Merismopedia, Microcystis, Rhabdoderma, Synechococcus, Synechocystis,* and *Thermosynechococcus*. Non-limiting examples of cyanobacterial genera of the order Nostocales include *Coleodesmium, Fremyella, Microchaete, Rexia, Spirirestis, Tolypothrix, Anabaena, Anabaenopsis, Aphanizomenon, Aulosira, Cyanospira, Cylindrospermopsis, Cylindrospermum, Nodularia, Nostoc, Richelia, Calothrix, Gloeotrichia,* and *Scytonema*. Non-limiting examples of cyanobacterial genera of the order Oscillatoriales include *Arthrospira, Geitlerinema, Halomicronema, Halospirulina, Katagnymene, Leptolyngbya, Limnothrix, Lyngbya, Microcoleus, Oscillatoria, Phormidium, Planktothricoides, Planktothrix, Plectonema, Limnothrix, Pseudanabaena, Schizothrix, Spirulina, Symploca, Trichodesmium,* and *Tychonema*. Non-limiting examples of cyanobacterial genera of the order Pleurocapsales include *Chroococcidiopsis, Dermocarpa, Dermocarpella, Myxosarcina, Pleurocapsa, Stanieria,* and *Xenococcus*. Non-limiting examples of cyanobacterial genera of the order Prochlorophytes include *Prochloron, Prochlorococcus,* and *Prochlorothrix*. Non-limiting examples of cyanobacterial genera of the order Stigonematales include *Capsosira, Chlorogloeopsis, Fischerella, Hapalosiphon, Mastigocladopsis, Mastigocladus, Nostochopsis, Stigonema, Symphyonema, Symphyonemopsis, Umezakia,* and *Westiellopsis*.

The cyanobacterial species identified throughout this specification and those known to persons of ordinary skill in the art are contemplated as being useful in the context of the present invention. By way of example only, the following sections provide detailed descriptions of two specific species of cyanobacteria: *Synechocystis* sp. PCC 6803 and *Thermosynechococcus elongatus* sp. BP-1.

2. *Synechocystis* sp. PCC 6803

*Synechocystis* sp. PCC 6803 is a unicellular organism that displays a unique combination of highly desirable molecular genetic, physiological, and morphological characteristics. For instance, this species is spontaneously transformable, incorporates foreign DNA into its genome by double-homologous recombination, grows under many different physiological conditions (e.g., photoauto/mixo/heterotrophically), and is relatively small (~1.5 µm in diameter) (Van de Meene et al. 2005 which is incorporated by reference). Its entire genome has been sequenced (Kaneko et al. 1996), and a high percentage of open reading frames without homologues in other bacterial groups have been found. *Synechocystis* sp. PCC 6803 is available from the American Type Culture Collection, accession number ATCC 27184 (Rippka et al., 1979, which is incorporated by reference).

3. *Thermosynechococcus elongatus* sp. BP-1

*Thermosynechococcus elongatus* sp. BP-1 is a unicellular thermophilic cyanobacterium that inhabits hot springs and has an optimum growth temperature of approximately 55° C. (Nakamura et al. 2002 which is incorporated by reference). The entire genome of this bacterium has been sequenced. The genome includes a circular chromosome of 2,593,857 base pairs. A total of 2,475 potential protein-encoding genes, one set of rRNA genes, 42 tRNA genes representing 42 tRNA species and 4 genes for small structural RNAs were predicted.

B. Genes of Interest

In preferred aspects of the present invention, the genes of interest include those that when altered in sequence or expression level, deleted or introduced, increase production of a desired product (e.g., a lipid, another fuel such as hydrogen or alcohols, a carotenoid, another isoprenoid such as isoprene or tocopherol, a carbohydrate, cyanophycin, or a protein) in the bacterium relative to the amount of the production of the desired product in a bacterium that is not modified with respect to the genes of interest. In certain aspects, the genes of interest, when altered in sequence or expression level, deleted or introduced, can also increase the uptake and fixation of carbon dioxide relative to the amount of uptake and fixation of carbon dioxide by a bacterium that is not modified with respect to the genes of interest.

In certain aspects, the genes of interest include those that, where the gene(s) of interest is/are altered in their sequence or expression level, deleted, or introduced, the altered expression level, deletion, or introduction can increase the production of a lipid in the bacterial cell. The altered expression level, deletion or introduction can increase the lipid content of the bacterial cell. Non-limiting examples of such genes include: a vesicle-inducing protein in plastids 1 (VIPP1) gene (sll0617), the similar pspA-type gene slr1188, the slr1471 gene that has similarity to yidC and oxaI that are important for thylakoid membrane formation and composition, acetyl-CoA carboxylase genes (sll0728, slr0435, sll0053, and sll0336), fatty acid biosynthesis genes fabD (slr2023), fabH (slr1511), fabF (sll1069 and slr1332), fabG (slr0886), fabZ (sll1605), and fabI (slr1051), plastoglobulin/fibrillin genes (slr1024 and sll1568) coding for proteins that cover hydrophobic entities associated with fibrils or thylakoid membranes, sll1848 encoding 1-acylglycerol-3-phosphate acyl transferase, or phospholipid-glycerol acyltransferase genes such as slr2060. The lipid content of membranes may also be enhanced by overexpression of proteases that recognize proteins in membranes (including ftsH genes sll1463, slr0228, slr1390, and slr1604, clpB genes slr0156 and slr1641, and clpP genes slr0542, sll0534, and slr0165) and by metabolic engineering to increase the amount of fixed carbon that is used for lipid production (for example, by downregulation of sll0920, the PEP carboxylase gene, and sll0401, the citrate synthase gene, and/or deletion of genes involved in synthesis of storage compounds including slr1176 involved in glycogen biosynthesis, slr1829/1830 involved in polyhydroxybutyrate formation and metabolism, and slr2001/2002 involved in cyanophycin formation and metabolism). Although the designations identified above are for *Synechocystis*, homologues are present in other cyanobacteria and are contemplated as being used in the context of the present invention.

In other aspects, the genes of interest may be modified to display an altered level of a carotenoid or other isoprenoids in the bacterial cell. The modification can increase the carotenoid or other isoprenoid content of the bacterial cell. Non-limiting examples of carotenoids include beta-carotene, zeaxanthin, myxoxanthophyll, myxol, echinenone, and their biosynthetic intermediates. Non-limiting examples of other isoprenoids include isoprene, tocopherol, and their biosynthetic intermediates. Non-limiting examples of such genes include: genes that express or regulate production of the C5 compounds IPP and DMAPP which are carotenoid precursors (e.g., slr0348 from *Synechocystis* sp. PCC 6803); genes that express or regulate production of isopentenyl diphosphate isomerases (e.g., sll1556 from *Synechocystis* sp. PCC6803); the crtP gene (e.g., slr1254 from *Synechocystis* sp. PCC 6803); the crtQ gene (e.g., slr0940 from *Synechocystis* sp. PCC 6803); the crtD gene (e.g., slr1293 from *Synechocystis* sp. PCC6803); the crtL$^{diox}$ gene (e.g., sll0254 from *Synechocystis* sp. PCC 6803); and the crtR gene (e.g., sll1468 from *Synechocystis* sp. PCC 6803). Although the designations identified above are for *Synechocystis*, homologues are present in other cyanobacteria and are contemplated as being used in the context of the present invention. Also, genes from other organisms such as plants (e.g., the isoprene synthase) are contemplated as being used in the context of the present invention.

In additional aspects, altering the sequence or expression of the genes of interest and/or deletion or introduction of genes can greatly modify the production and level of a carbohydrate in the bacterial cell. The altered expression and/or deletion or introduction of genes can modify the carbohydrate content of the bacterial cell. Such genes include those that modify production of a carbohydrate (e.g., monosaccharides and monosaccharide phosphates (e.g., glucose, fructose, xylulose-5-phosphate, ribulose-5-phosphate, ribose-5-phosphate, fructose-6-phosphate, glucose-6-phosphate, sedoheptulose-7-phosphate, erythrose-4-phosphate, sedoheptulose-bisphosphate, and fructose-bisphosphate)), disaccharides (e.g., sucrose), oligosaccharides (e.g., fructo-oligosaccharides and mannan-oligosaccharides), and polysaccharides (e.g., glycogen and its derivatives)) or the carbohydrate content of the bacterium cell when overexpressed. Non-limiting examples of such genes include: genes that express glycogen synthetases; and genes that express glycogen branching enzymes). A person of ordinary skill in the art will recognize that genes glycogen synthetases and the glycogen branching enzyme can be mutated (e.g. insertions or deletions) in a manner where the carbohydrates are converted into polylactic acid (PLA), poly-3-hydroxybutyrate (PHB), polyhydroxyalkanoate (PHA) or lipids rather than being stored as glycogen.

The genes and encoded proteins described in the present application are available, as would be appreciated by one of skill, in the GenBank and CyanoBase databases, which are available online. Throughout the specification, various genes of the organism *Synechocystis* sp. PCC 6803 (strain: PCC 6803) are described, e.g., sll0617. This terminology, e.g., "sll0617," refers to an alternate alias or locus tag for each respective gene, and may be used to obtain the complete gene sequence via the databases described above. For example, the term "sll0617" in combination with the term "*Synechocystis* sp. PCC 6803" may be queried in the GenBank database, accessible via the NCBI databases described above, to obtain gene information and a link to the full gene sequence. The fully annotated *Synechocystis* genome, including its open reading frames, is accessible via the CyanoBase databases described above. This approach will be immediately appreciated by one of skill in the art.

C. Modulating Expression of a Gene of Interest

Embodiments of the invention include methods and compositions for modulating expression levels for certain genes of interest within the photoautotrophic bacteria of the present invention. The genes of interest may be modified in their sequence or level of expression, and/or deleted and/or introduced from foreign sources. This can lead to modulated production of the corresponding desired gene product (e.g., protein or enzyme) and/or modulation of the pathways related to such gene products (e.g., increasing or over-expressing a gene of interest to obtain an increased amount of a corresponding gene product and/or components of metabolic pathways associated with the gene product). Embodiments of the invention may include multiple alterations that are introduced into one or more genes, wherein the multiple alterations collectively increase the production of the desired product.

1. Recombinant Expression Systems

In certain embodiments, a gene product and/or components of the metabolic pathways associated with the gene product are synthesized using recombinant expression systems (e.g., recombinant photoautotrophic bacteria of the present invention). Generally this involves placing the DNA encoding the desired gene product (e.g., leading to the formation of a lipid, a carbohydrate, a carotenoid, or cyanophycin) under the control of an appropriate regulatory region and expressing the protein in the photoautotrophic bacteria of the present invention (i.e, a host), and if desired isolating the expressed gene product or products of the pathways associated with the gene product. This allows the protein encoded for by a gene to be expressed in increased quantities. This can come about by increasing the number of copies of the gene in the host, increasing the binding strength of the promoter region in the host, or by promoter replacement. Other mechanisms for alteration of a gene include reduced expression, deletion, insertion of a gene from a different organism or a change in its sequence or in a regulatory protein.

Typically, the DNA sequence for a gene product will be cloned or subcloned into a vector (e.g., plasmid) containing a promoter, which is then transformed into the bacterium leading to integration of the appropriate DNA region and causing the bacterium to express the gene product. Regulatory sequences may also be inserted into the genome of a bacterium of the present invention (e.g., heterologous regulatory sequence that is operatively coupled to a gene encoding a gene product of interest). Alternatively, an endogenous promoter or regulatory mechanism may be stimulated by the exposing the host to a particular condition or a particular substance that increases protein expression by stimulating natural regulatory processes.

A frequently used method for gene/expression insertion for cyanobacteria includes integrating constructs into the genome by double-homologous recombination (see, e.g., Li et al. (1993); Williams (1998); Grigorieva et al. (1982) which are incorporated by reference). In certain embodiments, double homologous recombination can be used to introduce gene interruptions or deletions using a construct with two regions of sequence identity with the cyanobacterial genome.

a. Nucleic Acids

Using the information provided in this specification, the nucleic acids that are overexpressed by the photoautotrophic bacteria of the present invention can be prepared using standard methods known to those of skill in the art. For example, the protein-encoding nucleic acid(s) may be cloned, or amplified by in vitro methods, such as the polymerase chain reaction (PCR), etc. A variety of cloning and in vitro amplification methodologies are well-known to persons of skill. Examples of techniques sufficient to direct persons of skill through in vitro amplification methods are found in Berger, Sambrook, and Ausubel, as well as U.S. Pat. No. 4,683,202; Innis (1990); The Journal of NIH Research (1991); Kwoh et al. (1989); Guatelli et al., (1990); Lomell et al., (1989); Landegren et al., (1988); Van Brunt (1990); Wu and Wallace, (1989); and Barringer et al. (1990).

The nucleic acids encoding desired products of the present invention can also be prepared by cloning and restriction of appropriate sequences, or direct chemical synthesis by methods such as the phosphotriester method of Narang et al. (1979); the phosphodiester method of Brown et al. (1979); the diethylphosphoramidite method of Beaucage et al. (1981); and the solid support method of U.S. Pat. No. 4,458,066.

Nucleic acids can be cloned using DNA amplification methods such as polymerase chain reaction (PCR). Thus, for example, the nucleic acid sequence or subsequence is PCR amplified, using a sense primer containing one restriction site and an antisense primer containing another restriction site. This will produce a nucleic acid encoding the desired sequence or subsequence and having terminal restriction sites. This nucleic acid can then be easily ligated into a vector containing a nucleic acid encoding the second molecule and having the appropriate corresponding restriction sites. Suitable PCR primers can be determined by one of skill in the art using the sequence information and representative primers are provided herein. Appropriate restriction sites can also be added to the nucleic acid encoding the desired protein or protein subsequence by site-directed mutagenesis. The plasmid containing the desired sequence or subsequence is cleaved with the appropriate restriction endonuclease and then ligated into the vector encoding the second molecule according to standard methods.

Chemical synthesis typically produces a single-stranded nucleic acid. This may be converted into double-stranded DNA by hybridization with a complementary sequence, or by polymerization with a DNA polymerase using the single strand as a template. One of skill would recognize that chemical synthesis of DNA may be limited, longer sequences may be obtained by the ligation of shorter sequences. Alternatively, subsequences may be cloned and the appropriate subsequences cleaved using appropriate restriction enzymes. The fragments may then be ligated to produce the desired DNA sequence.

b. Vectors

The term "vector" is used to refer to a carrier nucleic acid molecule into which a nucleic acid sequence can be inserted for introduction into a photoautotrophic bacterium of the present invention where it can be integrated into the genome, replicated and/or overexpressed. A nucleic acid sequence can be "exogenous," which means that it is foreign to the bacterium into which the vector is being introduced or that the sequence is homologous to a sequence in the bacterium but in a position within the bacterial cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1989 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular bacterial cell. In addition to control sequences that govern transcription and translation, vectors and expression vectors may contain nucleic acid sequences that serve other functions as well and are described infra.

As noted above, the nucleic acid encoding the desired product to be expressed can be operably linked to appropriate expression control sequences for each bacterial cell. This can include regulatory sequences such as those described throughout this specification, a ribosome binding site, and a transcription termination signal.

i. Regulatory Sequences

The design of the recombinant photoautotrophic bacteria of the present invention may depend on such factors as the choice of the bacterium to be transfected and/or particular protein(s) to be expressed. Use of appropriate regulatory elements can allow for an altered level expression of the polypeptide(s) in a variety of the host cells of the present invention. Regulatory sequences are known to those skilled in the art (see, e.g., Goeddel (1990); Berger and Kimmel, Guide to Molecular Cloning Techniques, Methods in Enzymology 152 Academic Press, Inc., San Diego, Calif.; Sambrook et al. (1989)).

For instance, the desired products can be operably linked to constitutive promoters for high level, continuous expression. Alternatively, inducible and/or tissue-specific promoters can be utilized. Non-limiting examples of such promoters that can be used in the context of the present invention include constitutive promoters such as the psbDII, psbA3, and psbA2 promoters. For instance, Lagarde et al. (2000), provides a detailed description of using the psbA2 promoter in Synechocystis sp strain PCC 6803 to overexpress genes involved in carotenoid biosynthesis, and in He et al. (1999), there is a detailed description of using the psbA3 promoter. The information in these references are incorporated by reference. Non-limiting examples of inducible promoters include nirA, isiAB, petE, nrsBACD, nrsAB, and ndhF3 promoters (see Aichi et al. (2001); Vinnemeier et al. (1998); Zhang et al (1994); Lopez-Maury et al. (2002); McGinn et al. (2003), all of which are incorporated by reference).

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. Additional promoter elements regulate the frequency of transcriptional initiation. Typically, these are located in the region up to 100 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer, operator or other regulatory sequence refers also to an enhancer, operator or other regulatory sequence not normally associated with a nucleic acid sequence in its natural environment. Such promoters, enhancers, operators or other regulatory sequences may include promoters, enhancers, operators or other regulatory sequences of other genes, and promoters, enhancers, operators or other regulatory sequences isolated from any other virus, or prokaryotic or eukaryotic cell, and promoters, enhancers, operators or other regulatory sequences not "naturally occurring," i.e., containing different elements of different transcriptional regulatory regions, and/or mutations that alter expression.

Naturally, it will be important to employ a promoter, enhancer, operator or other regulatory sequence that effectively directs the expression of the DNA segment in the photoautotrophic bacteria of the present invention. Those of skill in the art of molecular biology generally know the use of promoters, enhancers, operators or other regulatory sequences for protein expression (see, for example Sambrook et al. 2001). The promoters employed may be constitutive, condition-specific, inducible, and/or useful under the appropriate conditions to direct altered expression of the introduced DNA segment, such as is advantageous in the large-scale production of desired products. The promoter may be heterologous or endogenous.

ii. Initiation Signals

A specific initiation signal can be required for efficient translation of coding sequences. These signals include the ATG or GTG initiation codon and adjacent sequences such as ribosome-binding sites. Exogenous translational control signals, including the ATG or GTG initiation codon and adjacent sequences such as ribosome-binding sites, may need to be provided. One of ordinary skill in the art would readily be capable of determining this and providing the necessary signals. It is well known that the initiation codon must be "in-frame" with the reading frame of the desired coding sequence to ensure translation of the entire coding region of the gene. The exogenous translational control signals and initiation codons can be either natural or synthetic. The efficiency of expression may be enhanced by the inclusion of appropriate transcription enhancer elements.

iii. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

iv. Splicing Sites

Most transcribed eukaryotic RNA molecules will undergo RNA splicing to remove introns from the primary transcripts. Vectors containing eukaryotic sequences will generally contain cDNA (copies of mRNA) of the transcript for protein expression (see, for example, Chandler et al., 1997, herein incorporated by reference.)

v. Termination Signals

The vectors or constructs of the present invention can comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator can be used in vivo to achieve desirable message levels.

Terminators contemplated for use in the invention include any known terminator of transcription described herein or known to one of ordinary skill in the art, including but not limited to, for example, the termination sequences of genes, such as for example rho-dependent and rho-independent terminators. In certain embodiments, the termination signal may be a lack of transcribable or translatable sequence, such as due to a sequence truncation.

vi. Origins of Replication

In order to propagate a vector in a bacterial cell of the present invention, the vector can contain one or more origins of replication sites (often termed "ori"), which is a specific nucleic acid sequence at which replication is initiated.

vii. Selectable and Screenable Markers

In certain embodiments of the invention, bacterial cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to chloramphenicol, erythromycin, gentimycin, spectinomycin, streptomycin, zeocin, and kanamycin are useful selectable markers. A complementation approach, in which an auxotroph is functionally complemented by the gene it lacks, is also used. In addition to markers conferring a phenotype that allows for the discrimination of transformants based on the implementation of conditions, other types of markers including screenable markers such as GFP and YFP, whose basis is colorimetric fluorescence analysis, are also contemplated. Moreover, markers that employ luciferase can be utilized as reporter genes. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

viii. Non-Limiting Examples of Vectors

In certain embodiments, a plasmid vector is contemplated for use to transform a photoautotrophic bacterial cell of the present. In general, suicide plasmid vectors are used, in which the desired plasmid sequence carrying the gene or construct of interest does not replicate in the photoautotrophic bacterial host and is forced to integrate into the host genome by double-homologous recombination. The plasmid vectors do replicate in *Escherichia coli*. The vector ordinarily carries a replication site recognized in *E. coli*, as well as marking sequences which are capable of providing phenotypic selection in transformed cells of both *E. coli* and the photoautotrophic bacterial cell.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells.

Further useful plasmid vectors include pET vectors suitable for protein overexpression, as well as vectors that include a translational fusion with affinity tags including His tags and Strep tags for later purification and separation or cleavage. Other suitable fusion proteins are those with β-galactosidase, ubiquitin, and the like.

c. Introduction of Nucleic Acids Into the Photoautotrophic Bacteria

Whereas *Synechocystis* sp. PCC 6803 is naturally transformable and does not need treatment to allow efficient DNA uptake and integration into the genome, suitable methods for nucleic acid delivery for transformation of the photoautotrophic bacteria of the present invention can include virtually any method by which a nucleic acid (e.g., DNA) can be introduced into such bacteria, as described herein, or as would be known to one of ordinary skill in the art. Such methods include, but are not limited to, direct delivery of DNA by spontaneous transformation or by standard transformation methods (Sambrook et al. 2001); ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference) and any combination of such methods. Through the application of techniques such as these, the photoautotrophic bacteria of the present invention can be stably transformed.

2. Mutagenesis

Mutagenesis can be a powerful tool for the dissection and engineering of the expression of genes. It can also be used to alleviate feedback regulation of genes and/or eliminate or down regulate competing pathways, etc. Where employed, mutagenesis will be accomplished by a variety of standard, mutagenic procedures. Mutation is the process whereby changes occur in the quantity or structure of an organism. Mutation can involve modification of the nucleotide sequence of a single gene, blocks of genes or the whole chromosome. Changes in single genes may be the consequence of point mutations which involve the removal, addition or substitution of a single nucleotide base within a DNA sequence, or they may be the consequence of changes involving the insertion or deletion of large numbers of nucleotides.

Mutation can be site-directed through the use of particular targeting methods. Mutations can also arise spontaneously as a result of events such as errors in the fidelity of DNA replication or the movement of transposable genetic elements (transposons) within the genome. They also are induced following exposure to chemical or physical mutagens. Such mutation-inducing agents include ionizing radiations, ultraviolet light and a diverse array of chemical such as alkylating agents and polycyclic aromatic hydrocarbons all of which are capable of interacting either directly or indirectly (generally following some metabolic biotransformations) with nucleic acids. The DNA lesions induced by such environmental agents may lead to modifications of base sequence when the affected DNA is replicated or repaired and thus to a mutation.

a. Site-Directed Mutagenesis

Structure-guided site-specific mutagenesis represents a powerful tool for the dissection and engineering of the expression of genes. The technique provides for the preparation and testing of sequence variants by introducing one or more nucleotide sequence changes into a selected DNA.

Site-specific mutagenesis uses specific oligonucleotide sequences which encode the DNA sequence of the desired mutation, as well as a sufficient number of adjacent, unmodified nucleotides. In this way, a primer sequence is provided with sufficient size and complexity to form a stable duplex on both sides of the deletion junction being traversed. A primer of about 17 to 25 nucleotides in length is preferred, with about 5 to 10 residues on both sides of the junction of the sequence being altered.

The technique typically employs a bacteriophage vector that exists in both a single-stranded and double-stranded form. Vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, one first obtains a single-stranded vector, or melts two strands of a double-stranded vector, which includes within its sequence a DNA sequence encoding the desired protein or genetic element. An oligonucleotide primer bearing the desired mutated sequence, synthetically prepared, is then annealed with the single-stranded DNA preparation, taking into account the degree of mismatch when selecting hybridization conditions. The hybridized product is subjected to DNA polymerizing enzymes such as *E. coli* polymerase I (Klenow fragment) in order to complete the synthesis of the mutation-bearing strand. Thus, a heteroduplex is formed, wherein one strand encodes the original non-mutated sequence, and the second strand bears the desired mutation. This heteroduplex vector is then used to transform photoautotrophic bacterial cells of the present invention. Clones can be selected that include recombinant vectors bearing the mutated sequence arrangement.

Comprehensive information on the functional significance and information content of a given residue of protein can best be obtained by saturation mutagenesis in which all 19 amino acid substitutions are examined. The shortcoming of this approach is that the logistics of multiresidue saturation mutagenesis (combinatorial mutagenesis) are daunting (Warren et al., 1996, 1996; Zeng et al., 1996; Burton and Barbas, 1994; Yelton et al., 1995; 1995; Hilton et al., 1996). Hundreds, and possibly even thousands, of site specific mutants must be studied. However, improved techniques make production and rapid screening of mutants much more straightforward, particularly if a stringent functional selection scheme of mutants with desired properties is available. See also, U.S. Pat. Nos. 5,798,208 and 5,830,650, for a description of "walk-through" mutagenesis.

Other methods of site-directed mutagenesis are disclosed in U.S. Pat. Nos. 5,220,007; 5,284,760; 5,354,670; 5,366,878; 5,389,514; 5,635,377; and 5,789,166.

b. Random Mutagenesis i. Insertional Mutagenesis

Insertional mutagenesis is based on the inactivation of a gene via insertion of a known DNA fragment. Because it involves the insertion of some type of DNA fragment, the mutations generated are generally loss-of-function, rather than gain-of-function mutations. However, there are several examples of insertions generating gain-of-function mutations (Oppenheimer et al. 1991). Insertion mutagenesis has been very successful in bacteria and *Drosophila* (Cooley et al., 1988) and has become a powerful tool in plants such as corn (Schmidt et al., 1987); *Arabidopsis*; (Marks et al., 1991; Koncz et al., 1990); and *Antirrhinum* (Sommer et al., 1990). Gene knockouts can be made for the production of genetically engineered bacterium. "Knocking out" a gene is to be construed broadly to include reducing or eliminating the production of the encoded gene product. Thus, a gene knockout can, for example, by made by site directed mutation, insertional mutagenesis, frameshift mutation, or deletion of all or part of the gene or regulatory regions controlling expression of the gene.

Transposable genetic elements are DNA sequences that can move (transpose) from one place to another in the genome of a cell. The first transposable elements to be recognized were the Activator/Dissociation elements of *Zea mays*. Since then, they have been identified in a wide range of organisms, both prokaryotic and eukaryotic.

Transposable elements in the genome are characterized by being flanked by direct repeats of a short sequence of DNA that has been duplicated during transposition and is called a target site duplication. Virtually all transposable elements whatever their type, and mechanism of transposition, make such duplications at the site of their insertion. In some cases the number of bases duplicated is constant, in other cases it may vary with each transposition event. Most transposable elements have inverted repeat sequences at their termini. These terminal inverted repeats may be anything from a few bases to a few hundred bases long and in many cases they are known to be necessary for transposition.

Prokaryotic transposable elements have been most studied in *E. coli* and Gram-negative bacteria, but also are present in Gram-positive bacteria. They are generally termed insertion sequences if they are less than about 2 kbp long, or transposons if they are longer. Bacteriophages such as mu and D108, which replicate by transposition, make up a third type of transposable element. Elements of each type encode at least one polypeptide, a transposase, required for their own transposition. Transposons often further include genes coding for function unrelated to transposition, for example, antibiotic resistance genes.

Transposons can be divided into two classes according to their structure. First, compound or composite transposons have copies of an insertion sequence element at each end, usually in an inverted orientation. These transposons require transposases encoded by one of their terminal IS elements. The second class of transposon have terminal repeats of about 30 base pairs and do not contain sequences from IS elements.

Transposition usually is either conservative or replicative, although in some cases it can be both. In replicative transposition, one copy of the transposing element remains at the donor site, and another is inserted at the target site. In conservative transposition, the transposing element is excised from one site and inserted at another.

Elements that transpose via an RNA intermediate often are referred to as retrotransposons, and their most characteristic feature is that they encode polypeptides that are believed to have reverse transcriptase activity. There are two types of retrotransposon. Some resemble the integrated proviral DNA of a retrovirus in that they have long direct repeat sequences, long terminal repeats (LTRs), at each end. The similarity between these retrotransposons and proviruses extends to their coding capacity. They contain sequences related to the gag and pol genes of a retrovirus, suggesting that they transpose by a mechanism related to a retroviral life cycle. Retrotransposons of the second type have no terminal repeats. They also code for gag- and pol-like polypeptides and transpose by reverse transcription of RNA intermediates, but do so by a mechanism that differs from that or retrovirus-like elements. Transposition by reverse transcription is a replicative process and does not require excision of an element from a donor site.

Transposable elements are an important source of spontaneous mutations, and have influenced the ways in which genes and genomes have evolved. They can inactivate genes by inserting within them, and can cause gross chromosomal rearrangements either directly, through the activity of their transposases, or indirectly, as a result of recombination between copies of an element scattered around the genome. Transposable elements that excise often do so imprecisely and may produce alleles coding for altered gene products if the number of bases added or deleted is a multiple of three.

Transposable elements themselves may evolve in unusual ways. If they were inherited like other DNA sequences, then copies of an element in one species would be more like copies in closely related species than copies in more distant species. This is not always the case, suggesting that transposable elements are occasionally transmitted horizontally from one species to another.

ii. Chemical Mutagenesis

Chemical mutagenesis offers certain advantages, such as the ability to find a full range of mutant alleles with degrees of phenotypic severity, and is facile and inexpensive to perform. The majority of chemical carcinogens produce mutations in DNA. Benzo[a]pyrene, N-acetoxy-2-acetyl aminofluorene and aflotoxin B1 cause GC to TA transversions in bacteria and mammalian cells. Benzo[a]pyrene also can produce base substitutions such as AT to TA. N-nitroso compounds produce GC to AT transitions. Alkylation of the O4 position of thymine induced by exposure to n-nitrosoureas results in TA to CG transitions.

A high correlation between mutagenicity and carcinogenity is the underlying assumption behind the Ames test (McCann et al., 1975), which speedily assays for mutants in a bacterial system, together with an added rat liver homogenate, which contains the microsomal cytochrome P450, to provide the metabolic activation of the mutagens where needed.

In vertebrates, several carcinogens have been found to produce mutation in the ras proto-oncogene. N-nitroso-N-methyl urea induces mammary, prostate and other carcinomas in rats with the majority of the tumors showing a G to A transition at the second position in codon 12 of the Ha-ras oncogene. Benzo[a]pyrene-induced skin tumors contain A to T transformation in the second codon of the Ha-ras gene.

iii. Radiation Mutagenesis

The integrity of biological molecules is degraded by the ionizing radiation. Adsorption of the incident energy leads to the formation of ions and free radicals, and breakage of some covalent bonds. Susceptibility to radiation damage appears quite variable between molecules, and between different crystalline forms of the same molecule. It depends on the total accumulated dose, and also on the dose rate (as once free radicals are present, the molecular damage they cause depends on their natural diffusion rate and thus upon real time). Damage is reduced and controlled by making the sample as cold as possible.

Ionizing radiation causes DNA damage and cell killing, generally proportional to the dose rate. Ionizing radiation has been postulated to induce multiple biological effects by direct interaction with DNA, or through the formation of free radical species leading to DNA damage (Hall, 1988). These effects include gene mutations, malignant transformation, and cell killing. Although ionizing radiation has been demonstrated to induce expression of certain DNA repair genes in some prokaryotic and lower eukaryotic cells, little is known about the effects of ionizing radiation on the regulation of mammalian gene expression (Borek, 1985). Several studies have described changes in the pattern of protein synthesis observed after irradiation of mammalian cells. For example, ionizing radiation treatment of human malignant melanoma cells is associated with induction of several unidentified proteins (Boothman et al., 1989). Synthesis of cyclin and co-regulated polypeptides is suppressed by ionizing radiation in rat REF52 cells, but not in oncogene-transformed REF52 cell lines (Lambert and Borek, 1988). Other studies have demonstrated that certain growth factors or cytokines may be involved in x-ray-induced DNA damage. In this regard, platelet-derived growth factor is released from endothelial cells after irradiation (Witte, et al., 1989).

"Ionizing radiation" includes radiation comprising particles or photons that have sufficient energy or can produce sufficient energy via nuclear interactions to produce ionization (gain or loss of electrons). An exemplary and preferred ionizing radiation is an x-radiation. The amount of ionizing radiation needed in a given cell generally depends upon the nature of that cell. Typically, an effective expression-inducing dose is less than a dose of ionizing radiation that causes cell damage or death directly. Means for determining an effective amount of radiation are well known in the art.

iv. In Vitro Scanning Mutagenesis

Random mutagenesis also may be introduced using error prone PCR (Cadwell and Joyce, 1992). The rate of mutagenesis may be increased by performing PCR in multiple tubes with dilutions of templates.

One particularly useful mutagenesis technique is alanine scanning mutagenesis in which a number of residues are substituted individually with the amino acid alanine so that the effects of losing side-chain interactions can be determined, while minimizing the risk of large-scale perturbations in protein conformation (Cunningham et al., 1989).

In recent years, techniques for estimating the equilibrium constant for ligand binding using minuscule amounts of protein have been developed (Blackburn et al., 1991; U.S. Pat. Nos. 5,221,605 and 5,238,808). The ability to perform functional assays with small amounts of material can be exploited to develop highly efficient, in vitro methodologies for the saturation mutagenesis of antibodies. Because of the high efficiency with which all 19 amino acid substitutions can be generated and analyzed in this way, it is now possible to perform saturation mutagenesis on numerous residues of interest, a process that can be described as in vitro scanning saturation mutagenesis (Burks et al., 1997).

In vitro scanning saturation mutagenesis provides a rapid method for obtaining a large amount of structure-function information including: (i) identification of residues that modulate ligand binding specificity, (ii) a better understanding of ligand binding based on the identification of those amino acids that retain activity and those that abolish activity at a given location, (iii) an evaluation of the overall plasticity of an active site or protein subdomain, (iv) identification of amino acid substitutions that result in increased binding.

v. Random Mutagenesis by Fragmentation and Reassembly

A method for generating libraries of displayed polypeptides is described in U.S. Pat. No. 5,380,721. The method comprises obtaining polynucleotide library members, pooling and fragmenting the polynucleotides, and reforming fragments therefrom, performing PCR amplification, thereby homologously recombining the fragments to form a shuffled pool of recombined polynucleotides.

D. Monitoring Metabolic Flux

Metabolic flux, the rate at which material is processed through a metabolic pathway, is a fundamental metric of cellular metabolism. Measurements of metabolic fluxes to, for example, the fatty acid biosynthesis pathway vs. the citric acid cycle, help to determine the relative importance of particular pathways, and provide key quantitative data that are essential for bioreaction network analysis and metabolic engineering (Fernie et al., 2005; Klapa et al., 2003; Sauer, 2004).

Carbohydrate metabolism is central to the physiology of organisms as carbohydrates provide the precursor metabolites to most other pathways including the fatty acid biosynthesis pathway and are a main energy source (White, 2000). Cyanobacteria such as *Synechocystis* sp. PCC 6803 have a particularly complex central metabolic pathway as they have genes for glucose degradation by both glycolysis and the pentose phosphate pathway (Nakamura et al., 1998), and perform $CO_2$ fixation via the Calvin-Benson-Bassham cycle that has many steps in common with the pentose phosphate pathway.

Global metabolic fluxes through central carbohydrate metabolism pathways in heterotrophic (in dark with 5 mM glucose) and photomixotrophic (in light with 5 mM glucose)

cultures of *Synechocystis* sp. PCC 6803 have been determined by following isotope distributions in stable end products (Yang et al., 2002a; Yang et al., 2002b; Yang et al., 2002c). A stable-isotope-labeled substrate is added, and the final isotopic enrichment in the intracellular metabolite pools is deduced from the labeling patterns of amino acids, which are detectable by mass spectrometry (MS) or nuclear magnetic resonance (NMR) spectroscopy. The resulting data provides a large amount of information that is used to calculate the intracellular fluxes. Although this analysis allows the approximation of many rates simultaneously, such analysis has several drawbacks: (i) It is used on steady-state cultures, and no dynamic flux rates are obtained; (ii) the analysis requires all analytes and pathways/reactions to be exactly known; and (iii) data processing is complex and requires assumptions that may not be valid under all experimental conditions. This may lead to artifacts, particularly if complex and intertwined pathways are modeled (van Winden et al., 2005).

In view of these potential drawbacks, a simple and objective method to analyze parts of the central carbohydrate metabolism is desired. Therefore, the inventor developed an approach where individual reactions can be monitored more directly and as a function of time. Intracellular central metabolic metabolites, such as sugar phosphates, may be monitored with a wide range of techniques, e.g., enzymatic assays, HPLC (Bhattacharya et al., 1995; Groussac et al., 2000), CE/MS (Soga et al., 2002), GC/MS (Fiehn et al., 2000; Roessner et al., 2000) and LC/MS (Buchholz et al., 2001; Buchholz et al., 2002; Mashego et al., 2004; van Dam et al., 2002). Buchholz et al. (2001) have developed a method for quantification of intracellular concentrations of glycolytic intermediates in *Escherichia coli* K12 using LC-ESI-MS. By this method it is possible to identify and quantify different sugar phosphates in parallel in a small sample volume. For analysis of metabolic fluxes, the most decisive advantage of MS detection methods is that they enable $^{13}C$ tracing, by which labeling patterns of intracellular metabolites can be determined. Recently, van Winden et al. (2005) have directly measured unlabeled and $^{13}C$-labeled central metabolic intermediates from *E. coli* cultures by LC/MS.

The inventors used a combination of LC/MS and 13C tracing methods to directly measure enrichment of $^{13}C$-labeled metabolic intermediates as a function of time. This method enabled the inventors to gain detailed information about the metabolic flux network and the dynamics of metabolic fluxes as it allows an in-depth analysis of the interconversion rates between sugar phosphates under different growth conditions.

D. Recovery of Desired Products

In some instances, it is desired to recover the expressed desired product. Once expressed, the desired products can be purified according to standard procedures of the art, including ammonium sulfate precipitation, affinity columns, column chromatography, gel electrophoresis, solvent extraction, molecular sieving and the like (see, generally, R. Scopes, (1982) Protein Purification, Springer-Verlag, N.Y.; Deutscher (1990) Methods in Enzymology Vol. 182: Guide to Protein Purification., Academic Press, Inc. N.Y.).

In certain aspects, an initial step in recovery of the desired product can include lysing or fracturing the cells. Possible lysing methods known to those of skill in the art can be used and include thermal treatments, sonification, mechanical abrasion, pressurization and sudden depressurization, abrasion and fracture as aided by addition of inert media, electroporation, and alkali or acid treatment. Once fractured, the cell lysate can be subjected to direct solvent or supercritical $CO_2$ extraction for lipid-based products (see, e.g., Serrano-Carreon et al. (2002); Nobre et al. (2006); Topal et al. (2006), all of which are incorporated by reference). Alternatively, the desired products can be isolated by two-phase partitioning systems (see, e.g., Rito-Palomares (2004); Cisneros et al. (2004); Serrano-Carreon et al. (2002), all of which are incorporated by reference).

E. Assays for Determining Altered Expression

It is contemplated that the photoautotrophic bacteria of the present invention can display an altered level of a desired product by using the methods described throughout this specification. "Altered" or "modified" includes expression in different levels relative to the natural expression of the desired product in the bacteria. The genes of interest may be modified in their sequence or level of expression, and/or deleted and/or introduced from foreign sources. This can lead to modulated production of the corresponding desired gene product (e.g., protein or enzyme) and/or modulation of the pathways related to such gene products (e.g., increasing or over-expressing a gene of interest to obtain an increased amount of a corresponding gene product and/or components of metabolic pathways associated with the gene product). Such alteration may be assessed by a variety of methods, including radio-labeling, fluorescent labeling, staining, mass spectrometry, enzyme activity measurements and/or protein purification. Simple and direct methods include those involving SDS/PAGE and protein staining or western blotting, followed by quantitative analyses, such as densitometric scanning of the resultant gel or blot. A specific increase in the level of the desired product in comparison to the level in natural bacterial is indicative of overexpression, as is a relative abundance of the specific desired product in relation to other proteins produced by the bacterial cell and, e.g., visible on a gel.

F. Growth/Culture Conditions for the Photoautotrophic Bacteria

Large-scale production of the desired products via growing the photoautotrophic bacteria of the present invention can performed by both batch or continuous culture methodologies. A classical batch culturing method is a closed system where the composition of the media is set at the beginning of the culture and not subject to artificial alterations during the culturing process. Thus, at the beginning of the culturing process the media are inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems. A variation on the standard batch system is the Fed-Batch system which includes a typical batch system with the exception that the substrate is added in increments as the culture progresses. Fed-Batch systems are useful when catabolite repression is apt to inhibit the metabolism of the cells and where it is desirable to have limited amounts of substrate in the media. Batch and Fed-Batch culturing methods are common and well known in the art and examples may be found in Thomas D. Brock in Biotechnology: A Textbook of Industrial Microbiology, Second Edition (1989) Sinauer Associates, Inc., Sunderland, Mass., or Deshpande, Mukund V., Appl. Biochem. Biotechnol., 36, 227, (1992), incorporated by reference.

Alternatively, continuous cultures are an open system where a defined culture medium is added continuously to a bioreactor and an equal amount of conditioned medium is removed simultaneously for processing. Continuous cultures generally maintain the cells at a constant high liquid phase density where cells are primarily in log phase growth. Alternatively continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

G. System for Growing and Processing the Photoautotrophic Bacteria

In certain aspects of the present invention, the photoautotrophic bacteria can be grown in large scale production systems. One such system is described in U.S. Provisional Patent Application No. 60/862,366, filed on or about Oct. 20, 2006, titled "System and Method for Growing Cells," by Willem F. J. Vermaas and Bruce E. Rittmann and PCT Application No. PCT/US2007/081994, entitled "System and Method for Growing Photosynthetic Cells", filed on or about Oct. 19, 2007, by Willem F. J. Vermaas and Bruce E. Rittmann, incorporated herein by reference.

H. Processing the Desired Products

In certain aspects, a desired product (e.g., a lipid, a carotenoid, a carbohydrate, or cyanophycin) can be obtained by: (i) obtaining a modified photoautotrophic bacterium in which a level of expression of one or more genes of interest has been altered, wherein the altered expression of the one or more genes increase production of the one or more desired products relative to an amount of the one or more desired product produced by a photoautotrophic bacterium in which a level of expression of the one or more genes has not been altered; (ii) growing the photoautotrophic bacterium under suitable conditions to produce the desired product; and (iii) isolating the desired product. The isolated product can be further processed into several different products. Non-limiting examples include biofuels, a bio-plastics, an animal feed additives, and organic fertilizers.

With respect to biofuels, lipids and carbohydrates produced by methods of the present invention can be further processed into biodiesel and biogases. Biodiesel is a liquid fuel source that can be used in a similar manner as petroleum based diesel fuel. Bio-diesel production can be synthesized by replacing glycerol with a short chain alcohol such as methanol or ethanol in a step known as transesterification. The transesterification process typically involves mixing at room temperature methanol (50% excess) with NaOH (100% excess), then mixing vigorously with the lipid/oil and letting the glycerol settle (about 15% of the biodiesel mix). The supernatant is biodiesel and contains a mixture of methylated fatty acids and methanol, the NaOH catalyst remaining dissolved in the glycerol fraction. Industrially, the esters can be sent to the clean-up or purification process which consists of water washing, vacuum drying, and filtration. Transesterification can be processed using methanol, ethanol, isopropyl alcohol, or butanol. The catalyst can be sodium or potassium hydroxide. It has been shown that the methanol/oil molar ratio influences largely the efficiency of the reaction and has important implications for the optimal size of methyl ester plants. Alternative methods include the supercritical fluid methanol method or the use of an ultrasonic reactor and other methods known to those of ordinary skill in the art (see, e.g., Aresta (2005); Saka et al. (2006), which are incorporated by reference).

Biogases can be prepared with the carbohydrates obtained by methods of the present invention by methods known to those of skill in the art. For instance, non-limiting examples of such methods and protocols are explained in Gong et al. (1999). By way of example only, glucose oxidation is used for formation of reducing equivalents, which can be used for reduction of protons to hydrogen in cyanobacteria by means of hydrogenase (Nandi et al. (1998) which is incorporated by reference). Another non-limiting example includes photobiohydrogen production (Prince et al. (2005) which is incorporated by reference).

Bioplastics can be prepared with the carbohydrates obtained by methods of the present invention by methods known to those of skill in the art. For instance, PHA levels in cyanobacteria (PHB) are increased several-fold upon transfer to reducing conditions, with addition of glucose leading to a further increase. Non-limiting examples of bioplastic production are described in Taroncher et al. (2000). Additionally, although cyanobacteria do not naturally make polylactic acid, they can be modified to do so with the right enzymes that follow principles developed for *E. coli*. (Zhou et al. (2005) which is incorporated by reference).

Alternatively or in addition to processing the desired products, the modified photoautotrophic bacterium of the present invention can be used to fix the carbon dioxide that is supplied to the bacteria. This can be advantageous, for example, in reducing or removing the carbon dioxide from the carbon dioxide source (e.g., reducing the amount of carbon dioxide in flue gas). A non-limiting system that can be used to perform this is described in the U.S. Provisional Patent Application No. 60/862,366, filed on or about Oct. 20, 2006, titled "System and Method for Growing Cells," by Willem F. J. Vermaas and Bruce E. Rittmann and PCT Application No. PCT/US2007/081994, entitled "System and Method for Growing Photosynthetic Cells", filed on or about Oct. 19, 2007, by Willem F. J. Vermaas and Bruce E. Rittmann, incorporated herein by reference.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Figure 14:
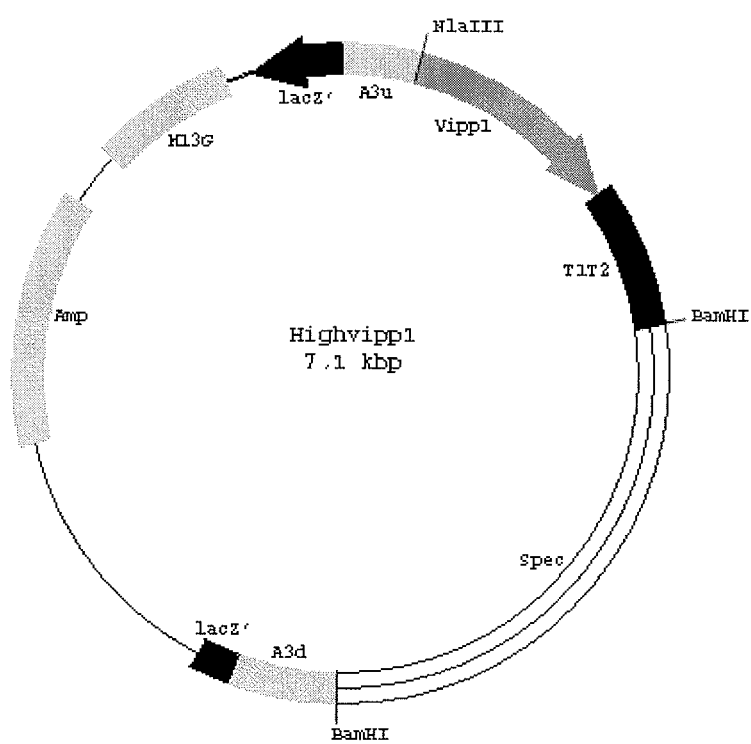
FIG. 14. Plasmid map of the construct used to generate the VIPP-1 overexpression mutant of *Synechocystis*. This copy of the VIPP-1 gene was inserted under the psbA3 promoter.

A Modified *Synechocystis* sp. PCC 6803 Cyanobacterium for Increasing the Lipid Content The cyanobacterium *Synechocystis* sp. PCC 6803 was modified to overexpress the VIPP1 gene sll0617. To achieve high expression level of vipp1 gene (sll0617), it was cloned under the constitutive native promoter of *Synechocystis* psbA3 gene (sll1867). The vipp1 gene was cloned in between the upper (287 bp) and down stream (394 bp) regions of the native psbA3 gene in a spectinomycin analog of pA3lhcgA3 plasmid (He et al. 1999); the resulting plasmid was named Highvipp1 and is schematically presented in FIG. 14. The sequence for the vipp1 (sll0617) gene was obtained from CyanoBase and two primers were constructed to amplify the *Synechocystis* genomic 837-bp fragment that corresponds to 804 bp of the vipp1 gene, 15 bp upstream from the vipp1 gene start codon, and 18 bp downstream from the vipp1 gene stop codon. The sequences for the primers were 5'-GAG GAT AAG TAA GtC ATG aGA TTA TTT GAC and 5'-CTG GCT GAG TTA Atg CAt TTA CAG ATT ATT TAA CC. The lower case letters indicate the nucleotide base modification for the introduction of unique restriction sites of BspHI and NsiI for the first and second primer, respectively. The amplified vipp1 fragment and the spectinomycin resistance cassette from pA3lhcgA3 were digested with (BspHI, NsiI) and (NcoI, PstI), respectively. After ligation, *E. coli* transformation was performed by electroporation, and after transformation cells were plated at room temperature; *E. coli* transformants with the full length vipp1 gene, as indicated by plasmid sequencing, was successful only when cells were incubated at room temperature (rather than 37° C.) at all steps subsequent to electroporation.

Transformation of *Synechocystis* sp. PCC 6803

*Synechocystis* was transformed with the Highvipp1 plasmid (FIG. 14) according to (Vermaas et al. 1987). *Synechocystis* transformants carrying the chimeric vipp1 gene were selected for through spectinomycin resistance, and increasing the spectinomycin concentration upon subsequent restreaks of transformants was utilized to obtain full segregation in single colonies. To verify genomic integration of the full length vipp1 gene at the desired site of the *Synechocystis* genome, polymerase chain reaction was used to amplify the fragment between the terminal upstream sequence of psbA3 gene and the beginning of the T1T2 terminator sequence. The terminal sequence of the upstream psbA3 gene was 5'-GAC AAA TAC ATA AGG AAT TAT AAC c and the sequence of the primer that mapped to the beginning of the T1T2 terminator sequence was 5'-GCC AAA ACA GCC AAG CTT GGC. The first primer was used to do the forward DNA sequencing and the latter primer for the reverse DNA sequencing of the amplified chimeric vipp1 gene.

Figure 8:
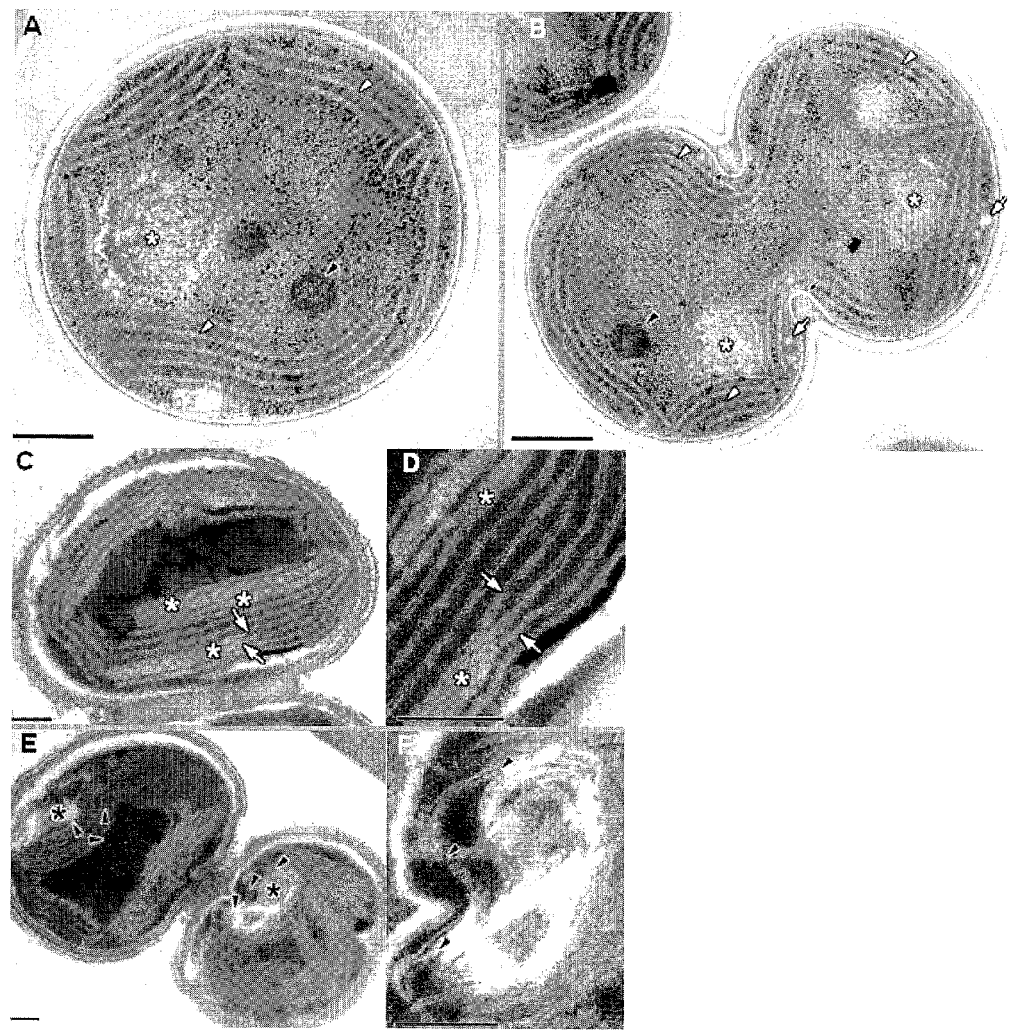
FIG. 8: Transmission electron micrographs of wild type non-dividing FIG. 8A and dividing FIG. 8B *Synechocystis* sp. PCC 6803 cyanobacterial cells. At both stages, the mostly peripheral arrays of thylakoid membrane pairs (white arrowheads) converge at sites adjacent to the cytoplasmic membrane. Carboxysomes (black arrowheads), PHA granule (asterisks), lipid bodies (white arrows) and septum (black arrow) are noted.

As explained below and shown in Table 1 and FIG. 8, overexpression of this gene increased the lipid content in the *Synechocystis* sp. PCC 6803 cyanobacterium to almost 50% of the dry weight. The sll0617 gene was placed under the psbA3 promoter. *Synechocystis* cells were grown at 50 micromol photons $m^{-2} s^{-1}$ at 30° C. Lipid extraction was performed via a standard method (see, e.g., Tasaka et al. 1996).

TABLE 1

Doubling time (h) and lipid % of dry weight, fresh water, unstressed conditions. Strains are wild type unless indicated otherwise.

| Organism | doubling time (h) | lipid (% of DW) | determination method | comment | reference |
|---|---|---|---|---|---|
| Cyanobacteria | | | | | |
| "Anacystis nidulans" (*Synechococcus*) | 14 | 7 | from fatty acids[1] | | [1] |
| *Synechocystis* sp. PCC 6803 | 12 | 20 | gravimetric[2] | | [2] |
| *Synechocystis* sp. PCC 6803, Sll0617 overexpresser | 13 | 47 | gravimetric[2] | | [2] |

TABLE 1-continued

Doubling time (h) and lipid % of dry weight, fresh water, unstressed conditions. Strains are wild type unless indicated otherwise.

| Organism | doubling time (h) | lipid (% of DW) | determination method | comment | reference |
|---|---|---|---|---|---|
| Green algae | | | | | |
| *Ankistrodesmus* sp. | 24 | 25 | gravimetric[2] | +0.1 M NaCl | [3] |
| *Botryococcus braunii* | 72 | 45 | gravimetric[2] | | [3] |
| *Nannochloris* sp. | 20 | 21 | gravimetric[2] | +0.1 M NaCl | [3] |

[1] likely to underestimate due to loss during process
[2] likely to overestimate due to co-isolating impurities
[1] Sato et al., BBA 572 (1979) 19-28
[2] Vermaas lab, unpublished
[3] Ben-Amotz et al., J. Phycol. 21 (1985) 72-81

Example 2

Dynamic Analysis of Metabolic Fluxes Through the Central Carbohydrate Metabolism Pathways of *Synechocystis* Sp. PCC 6803, and Enhancement of Fatty Acid Biosynthesis by accABCD Overexpression 1. Materials and Methods Chemicals.

The chemicals used as standards (glucose-6-phosphate (G6P), fructose-6-phosphate (F6P), fructose-1,6-bisphosphate (FBP), glyceraldehyde-3-phosphate (GAP), dihydroxyacetone phosphate (DHAP), 3-phosphoglycerate (3PG), phosphoenolpyruvate (PEP), 6-phosphogluconate (6PG), ribose-5-phosphate (R5P), ribulose-5-phosphate (Ru5P), ribulose-1,5-bisphosphate (RuBP), and erythrose-4-phosphate (E4P)) were purchased from Sigma (St. Louis, Mo.). Uniformly $^{13}$C-labeled D-glucose (U-$^{13}C_6$-D-glucose) was from Cambridge Isotope Laboratories, Inc. (Andover, Mass.). Milli-Q-grade water (Millipore, Van Nuys, Calif.) was used for all solutions.

Growth Conditions and $^{13}$C-Glucose Labeling.

*Synechocystis* sp. strain PCC 6803 wild type and mutants lacking phosphofructokinase and/or glucose-6-phosphate dehydrogenase were cultivated in air at 30° C. in BG-11 buffered with 5 mM TES [N-tris(hydroxymethyl)methyl-2-aminoethanesulfonic acid]-NaOH (pH 8.0). For photomixotrophic and photoheterotrophic growth, the growth medium was supplemented with 5 mM glucose. For photoheterotrophic growth, 25 µM of the herbicide atrazine that blocks electron transport through PS II was added to the medium. Cultures were illuminated with white light at an intensity of 50 µmol photons $m^{-2} s^{-1}$ and were shaken at an agitation speed of 120 rpm. Growth of the cultures was monitored by measuring the optical density at 730 nm with a Shimadzu UV-160 spectrophotometer.

For $^{13}$C labeling, cells in the late-exponential growth phase ($OD_{730}$=1.0) were diluted 40-fold in BG-11 medium supplemented with 1 mM glucose. When the cell density reached $OD_{730}$=0.5, 0.5 mM $^{13}$C glucose or 5 mM $^{13}$C NaHCO$_3$ (labeled bicarbonate was added together with 0.5 mM unlabeled glucose) were added to the culture, and the culture was continued to incubate under usual growth conditions. Samples were taken at different times after addition of labeled glucose or bicarbonate at time 0.

Sample Preparation.

100 ml aliquots were removed from the labeled *Synechocystis* sp. PCC 6803 ($OD_{730}$=0.5) cultures at specific times after addition of label, and culture aliquots were harvested rapidly by filtration through a glass microfiber filter (FG/B, Whatman) and washed with 35 ml water to remove residual medium. The filter with cells was put immediately into 20 ml cold (−40° C.) methanol, and was incubated under these conditions for 30 min to quench reactions. The methanol/filter/cells mixture was then incubated at 70° C. for 6 min for metabolite extraction. After the filter was discarded, methanol was evaporated under $N_2$ at 4° C. Finally, the remaining powder was dissolved in 0.25 ml water. After ultracentrifugation in an Optima TLX 120 ultracentrifuge (Beckman) at 280,000 g (80,000 rpm) for 1 hour, the clear supernatant was transferred to a new tube and stored at −70° C.

HPLC Separation.

HPLC was performed using a porous graphitic carbon Hypercarb column (100×2.1 mm, 5 mm, Thermo-Electronic, Bellefonte, Pa.). Additionally, a Hypercarb guard column (10×2.1 mm) was employed to protect the main column. A binary gradient at a flow rate of 0.125 ml $min^{-1}$ was applied using a Beckman HPLC system. The injection volume was 50 µl. Solvent A was 12 mM aqueous ammonium acetate, and solvent B was water. The gradient applied for separation was an increase in Solvent B linearly from 60% to 100% in the first 20 min. This level was held for 5 min before being reduced again to 60% B during the next 2 min. This level was held for 10 min to permit re-equilibration of the column.

A postcolumn T-splitter was used to pump methanol to join the HPLC eluate at a flow rate of 0.125 ml $min^{-1}$ and the mixture was then led into the mass spectrometer via the ESI interface.

Mass Spectrometry.

MS analysis was performed using an ABI 365 triple-quadrupole mass spectrometer (Applied Biosystems/MDS Sciex). Nitrogen was used both as sheath gas and collision gas. Data acquisition and analysis were conducted using Analyst software (Applied Biosystems/MDS Sciex).

Optimum parameters for MS experiments were determined in full scan mode by direct injection of different standards with a syringe pump at a rate of 10 µl $min^{-1}$. The tune parameters from the tuning with standard G6P (5 µM G6P in methanol:12 mM ammonium acetate (50:50%, v/v)) were used for MS and MS/MS detection. The following ESI parameters were employed: temperature of heated capillary: 300° C.; electrospray capillary voltage: 4.2 kV; curtain gas: 8 psi; focus voltage: 100 V. All other parameters were determined by automatic tune.

The Q1 Multiple Ion mode was used to quantify the concentration of the intermediates and their isotopomers. The MS/MS mode was used to identify or confirm the identity of chemicals.

Identification and Quantification of Metabolites.

The metabolites in samples were identified according to their retention time, m/z, specific fragmentation patterns, and if needed by spiking the extracts with metabolite standards at a concentration of 10-50 µM. $^{13}C$-labeling experiments further confirmed the identification of metabolites. Quantification of metabolites was accomplished via the [M-H]⁻ ion by applying the standard addition method (Skoog and Leary, 1992). A standard solution containing only one analyte at a known concentration was prepared. By spiking cell extracts with increasing amounts of this standard solution, linear regression plots of peak area versus concentration were obtained.

$^{13}C$ Distribution Analysis.

$^{13}C$-labeled samples collected from photomixotrophic and photoheterotrophic cultures were collected at 0, 0.33, 1.5, 5, 20 and 60 minutes after addition of $^{13}C$ label. Cell extracts were separated by HPLC and measured by MS in MIM mode, which could follow different mass isotopomers of various intermediates at the same time. The content and distribution of different mass isotopomers was calculated from their peak areas.

2. Results

Separation and Identification of Metabolic Intermediates by LC/MS.

Separation of metabolic intermediates by HPLC was essential not only for improvement of the sensitivity of the MS detection, but also for the identification and quantitation of the intermediates. The Hypercarb HPLC column was suitable for separation of sugar phosphates and related compounds that had a wide range of retention times (FIG. 1A). In combination with mass separation by MS, all available relevant standards of carbohydrate metabolic intermediates were clearly separated and 20 µM solutions were easily detected. Some standards, such as S7P and SBP, were not commercially available, although these compounds could be identified in cell extracts based on their mass (FIG. 1B).

As shown in FIG. 1A, the retention time of different standards ranged from 5 to 25 minutes. Even though some standards, such as R5P (mass 229, first peak) and G6P (mass 259, first peak) overlapped with each other on LC, they were distinguished by MS due to their difference in mass. Conversely, the isomers with mass 169 (GAP, peak 1 (shortest elution time); DHAP, peak 2 (longer elution time)), 229 (R5P, peak 1; RuSP, peak 2) and 259 (G6P, peak 1; F6P, peak 2) were separated by LC, but not by MS. The clear separation between the compounds by LC and/or MS enabled quantification of these central metabolism intermediates.

Now that standards had been shown to be detectable at µM concentrations by this method, *Synechocystis* extracts were analyzed. To maximize MS sensitivity, particulates should be removed from the sample to the extent possible, so that ion suppression is minimized. For this reason, samples were spun at 80,000 rpm (280,000 g) in an ultracentrifuge for 60 min before LC/MS analysis. As expected, when cell extracts were analyzed by LC/MS in scan mode, many peaks were found corresponding to the large number of different metabolites in the cell (data not shown). Here, the inventors focused entirely on central carbohydrate metabolism intermediates. FIG. 1B shows sugar phosphates measured in MIM MS mode, where only selected m/z values were monitored. The identified peaks included those corresponding to mass 167 (PEP), 185 (2PG, peak 1; 3PG, peak 2), 229 (R5P, peak 1; Ru5P, peak 2), 259 (G6P, peak 1; F6P, peak 2), 289 (S7P), 309 (RuBP) and 369 (SBP); "peak 1" is the one with the shorter elution time relative to peak 2. No peak was found when scanning for m/z 169, 199, 275 and 339 (FIG. 1B) although standards gave a large signal (FIG. 1A). This, together with the observation that standards did not degrade significantly during the extraction procedure (data not shown), indicate that GAP (mass 167), DHAP (mass 167), E4P (mass 199), 6PG (mass 275) and FBP (mass 339) did not accumulate in the cell.

Figure 2:
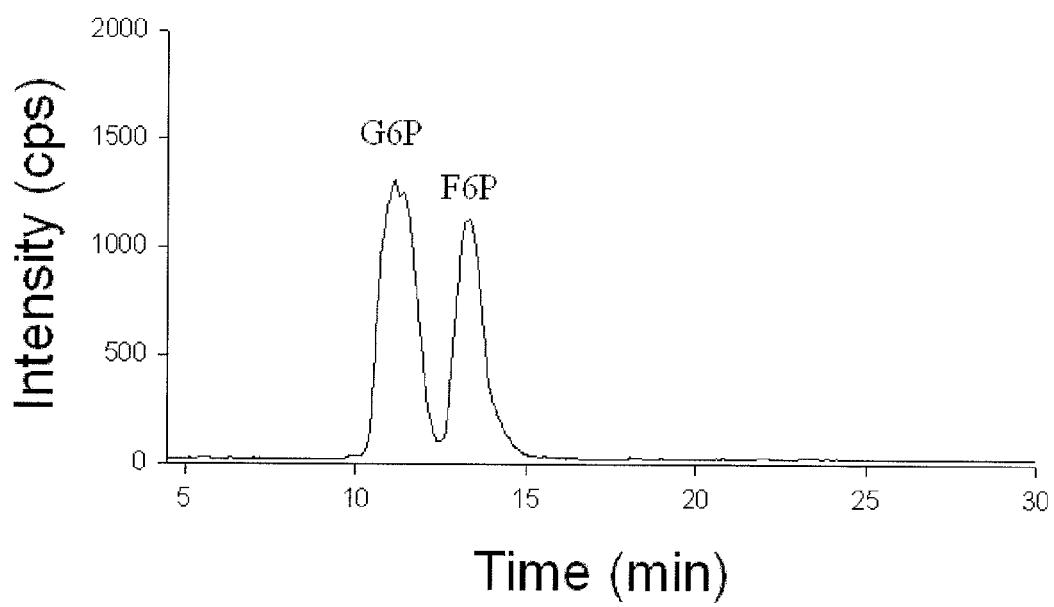
FIG. 2. Example of verification of LC/MS peaks by MS/MS. The 259 m/z peak was selected upon the first MS, and the signal presented in this figure is the intensity of the 97 m/z (phosphate) signal after the second MS. The LC elution time is plotted on the X-axis.

Samples were spiked with 20 µM standards (not shown) to allow quantification of peaks and to check for the correct identification of compounds. Moreover, the MS/MS mode was also used to verify the correct assignment of compounds. An example of the latter is provided in FIG. 2, where the peaks were obtained by selectively monitoring, in a second MS, the typical phosphate fragment (97 m/z) of molecules with a mass of 259 (the mass of the ions of G6P and F6P) in the first MS. In this mode, ions of 259 m/z go through the first quadrupole and are broken up in the collision cell; only 97 m/z fragments are selected to go through the second quadrupole and are counted by the detector. The results shown in FIG. 2 verified that the two 259 m/z peaks in FIG. 1B indeed contained phosphate groups. Other sugar phosphate peaks were also confirmed to generate a phosphate fragment in MS/MS.

Isotopomer Measurements and Quantitation in Cell Extracts.

Figure 3:
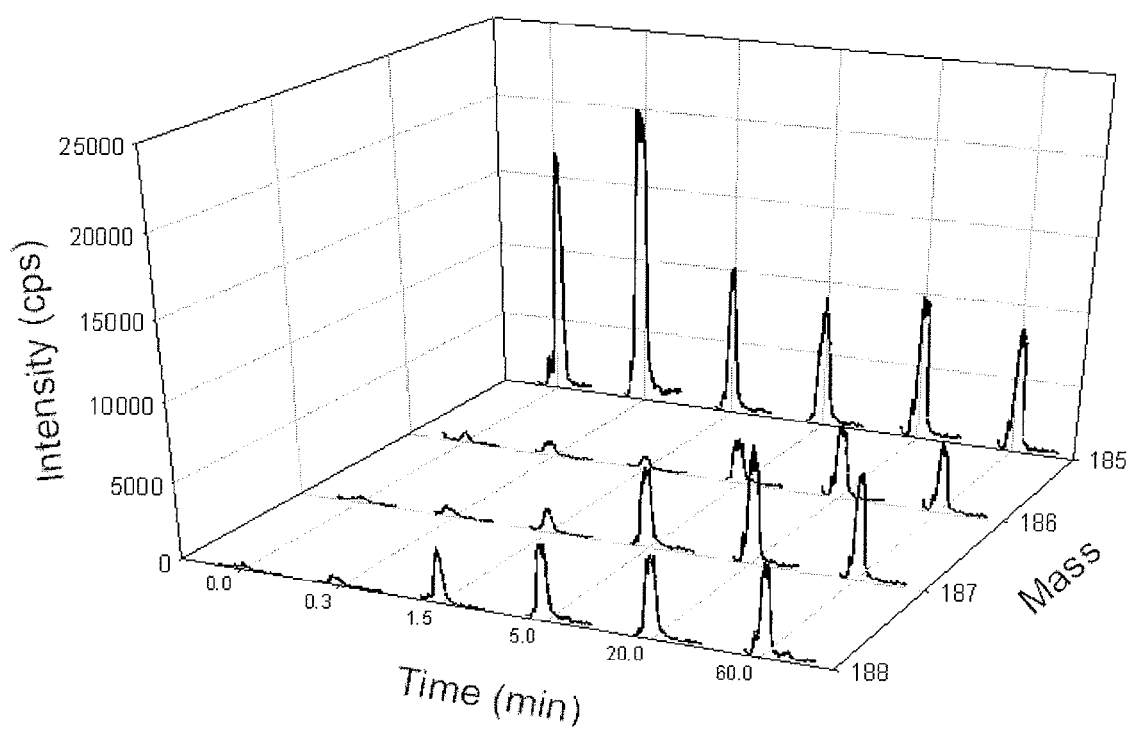
FIG. 3. Dynamic distribution of 3-phosphoglycerate (3PG) isotopomers upon $^{13}$C-glucose labeling of photomixotrophically growing *Synechocystis* culture. At time 0, 0.5 mM $^{13}$C-glucose was added. Samples were withdrawn at various times and the mass distribution of 3PG (unlabeled mass (185), mass+1, mass+2, mass+3) was analyzed.

Of the identified sugar phosphates, particularly G6P, F6P, PEP, 3PG, 2PG and S7P consistently gave significant and reproducible MS peaks upon LC/MS of *Synechocystis* extracts and were used for isotopomer distribution analysis after labeling of the cells with $^{13}$C-D-glucose or bicarbonate. As an example of isotopomer labeling over time, FIG. 3 shows the dynamics of 3PG labeling in *Synechocystis* extracts that were prepared from photomixotrophically growing cells at different times after the start of $^{13}$C-glucose labeling. At the start of $^{13}$C-glucose labeling (t=0), the great majority of 3PG molecules contained three $^{12}$C carbons (mass 185). The abundance of the mass+1 isotope at t=0 was about 3.6%, consistent with the natural abundance of $^{13}$C, while the abundance of 3PG molecules with mass 187 or 188 (carrying two or three labeled carbons) was very small. After 20 s of growth in the presence of $^{13}$C-glucose, labeled 3PG started to appear, whereas at 1.5 min, a clear 188 (three labeled carbons) 3PG peak was visible. After that, 3PG molecules with two $^{13}$C atoms started to increase and became the major labeled isotopomer. An hour after the addition of labeled glucose, the isotopomer distribution pattern of 3PG included significant amounts of all isotopomers and apparently had reached a steady state; the peaks did not change significantly in size and ratio at longer incubation times (not shown).

Figure 4:
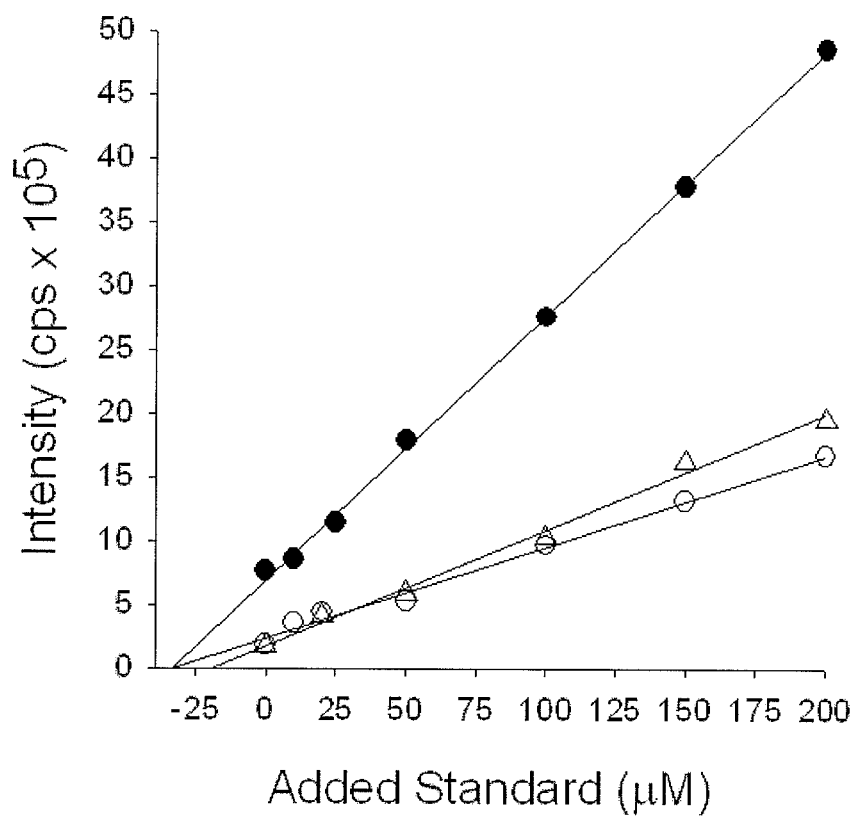
FIG. 4. Calibration of metabolite concentrations versus the area of the MS signal. Different concentrations of standards were added to the cell extract. The concentration of the corresponding metabolite in the extract is the absolute value of the intersect with the abscissa. G6P: open circles; 3PG: closed circles; PEP: open triangles.

In theory, the LC/MS peak areas of a signal should be linear with the concentration of the compound. To verify linearity in our detection range of central metabolic intermediates in *Synechocystis* cell extracts, the peak areas of the G6P, 3PG and PEP MS signals were determined after adding known concentrations of standards to the cell extract. The concentrations of G6P, 3PG and PEP in the original extract were obtained from these curves (FIG. 4), and correspond to the negative value of the abscissa. Although the S7P concentration could not be calculated in this way as the standard was unavailable, its peak areas were linearly correlated with the volume of the cell extract that was loaded.

The ratio and labeling pattern of G6P and F6P, and those of 3PG and 2PG were similar under all experimental conditions probed here, suggesting a very high rate of exchange between these isomers. To simplify data collection and processing, G6P and F6P were combined to a common pool of G6P+F6P, and 3PG and 2PG were combined to yield a common pool of 3PG+2PG.

Dynamics of the $^{13}$C-Labeling Pattern in *Synechocystis*.

The inventors compared changes in the distribution of isotopomers of G6P+F6P, 3PG+2PG, PEP and S7P in *Synechocystis* extracts as a function of the growth mode (photomixotrophic vs. photoheterotrophic) of the cells and as a function of time after the addition of $^{13}$C, in order to obtain an understanding of the central metabolic fluxes in this cyanobacterium. Even though the isotopomer distributions among the measured intermediates were fully reproducible when cells were grown in the same growth mode (photomixotrophic or photoheterotrophic), the total concentrations of these compounds that were extracted from the cells varied significantly from experiment to experiment (Table 2). The measured concentrations in the extracts were calculated back to internal concentrations in the cells using the following parameters and assumptions: (1) cultures of *Synechocystis* during exponential growth have $10^{11}$ cells per $OD_{730}$ per liter when monitoring using a Shimadzu UV-160 spectrophotometer; (2) cells have an average diameter of 2 and (3) the metabolite extraction efficiency was 100%; quantitation of the available standards added to the cold cell/methanol mixture vs. to the final extract used for MS showed that the extraction process did not cause any significant quantitative loss (data not shown). It is presently unclear what caused the fluctuations in the concentrations of metabolites in the cells; the parameter that could not be fully controlled and estimated is the efficiency with which compounds were extracted from cells in cold methanol.

TABLE 2

The intracellular metabolic intermediate concentrations of *Synechocystis* sp. PCC 6803 under photomixotrophic and photoheterotrophic growth conditions.

| | Growth condition | |
| --- | --- | --- |
| | Photomixotrophic | Photoheterotrophic |
| Compound | Concentration (μM)[a] | |
| G6P + F6P | 913 ± 500 | 1544 ± 672 |
| 3PG + 2PG | 1139 ± 715 | 1588 ± 920 |
| PEP | 376 ± 137 | 737 ± 208 |
| S7P[b] | 1 ± 0.35[b] | 2.61 ± 1.12[b] |
| R5P | 80 ± 32 | 72 ± 30 |
| RuBP | 112 ± 33 | UD[c] |
| SBP[b] | 1 ± 0.35[b] | UD |

[a]The data represent the mean of three independent experiments. Intracellular concentrations were calculated assuming a 100% extraction efficiency, and an average radius of 1 μm of the spherical cells.
[b]The relative rather than absolute concentration of S7P and SBP is provided because the pure standards were unavailable.
[c]UD: undetectable.

In any case, the concentrations of G6P+F6P, 3PG+2PG, PEP and R5P under photomixotrophic vs. photoheterotrophic growth modes were within a factor of two from each other, whereas RuBP and SBP, two compounds specific for the Calvin-Benson-Bassham cycle, were undetectable under photoheterotrophic conditions but were present under photomixotrophic conditions. The S7P level was increased by about two-fold under photoheterotrophic growth conditions.

Labeling of Photomixotrophically Grown Cultures with $^{13}$C-Glucose.

Figure 5:
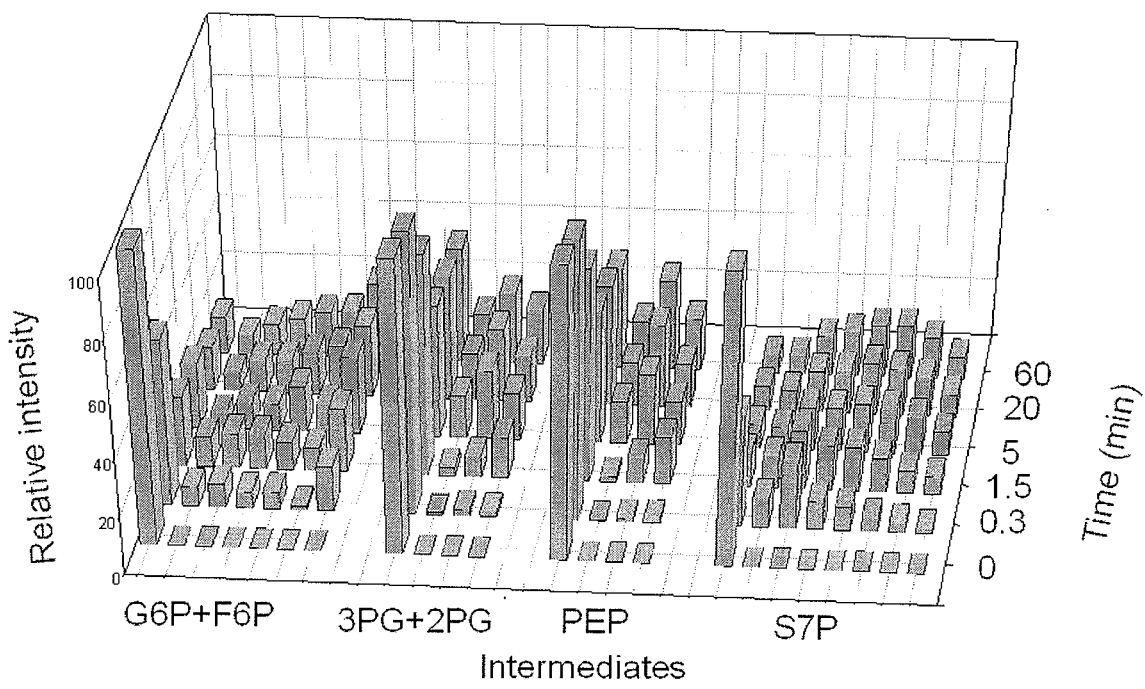
FIG. 5. Isotope distribution of hexose-6-phosphate (G6P+F6P), phosphoglycerate (3PG+2PG), phosphoenolpyruvate (PEP) and sedoheptulose-7-phosphate (S7P) pools in extracts from cells as a function of time of growth under photomixotrophic conditions after addition of labeled glucose. 0.5 mM $^{13}$C glucose was added at time 0. Isotopomers are separated on the X-axis according to mass (left to right: unlabeled mass, mass+1, mass+2, etc.). The data were the mean of three experiments. Standard deviation analysis showed that changes in relative intensity of more than 5% were significant.

In FIG. 5, isotopomer distributions in extracts from photomixotrophically grown cultures have been represented graphically as a function of time after addition of $^{13}$C-glucose. The actual data from which FIG. 5 was derived are listed in Table 3. In photomixotrophically grown cultures, labeled G6P+F6P made up about 40% of the total G6P+F6P pool just 20 s after addition of $^{13}$C-glucose, signifying very rapid uptake and conversion of glucose in *Synechocystis*. Not surprisingly, at this time point fully labeled G6P+F6P was the most abundant isotopomer (265 m/z). However, the rapid appearance of molecules in the G6P+F6P pool with masses of 1, 2, 3 or 4 more than the unlabeled mass was remarkable (each about 6% of the total pool after 20 s of labeling). The rapid appearance of mass+2, +3 and +4 peaks signify a very rapid redistribution of carbon atoms through the readily reversible transaldolase and transketolase reactions. The rapid formation of G6P+F6P molecules with one $^{13}$C atom may result either from decarboxylation of partially labeled G6P+F6P (e.g., 1,2-$^{13}C_2$ or 3,4,5,6-$^{13}C_4$ G6P+F6P) through reactions 10 and 11 followed by reformation of G6P+F6P through reactions 12 and 16, or from splitting of partially labeled G6P+F6P (e.g., 3,4,5,6-$^{13}C_4$ G6P+F6P) through reactions 3 and 4 followed by recombination with an unlabeled dihydroxyacetone 3-phosphate or glyceraldehyde 3-phosphate molecule. After 20 minutes of labeling, the peak corresponding to unlabeled G6P+F6P was reduced to about 15% of the total, indicating that there is not a major buffer or reservoir of unlabeled sugar polymers in the cell that is converted to monomers while added glucose is available.

more $^{13}$C carbons at this time point. The ratio of labeled vs. unlabeled S7P molecules at the 20 s time point was even higher than that of G6P+F6P. This indicates a very high rate of the transketolase/transaldolase reactions, as these reactions transfer label from F6P—directly or indirectly—to S7P and other compounds. Among these labeled S7P isotopomers, the most abundant one 20 s after the start of labeling contained

TABLE 3

Dynamic isotopomer distribution of hexose-6-phosphate (G6P + F6P), phosphoglycerate (3PG + 2PG), phosphoenolpyruvate (PEP), and sedoheptulose-7-phosphate (S7P) upon $^{13}$C-glucose labeling in photomixotrophically grown Synechocystis sp. PCC 6803.[a]

| | | labeling time (min) | | | | | | | | | | | |
|---|---|---|---|---|---|---|---|---|---|---|---|---|---|
| | | 0 | | 0.33 | | 1.5 | | 5 | | 20 | | 60 | |
| Compound | mass | ID[b] | SD[b] | ID | SD | ID | SD | ID | SD | ID | SD | ID | SD |
| G6P + F6P | 259 | 100 | 3.2 | 57.3 | 7.8 | 24.5 | 6.8 | 22.6 | 7.4 | 15.0 | 2.3 | 12.5 | 1.8 |
| | 260 | 0.0 | 0.2 | 6.6 | 2.8 | 10.8 | 3.4 | 5.4 | 0.4 | 6.4 | 1.4 | 6.2 | 2.0 |
| | 261 | 0.0 | 1.4 | 8.0 | 1.5 | 12.2 | 0.9 | 9.7 | 2.6 | 11.1 | 0.6 | 10.6 | 3.9 |
| | 262 | 0.0 | 0.1 | 5.5 | 1.3 | 12.1 | 0.6 | 9.4 | 1.5 | 11.3 | 1.9 | 13.0 | 0.7 |
| | 263 | 0.0 | 2.2 | 5.8 | 1.6 | 9.9 | 1.3 | 16.0 | 5.6 | 14.6 | 0.8 | 15.5 | 3.5 |
| | 264 | 0.0 | 0.1 | 1.3 | 1.2 | 8.1 | 2.0 | 10.1 | 3.5 | 17.1 | 3.0 | 16.0 | 1.5 |
| | 265 | 0.0 | 1.4 | 15.4 | 6.6 | 22.4 | 3.6 | 26.9 | 2.9 | 24.5 | 3.8 | 26.1 | 2.2 |
| 3PG + 2PG | 185 | 100 | 0.6 | 95.4 | 2.2 | 75.6 | 4.7 | 45.5 | 8.6 | 42.6 | 4.0 | 39.3 | 4.4 |
| | 186 | 0.0 | 0.5 | 0.9 | 1.1 | 2.9 | 2.3 | 14.6 | 4.0 | 16.3 | 1.2 | 16.9 | 1.7 |
| | 187 | 0.0 | 0.0 | 2.0 | 0.7 | 7.3 | 1.3 | 23.7 | 0.5 | 25.0 | 1.0 | 24.7 | 0.6 |
| | 188 | 0.0 | 1.0 | 1.7 | 1.3 | 14.2 | 3.5 | 16.2 | 4.2 | 16.1 | 2.2 | 19.1 | 2.1 |
| PEP | 167 | 100 | 0.0 | 97.2 | 3.9 | 72.9 | 9.2 | 45.7 | 8.5 | 41.4 | 6.4 | 34.8 | 2.2 |
| | 168 | 0.0 | 0.7 | 0.4 | 0.5 | 1.9 | 1.6 | 14.6 | 4.7 | 15.1 | 2.4 | 16.3 | 2.5 |
| | 169 | 0.0 | 0.0 | 1.1 | 1.5 | 8.7 | 3.6 | 24.3 | 0.4 | 28.4 | 1.5 | 30.9 | 3.3 |
| | 170 | 0.0 | 0.0 | 1.4 | 0.6 | 16.4 | 5.4 | 15.4 | 5.1 | 15.1 | 1.4 | 18.0 | 4.6 |
| S7P | 289 | 100 | 3.0 | 38.8 | 2.6 | 11.9 | 5.5 | 8.3 | 1.0 | 8.5 | 2.0 | 6.5 | 1.1 |
| | 290 | 0.0 | 0.5 | 10.3 | 2.0 | 11.3 | 4.4 | 7.6 | 3.2 | 7.3 | 0.3 | 6.4 | 1.7 |
| | 291 | 0.0 | 0.1 | 23.5 | 4.8 | 20.4 | 2.3 | 15.0 | 4.1 | 14.4 | 1.3 | 13.5 | 1.5 |
| | 292 | 0.0 | 0.0 | 9.7 | 1.0 | 15.5 | 1.5 | 15.2 | 1.2 | 14.9 | 0.5 | 15.6 | 1.2 |
| | 293 | 0.0 | 0.0 | 8.2 | 1.7 | 15.3 | 1.3 | 17.0 | 0.5 | 17.7 | 1.2 | 17.9 | 0.6 |
| | 294 | 0.0 | 0.0 | 4.7 | 1.6 | 11.8 | 2.0 | 15.6 | 2.1 | 16.1 | 0.4 | 18.3 | 2.1 |
| | 295 | 0.0 | 0.0 | 3.2 | 3.3 | 7.8 | 1.2 | 13.0 | 3.3 | 13.4 | 1.2 | 14.2 | 2.3 |
| | 296 | 0.0 | 2.0 | 1.5 | 2.1 | 6.1 | 3.4 | 8.2 | 3.4 | 7.8 | 1.5 | 7.8 | 1.5 |

[a]The data were the average of 3 independent experiments.
[b]ID, isotopomer distribution: the percentage of the isotopomer relative to the total amount of the compound. SD, standard deviation.

3PG+2PG and PEP were similar in their $^{13}$C distribution patterns, but labeling of these compounds was much slower than of G6P and F6P. After 20 s, 3PG+2PG and PEP were barely labeled (FIG. 5), and it took about 5 min before half of these $C_3$ intermediates carried at least one labeled carbon. At 1.5 minutes, the major labeled peak for 3PG+2PG and PEP was the one in which all three carbons had been labeled, originating from fully labeled G6P+F6P. At 5 minutes and beyond, the major labeled peak of 3PG+2PG and of PEP contained two labeled carbons. The labeling pattern of 3PG+2PG and PEP did not change very much at later time points, and the $^{13}$C-labeled isotopomer distribution had reached a steady state by about 20 min after addition of label. The dominance of a 3PG+2PG pool with two $^{13}$C per molecule suggests under photomixotrophic conditions a significant portion of 3PG is synthesized via the Calvin-Benson-Bassham Cycle, incorporating one unlabeled $CO_2$ per two 3PG synthesized, whereas additional partially labeled 3PG originated from isotope scrambling in the transaldolase and transketolase reactions.

Under photomixotrophic conditions, the S7P pool was labeled rapidly and partially, resembling more the G6P+F6P labeling pattern than that of 3PG+2PG or PEP. After 20 seconds of labeling with $^{13}$C-glucose, the peak corresponding to unlabeled S7P had been reduced to less than 50%, and therefore more than half of the S7P molecules contained one or two $^{13}$C carbons. Such molecules may be formed via reaction of fully labeled F6P with unlabeled GAP to form xylulose-5-phosphate (X5P) with two labeled carbons, followed by a X5P reaction with unlabeled R5P to yield S7P with two $^{13}$C, and GAP. A direct conversion of fully labeled F6P and unlabeled E4P to S7P and PGA would yield three $^{13}$C in S7P, which is less abundant shortly after the start of labeling (FIG. 5), suggesting that molecular exchange through the transketolase reaction is more rapid than the one through the transaldolase reaction under our experimental conditions. After longer labeling times, all S7P isotopomers are present in considerable amounts (6-20% of the total), indicating an essentially complete scrambling of label in S7P. In any case, the molecular exchange among the sugar phosphates seems to be much faster than conversion to phosphoglycerate, suggesting that the step between glyceraldehydes-3-phosphate and phosphoglycerate is relatively slow.

Labeling of Photomixotrophically Grown Cultures with NaH$^{13}$CO$_3$.

Figure 6:
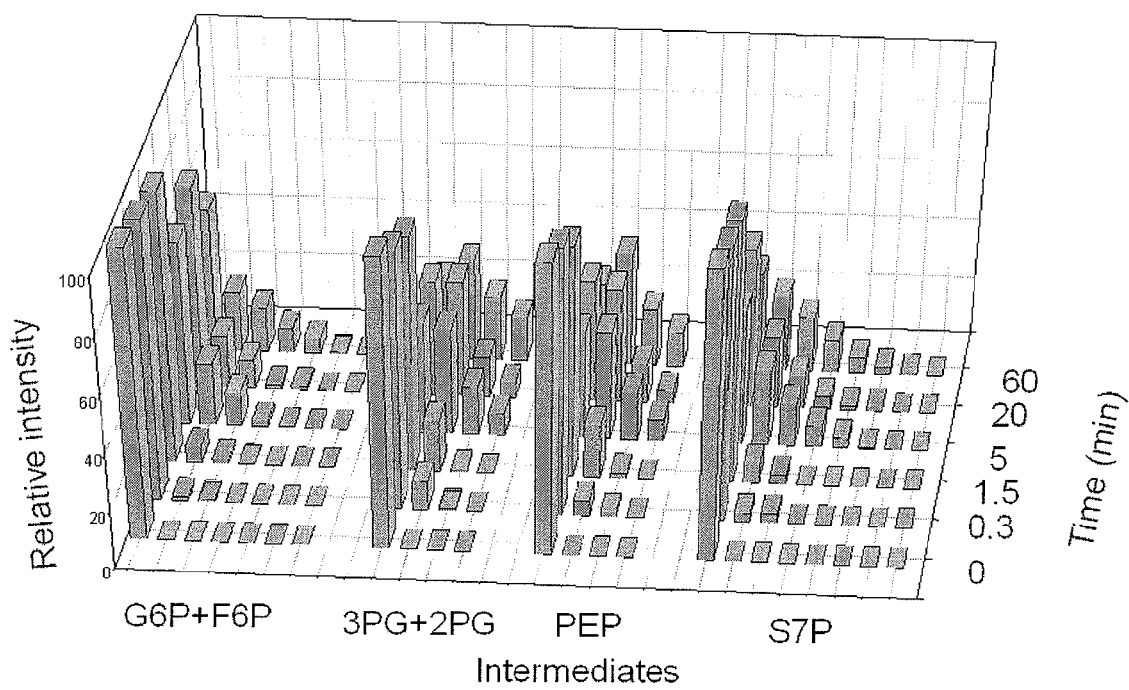
FIG. 6. Isotope distribution of hexose-6-phosphate (G6P+F6P), phosphoglycerate (3PG+2PG), phosphoenolpyruvate (PEP) and sedoheptulose-7-phosphate (S7P) pools in extracts from cells as a function of time of growth under photomixotrophic conditions after addition of labeled bicarbonate. 0.5 mM unlabeled glucose and 5 mM NaH$^{13}$CO$_3$ were added at time 0. Isotopomers are separated on the X-axis according to mass (left to right: unlabeled mass, mass+1, mass+2, etc.). The data were the mean of three experiments. Standard deviation analysis showed that changes in relative intensity of more than 5% were significant.

FIG. 6 illustrates the results of labeling of photomixotrophically grown cultures with 5 mM NaH$^{13}$CO$_3$; 0.5 mM unlabeled glucose was added to the cultures as well. These data are presented quantitatively in Table 4. As photosynthetic $CO_2$ fixation results in formation of 3PG, it is not surprising that $^{13}$C originating from bicarbonate was most rapidly incorporated into the 3PG+2PG and PEP pools: a clearly measurable amount of 3PG+2PG and PEP with one labeled $^{13}$C already could be demonstrated 20 s after the start of labeling, whereas very little labeled G6P+F6P was detected at that time (FIG. 6). After five min, more than half of the molecules in the 3PG+2PG and PEP pools contained at least one $^{13}$C. The formation of 3PG+2PG molecules with more than one $^{13}$C is expected as some of the 3PG is used again for reactions in the Calvin-Benson-Bassham Cycle. After longer periods of labeling, the labeling pattern of 3PG+2PG and PEP did not change greatly, indicating that $^{13}$C-labeling pattern had come close to a steady-state, with the amount of incorporated label approximating the amount of carbon that was fixed via the Calvin-Benson-Bassham cycle vs. what originated from (unlabeled) glucose.

Labeling of Photoheterotrophically Grown Cultures with $^{13}$C-Glucose.

Figure 7:
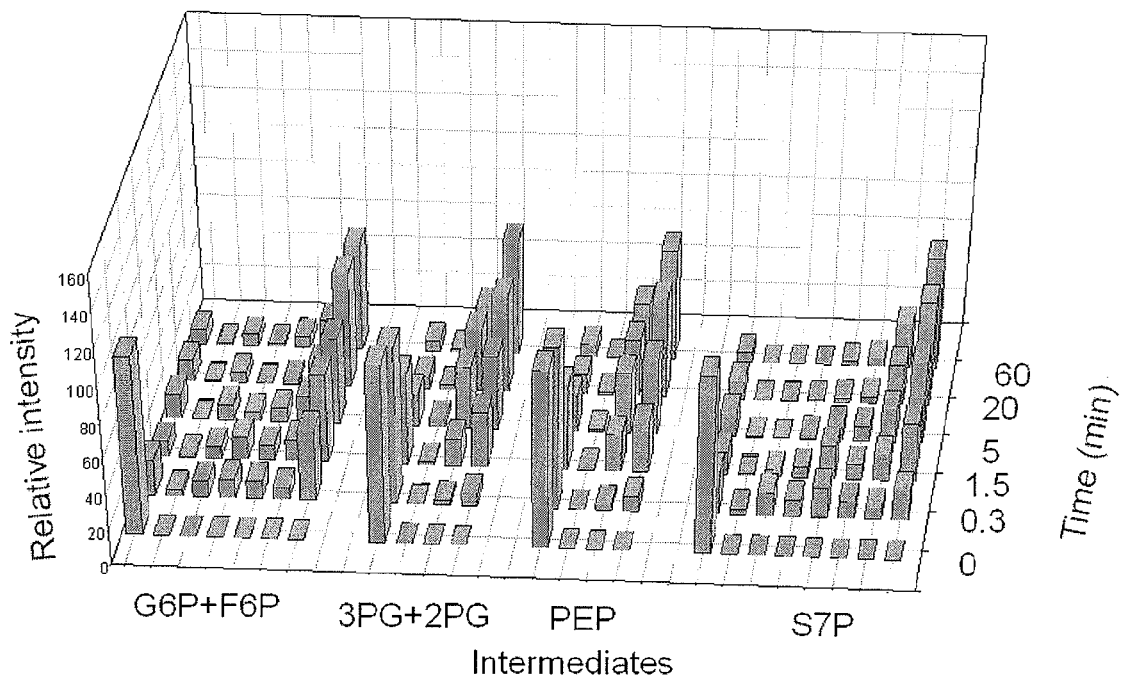
FIG. 7. Isotope distribution of hexose-6-phosphate (G6P+F6P), phosphoglycerate (3PG+2PG), phosphoenolpyruvate (PEP) and sedoheptulose-7-phosphate (S7P) pools in extracts from cells as a function of time of growth under photoheterotrophic conditions in the presence of 25 µM atrazine. 0.5 mM $^{13}$C glucose was added at time 0. Isotopomers are separated on the x-axis according to mass (left to right: unlabeled mass, mass+1, mass+2, etc.). The data were the mean of three experiments. Standard deviation analysis showed that changes in relative intensity of more than about 5% were significant.

When *Synechocystis* was grown under photoheterotrophic conditions (i.e., in the presence of the PS II inhibitor atrazine, along with a fixed-carbon source such as glucose), net $CO_2$ fixation was negligible as even two hours after addition of NaH$^{13}$CO$_3$ the 3PG+2PG pool remained unlabeled (data not shown). Indeed, as shown in FIG. 7, photoheterotrophic growth conditions were by far the most effective of the three conditions probed in this study to rapidly label all intermediates with $^{13}$C-glucose. After 20 seconds of labeling, more than half of the G6P+F6P pool was labeled already and—in contrast to the situation under photomixotrophic conditions—the fully labeled sugar phosphate was most prevalent.

TABLE 4

Dynamic isotopomer distribution of hexose-6-phosphate (G6P + F6P), phosphoglycerate (3PG + 2PG), phosphoenolpyruvate (PEP), and sedoheptulose-7-phosphate (S7P) upon $^{13}$C-NaHCO$_3$ labeling in photomixotrophically grown *Synechocystis* sp. PCC 6803.[a]

| | | \multicolumn{12}{c}{labeling time (min)} | | | | | | | | | | | | |
|---|---|---|---|---|---|---|---|---|---|---|---|---|---|
| | | 0 | | 0.33 | | 1.5 | | 5 | | 20 | | 60 | |
| Compound | mass | ID[a] | SD | ID | SD | ID | SD | ID | SD | ID | SD | ID | SD |
| G6P + F6P | 259 | 100 | 0.7 | 97.8 | 3.8 | 92.8 | 1.6 | 64.0 | 5.3 | 69.0 | 6.8 | 49.3 | 3.2 |
| | 260 | 0.0 | 0.0 | 1.4 | 1.3 | 5.5 | 1.4 | 21.8 | 3.3 | 18.2 | 3.8 | 20.8 | 1.3 |
| | 261 | 0.0 | 0.3 | 0.9 | 1.2 | 1.5 | 1.3 | 11.7 | 1.0 | 9.9 | 0.5 | 15.6 | 1.8 |
| | 262 | 0.0 | 0.0 | 0.0 | 0.0 | 0.2 | 0.4 | 2.2 | 1.7 | 1.4 | 1.0 | 8.5 | 1.0 |
| | 263 | 0.0 | 0.0 | 0.0 | 0.0 | 0.0 | 0.0 | 0.3 | 0.5 | 1.4 | 1.3 | 5.3 | 2.7 |
| | 264 | 0.0 | 0.0 | 0.0 | 0.0 | 0.0 | 0.0 | 0.0 | 0.0 | 0.0 | 0.0 | 0.7 | 0.7 |
| | 265 | 0.0 | 0.0 | 0.0 | 0.0 | 0.0 | 0.0 | 0.0 | 0.0 | 0.0 | 0.0 | 0.0 | 0.1 |
| 3PG + 2PG | 185 | 100 | 0.6 | 89.1 | 1.2 | 81.1 | 2.8 | 38.8 | 7.8 | 40.1 | 4.1 | 27.8 | 2.0 |
| | 186 | 0.0 | 0.2 | 10.2 | 0.4 | 18.0 | 0.9 | 36.7 | 4.2 | 40.3 | 1.4 | 34.6 | 2.2 |
| | 187 | 0.0 | 0.3 | 0.8 | 0.5 | 1.0 | 0.9 | 16.8 | 2.1 | 14.2 | 0.7 | 22.3 | 3.8 |
| | 188 | 0.0 | 0.0 | 0.0 | 0.0 | 0.0 | 0.0 | 7.8 | 3.2 | 5.4 | 1.1 | 15.3 | 2.5 |
| PEP | 167 | 100 | 1.7 | 93.4 | 7.4 | 79.7 | 2.1 | 37.4 | 6.6 | 42.3 | 4.5 | 28.5 | 4.8 |
| | 168 | 0.0 | 0.2 | 5.2 | 3.5 | 18.5 | 1.6 | 37.9 | 5.4 | 39.6 | 2.2 | 39.2 | 5.2 |
| | 169 | 0.0 | 0.5 | 1.4 | 0.4 | 1.8 | 1.5 | 17.1 | 6.7 | 13.7 | 2.5 | 20.0 | 3.8 |
| | 170 | 0.0 | 0.0 | 0.0 | 0.0 | 0.0 | 0.0 | 7.6 | 1.4 | 4.4 | 0.4 | 12.3 | 1.2 |
| S7P | 289 | 100 | 0.9 | 94.0 | 1.6 | 90.0 | 2.9 | 46.9 | 7.8 | 55.6 | 5.6 | 33.9 | 5.2 |
| | 290 | 0.0 | 0.0 | 3.0 | 0.3 | 6.9 | 0.9 | 26.8 | 3.9 | 25.2 | 0.4 | 26.4 | 3.2 |
| | 291 | 0.0 | 0.4 | 3.0 | 0.3 | 3.1 | 0.9 | 15.1 | 2.1 | 11.8 | 1.0 | 19.2 | 0.3 |
| | 292 | 0.0 | 0.0 | 0.0 | 0.0 | 0.0 | 0.0 | 7.4 | 1.2 | 4.7 | 0.6 | 11.5 | 1.0 |
| | 293 | 0.0 | 0.0 | 0.0 | 0.0 | 0.0 | 0.0 | 3.4 | 1.4 | 1.4 | 1.2 | 5.5 | 0.8 |
| | 294 | 0.0 | 0.0 | 0.0 | 0.0 | 0.0 | 0.0 | 0.4 | 0.7 | 1.5 | 1.7 | 2.5 | 0.9 |
| | 295 | 0.0 | 0.0 | 0.0 | 0.0 | 0.0 | 0.0 | 0.1 | 0.2 | 0.0 | 0.0 | 0.9 | 1.2 |
| | 296 | 0.0 | 0.0 | 0.0 | 0.0 | 0.0 | 0.0 | 0.0 | 0.0 | 0.0 | 0.0 | 0.0 | 0.0 |

[a]The data were the average of 3 independent experiments.
[b]ID, isotopomer distribution: the percentage of the isotopomer relative to the total amount of the compound. SD, standard deviation.

G6P+F6P with a single $^{13}$C (mass 259) started to appear only 1.5 minutes after the beginning of labeling, whereas doubly-labeled G6P+F6P was present in significant amounts five min after the start of labeling. $^{13}$C-labeled S7P appeared slower than 3PG+2PG and PEP, but faster than G6P+F6P. This is in line with S7P being later in the Calvin-Benson-Bassham Cycle (relative to $CO_2$ fixation) than 3PG, and most of the F6P+G6P receiving carbon from $CO_2$ fixation being formed via S7P and other Calvin-Benson-Bassham Cycle intermediates rather than via gluconeogenesis through reverse glycolysis.

Even an hour after addition of labeled bicarbonate, among the labeled S7P molecules the most abundant isotopomer had only a single $^{13}$C, with representation of heavier isotopomers falling off rapidly with increasing mass. This is a consequence of primarily the presence of unlabeled glucose and the high rates of transketolase- and transaldolase-catalyzed exchange, and support the interpretation of glucose metabolism and $CO_2$ fixation both contributing significantly to carbon metabolism under photomixotrophic growth conditions.

Since the pool size of G6P+F6P in the photoheterotrophic culture was similar to that from photomixotrophically grown cells (Table 2), under photoheterotrophic conditions glucose was utilized faster than under photomixotrophic conditions. At all times monitored here, fully labeled G6P+F6P was most abundant, indicating that—in contrast to photomixotrophic conditions—very little $CO_2$ fixation or metabolism of other compounds to sugar phosphates in central metabolism takes place.

As observed with other growth conditions, 3PG+2PG and PEP had a similar labeled pattern. Whereas the most abundant isotopomer was the fully labeled compound, the isotopomer with two labeled C was also abundant relative to the fully labeled one, particularly in the 1.5-20 min labeling timeframe. Labeling of 3PG+2PG and PEP occurred more slowly than that of G6P+F6P or of S7P, further strengthening the interpretation of the observations made under photomixotrophic conditions that there is a ready interchange through the transaldolase and transketolase reactions, but that the interchange with phosphoglycerate is much slower. While fully labeled 3PG, 2PG or PEP may be formed by either glycolysis or the pentose phosphate pathway, the formation of these molecules carrying only two $^{13}C$ labels required a contribution of both the glycolytic and pentose phosphate pathway enzymes. Partially labeled F6P with 2-5 $^{13}C$-labeled carbons derived from pentose phosphate pathway reactions can produce 3PG and 2PG carrying two $^{13}C$ labeled carbons via glycolysis.

After 20 s of labeling with $^{13}C$-glucose under photoheterotrophic conditions, the sum of labeled S7P molecules, particularly those with 2, 4 or 7 $^{13}C$ atoms incorporated, outnumbered the unlabeled ones. S7P molecules with just one $^{13}C$ incorporated were essentially absent. With increasing labeling time, the pool of molecules with six $^{13}C$ atoms increased, while the pools with less $^{13}C$ atoms generally decreased over time, reflecting the depletion of pools of unlabeled intermediates. After 60 min of labeling, most of the S7P was fully labeled and some had one unlabeled C.

The results shown in FIGS. 5-7 indicate that the isotopomer distribution pattern depends on the growth mode and on the nature of the added isotope. The isotopomer distribution pattern was very reproducible under each condition, indicating that in *Synechocystis* the metabolic flux through the central sugar phosphate pathways was well-defined depending on specific growth conditions. Therefore, the variability in measured concentrations of intermediates (Table 2) is likely to reflect variability in extraction efficiency rather than great variability in the metabolic capacities of different *Synechocystis* cultures grown under the same conditions.

Labeling Levels.

To obtain a more direct determination of the amount of label incorporated in central metabolites as a function of time, the amount of $^{13}C$ vs. total carbon was calculated in G6P+F6P, 3PG+2PG, PEP and S7P under different growth conditions as a function of time. The results are summarized in Table 5, confirming the more qualitative observations made in previous sections that G6P+F6P and S7P are more rapidly labeled than 3PG+2PG and PEP under both photomixotrophic and photoheterotrophic conditions using $^{13}C$-glucose as label, whereas when labeling with bicarbonate, label appears in 3PG+2PG and PEP much more rapidly than in G6P+S7P as the three-carbon intermediates are closer to the primary CO$_2$ fixation product (3PG). Similar labeling ratios presumably imply rapid metabolic interconnections. However, even when correcting for the number of carbons in labeled glucose vs. bicarbonate, the amount of label in 3PG+2PG and PEP appears more slowly when labeling with bicarbonate than when labeling with glucose. The reason for this may be differences in uptake rates between glucose and bicarbonate/CO$_2$, differences in the kinetics of the Calvin-Benson-Bassham Cycle vs. of glucose metabolism, and/or differences in the size of the unlabeled carbon pool at the time the experiment is started.

Upon plotting the labeling ratio as a function of labeling time, the labeling ratio of each compound at infinite time after the start of labeling (i.e., the final steady-state labeling ratio) can be extrapolated by regression analysis (Table 5). In photoheterotrophic cultures fed with $^{13}C$-glucose, 90% of the carbon in the sugar phosphates and three-carbon phosphates could be labeled, in line with an inhibition of CO$_2$ fixation under these conditions: virtually all carbon in the central carbon metabolism pathways is derived from glucose. However, when cultures were grown photomixotrophically, only half as much of the total carbon in the 3PG+2PG pool was $^{13}C$-labeled regardless of whether labeled glucose or bicarbonate was provided (Table 5). This indicates that when cells are grown under photomixotrophic conditions about half of the carbon at the 3PG+2PG and PEP level comes from bicarbonate and the other half from glucose. However, under photomixotrophic conditions G6P+F6P and S7P are more intensely labeled by glucose than by bicarbonate; this presumably is due to the fact that these sugar phosphates are only a few metabolic steps removed from glucose, whereas 3PG is the product of CO$_2$ fixation by the Calvin-Benson-Bassham Cycle. In any case, it is interesting that the sum of the $^{13}C$-glucose plus $^{13}C$-bicarbonate labeled fractions for each of the compounds in Table 5 approximates 90% upon steady-state labeling, suggesting that the glucose metabolism and CO$_2$ fixation pathways are fully complementary under photomixotrophic conditions.

TABLE 5

Dynamic labeling ratios in *Synechocystis* sp. PCC 6803 under photomixotrophic (PM) and photoheterotrophic (PH) growth conditions upon labeling with either $^{13}C$-glucose (G) or $^{13}C$-bicarbonate (B).[a]

| Growth mode | Label | Metabolite | $^{13}C$ labeling time (min) | | | | | | |
|---|---|---|---|---|---|---|---|---|---|
| | | | 0 | 0.33 | 1.5 | 5 | 20 | 60 | Final[b] |
| PM | G | G6P + F6P | 0 ± 0.4 | 26.3 ± 2.8 | 48.0 ± 3.8 | 54.9 ± 3.0 | 58.9 ± 1.3 | 60.7 ± 2.3 | 64 |
| | | 3PG + 2PG | 0 ± 0.5 | 3.1 ± 0.9 | 20.2 ± 2.7 | 37.3 ± 5.0 | 38.2 ± 2.3 | 41.2 ± 1.9 | 45 |
| | | PEP | 0 ± 0.3 | 3.8 ± 2.2 | 22.6 ± 4.6 | 36.8 ± 5.6 | 39.1 ± 2.3 | 44.1 ± 2.0 | 45 |
| | | S7P | 0 ± 0.2 | 24.8 ± 2.2 | 44.2 ± 3.6 | 52.2 ± 1.7 | 52.4 ± 0.8 | 54.6 ± 1.3 | 61 |
| PM | B | G6P + F6P | 0 ± 0.4 | 0.9 ± 0.6 | 1.5 ± 0.2 | 9.5 ± 1.3 | 8.0 ± 2.1 | 16.8 ± 0.5 | 24 |
| | | 3PG + 2PG | 0 ± 0.2 | 3.9 ± 0.3 | 6.6 ± 05 | 31.3 ± 3.2 | 28.3 ± 1.2 | 41.7 ± 1.0 | 42.5 |
| | | PEP | 0 ± 0.3 | 3.3 ± 0.9 | 7.2 ± 0.2 | 31.6 ± 2.2 | 26.8 ± 1.6 | 38.9 ± 1.1 | 42.5 |
| | | S7P | 0 ± 0.2 | 1.2 ± 0.4 | 1.7 ± 0.3 | 13.7 ± 1.9 | 11.2 ± 0.6 | 19.9 ± 1.4 | 26 |
| PH | G | G6P + F6P | 0 ± 0.3 | 61.5 ± 0.4 | 74.0 ± 0.1 | 72.2 ± 4.0 | 79.6 ± 2.2 | 83.7 ± 3.1 | 90 |
| | | 3PG + 2PG | 0 ± 0.5 | 9.7 ± 1.3 | 41.9 ± 2.9 | 66.2 ± 3.5 | 78.4 ± 0.3 | 83.0 ± 0.9 | 90 |
| | | PEP | 0 ± 0.4 | 9.0 ± 1.6 | 43.6 ± 0.7 | 66.5 ± 3.6 | 77.2 ± 3.2 | 82.7 ± 2.8 | 90 |
| | | S7P | 0 ± 0.4 | 47.2 ± 0.3 | 66.7 ± 3.0 | 63.9 ± 5.2 | 82.7 ± 4.2 | 88.6 ± 1.4 | 90 |

[a]The labeling ratio is defined as the percentage of the total amount of $^{13}C$ label in all carbons of the compound (including all its jsotopomers). The data were the mean of three independent experiments.
[b]The column labeled Final represents the labeling ratio in steady state, and is extrapolated from the data in this table to the labeling ratio at "infinite" time.

This provides a new approach for the analysis of the central metabolic fluxes in *Synechocystis*, monitoring the dynamic distribution of $^{13}C$-labeled metabolic intermediates as a function of time after addition of a labeled carbon source. In *Synechocystis*, the flux through the central metabolism pathways was fast relative to the pool size of the intermediates, as the labeling pattern of the intermediates changed significantly on the timescale of 20 s-1.5 min.

When $^{13}C$ glucose is added to the culture, it is readily taken up by the cells and phosphorylated. From the G6P+F6P pool molecules can be used for the pentose phosphate pathway or glycolysis, or be converted to other sugar phosphates via the transaldolase and transketolase reactions. When labeling photomixotrophic or photoheterotrophic cultures with uniformly labeled $^{13}C$-glucose (FIGS. 5 and 7), one of the unexpected features was the rapid formation of partially labeled G6P+F6P molecules, indicating rapid scrambling of the label and thereby interconversion between the G6P+F6P pool and partially labeled pools of molecules with a different number of carbon atoms. The scrambling of label in the G6P+F6P pool resembled that of S7P, suggesting a direct or indirect, but dynamically rapid, interaction between these two types of sugar phosphates. The way of this rapid scrambling can be manifold, with each isotopomer being formed through a combination of the reactions. Detailed analysis of the labeling patterns can reveal the general metabolic fluxes under different growth conditions. Particularly the transketolase and transaldolase reactions involving F6P play a major role in the rapid scrambling of isotopomers. The rate of the transaldolase reaction (F6P+E4P to S7P+GAP and vice versa) did not appear to be as high as that of the transketolase reactions as there was not a preponderance of S7P with 3 or 7 labeled carbons 20 s after the addition of $^{13}C$-glucose under photomixotrophic conditions (FIG. 5). Moreover, the fact that the S7P isotopomer with five $^{13}C$ was low but with two $^{13}C$ was high after 20 s of labeling suggests that the flux from Ru5P to R5P was relatively low; in contrast the flux between Ru5P and X5P was much faster to ensure the free flow of the Calvin Calvin-Benson-Bassham cycle and pentose phosphate pathway.

In the photoheterotrophic labeling pattern of G6P+F6P, the most abundant isotopomer at all time points after labeling was mass+6, consistent with rapid influx of glucose under these growth conditions. Like in photomixotrophic conditions, rapid labeling of mass+2 and mass+4 of G6P+F6P indicated that reaction 16 occurred and was reversible. Compared to growth under photomixotrophic conditions, the G6P+F6β isotopomer with five labeled C was abundant after 20 s and the one with one labeled C was not. This difference is likely due to E4P being readily labeled under photoheterotrophic conditions, which may suggest a smaller E4P pool or more rapid exchange with carbons originating from glucose. The G6P+F6β isotopomer with three labeled carbons most likely originated from labeled S7P after a transaldolase reaction (reaction 15) with unlabeled GAP.

S7P Pool.

The fully labeled S7P isotopomer, originating from fully labeled R5P and X5P carrying at least two $^{13}C$, already was present in significant amounts 20 s after the start of labeling in cells growing under photoheterotrophic conditions, well before the rise in labeled 3PG+2PG, indicating rate-limiting steps downstream of S7P. The S7P isotopomer with two labeled carbons, presumably formed by reaction of unlabeled R5P with labeled X5P (reaction 14), was only transient and had virtually disappeared 1.5 min after the start of labeling (FIG. 7) indicating that the sugar phosphate pool is rapidly labeled. The disappearance of other partially labeled S7P isotopomer pools with time (e.g., isotopomers with four or five $^{13}C$'s) further supports this argument.

3PG+2PG and PEP Pools.

With $^{13}C$-glucose, the amount of label in the 3PG+2PG peak remained very small until the 1.5 min time point, regardless whether cells were grown under photomixotrophic or photoheterotrophic conditions (Table 5). In Synechocystis, the GAP pool was small (FIG. 1B), and the delay in label arriving in the 3PG+2PG and PEP pools suggests that the flux from GAP to 3PG was slow relative to fluxes among sugar phosphates.

In Synechocystis, there are two GAP dehydrogenases, one (GAP-1) apparently catalyzing the forward reaction (GAP to diphosphoglycerate) and the other (GAP-2) the backward reaction (diphosphoglycerate to GAP) (Koksharova et al., 1998). Expression of the gene coding for GAP-1 is weak (Figge et al., 2000), and therefore this step may be rate-limiting to minimize loss of carbon from the sugar phosphate pool. If indeed GAP-1 is rate-limiting, and as both the pentose phosphate pathway and glycolysis make use of this step, the question of which of these pathways is most important for sugar metabolism in cyanobacteria (Yang et al., 2002a) may have lost most of its importance. The importance of GAP dehydrogenase in regulation of the sugar phosphate metabolic network was also reported in other photosynthetic systems (Ihlenfeldt and Gibson, 1975; Tamoi et al., 2005; Wedel and Soll, 1998).

Under photomixotrophic conditions formation of 3PG via carbon fixation (not involving GAP-1) appears to be a major pathway. This may fit with the concept that RuBisCO activity by itself is not a major bottleneck of photosynthetic fluxes in cyanobacteria (Marcus et al., 2005). As shown in FIG. 6 and Table 5, under photomixotrophic conditions with labeled bicarbonate, labeling of the 3PG+2PG and PEP pools is much more than of the sugar phosphate pools, indicating that the flux from 3PG to PEP is very fast, and the influx of G6P+F6P pool from gluconeogenesis is not dominant comparing with its influx from glucose. The high labeling ratio also suggested that the Calvin-Benson-Bassham cycle was very fast in recycling the fixed $CO_2$. Since $CO_2$ can only provide about half of carbon source for 3PG+PEP pool (Table 5), two thirds of produced 3PG by the Calvin-Benson-Bassham cycle needed to flow back to sugar phosphates including F6P. Under photomixotrophic conditions, the mRNA and protein expression levels for GAP-2 were increased about two-fold than under photoheterotrophic conditions in Synechocystis (Yang et al., 2002b). The reactions 16 (GAP+S7P to F6P+E4P) also involved in regeneration of G6P+F6P pool in addition to the influxes from glyconeogenesis and glucose utilization, at the same time the consumed S7P was refreshed. It was interesting to notice that during the RuBP regeneration, the mainstream of the carbon flow was from 3PG to GAP, X5P, Ru5P and RuBP, and those intermediate pools were relatively separated from other intermediates, such as G6P+F6P, E4P and S7P, by a chemical reaction barrier due to the nature of the carbohydrate metabolic network.

Glycolysis and Pentose Phosphate Pathway.

Several papers have suggested that under photoheterotrophic conditions the majority of G6P is utilized through the pentose phosphate pathway (involving decarboxylation of 6-phosphogluconate) and very little is metabolized through glycolysis (e.g., (Pelroy et al., 1972; Yang et al., 2002a)). Indeed, S7P is fully labeled very rapidly under photoheterotrophic conditions (FIG. 7), indicating that all sugar phosphate pools (including E4P, X5P, etc.) are rapidly labeled, consistent with an active pentose phosphate cycle. Full S7P labeling was not observed under photomixotrophic conditions (FIG. 5), indicative of significant unlabeled sugar phosphate pools and perhaps less conversion of G6P to phosphogluconate. However, in Synechocystis, Knowles and Plaxton (Knowles and Plaxton, 2003) reported the activity of glucose-6-phosphate dehydrogenase (G6PDH) (and also of phosphofructokinase) to remain unchanged in photomixotrophic vs.

photoheterotrophic growth conditions suggesting that most glycolysis and pentose phosphate pathway reactions were regulated mainly at the substrate level. However, the G6P+F6P pool (Table 1) as well as the G6P/F6P distribution (data not shown) did not change greatly between the two growth conditions. Also, in the dark in the presence of glucose G6PDH activity was reported to increase more than 10-fold (Kurian et al., 2006), and G6PDH was highly inhibited by RuBP and NADPH in cell-free extracts (Pelroy et al., 1972; Pelroy et al., 1976). Therefore, an important flux through the pentose phosphate pathway under at least photoheterotrophic conditions is apparent and is fully consistent with the observations.

Under photomixotrophic conditions, the peak of one carbon labeled G6P+F6P by $^{13}$C glucose revealed that G6PDH was still functional, although this flux could be quite small because under these conditions the 3PG+2PG pool was not labeled rapidly. However, in some studies (Shasri and Morgan, 2005; Yang et al., 2002a), this flux was neglected. In spite of the difference in growth conditions, mainly the light intensity and inorganic carbon source, the discrepancy was more likely caused by the interpretation of their data. Although pentose phosphate pathway and Calvin-Benson-Bassham cycle are mainly a reverse process, the dominance of Calvin-Benson-Bassham cycle under mixotrophic conditions did not rule out the possibility that G6PDH was still functional. Another major difference of our flux map comparing with previous (Yang et al., 2002a) was that in our constructed metabolic network, the DHAP, GAP and 3PG+2PG pool were separately considered due to their roles in central metabolic networks and distinguishable behaviors in $^{13}$C labeling measurement. Basing on the labeling patter of 3PG+2PG by C13 bicarbonate, it was found that under photomixotrophic conditions, regeneration of G6P+F6P from recycled 3PG was required.

The results presented here indicate that direct detection of stable-isotope labeling over time provides a direct way to determine metabolic connections and rates between compounds. This work presently is a first step, and modeling as well as more sensitive detection of compounds will aid in more detailed analysis. With the application of additional labeling, more sensitive metabolite detection, and combined with mutation analysis, even more detailed metabolic flux analysis in vivo can be carried out. This method can be easily applied to microorganisms that readily take up specific fixed-carbon compounds for a direct and rapid measurement of their metabolic fluxes, even using microorganisms that have a metabolic network that is not yet fully understood.

TABLE 6

Dynamic isotopomer distribution of hexose-6-phosphate (G6P + F6P), phosphoglycerate (3PG + 2PG), phosphoenolpyruvate (PEP), and sedoheptulose-7-phosphate (S7P) upon $^{13}$C-glucose labeling in photoheterotrophically grown *Synechocystis* sp. PCC 6803.[a]

| | | labeling time (min) | | | | | | | | | | | |
|---|---|---|---|---|---|---|---|---|---|---|---|---|---|
| | | 0 | | 0.33 | | 1.5 | | 5 | | 20 | | 60 | |
| Compound | mass | ID[b] | SD[b] | ID | SD | ID | SD | ID | SD | ID | SD | ID | SD |
| G6P + F6P | 259 | 100 | 3.5 | 19.9 | 3.0 | 9.0 | 0.3 | 13.9 | 5.0 | 11.9 | 3.4 | 8.6 | 2.8 |
| | 260 | 0.0 | 0.0 | 3.3 | 0.4 | 2.0 | 1.5 | 0.7 | 0.6 | 0.8 | 1.1 | 1.2 | 1.5 |
| | 261 | 0.0 | 1.3 | 9.0 | 0.7 | 6.6 | 3.6 | 8.7 | 2.1 | 5.9 | 7.0 | 6.6 | 7.6 |
| | 262 | 0.0 | 0.4 | 10.6 | 4.6 | 12.4 | 4.4 | 5.0 | 2.1 | 1.3 | 1.6 | 2.1 | 1.9 |
| | 263 | 0.0 | 0.5 | 9.8 | 0.8 | 8.4 | 2.7 | 7.7 | 3.4 | 3.3 | 3.1 | 6.2 | 0.7 |
| | 264 | 0.0 | 0.5 | 6.9 | 1.8 | 12.2 | 2.3 | 15.4 | 4.0 | 13.2 | 1.6 | 15.7 | 4.5 |
| | 265 | 0.0 | 2.7 | 40.4 | 6.8 | 49.5 | 4.3 | 48.7 | 7.8 | 63.6 | 7.5 | 59.5 | 7.2 |
| 3PG + 2PG | 185 | 100 | 0.3 | 89.2 | 3.0 | 51.5 | 6.1 | 19.1 | 1.6 | 7.9 | 5.9 | 6.5 | 4.7 |
| | 186 | 0.0 | 0.7 | 0.9 | 0.9 | 1.8 | 0.3 | 4.6 | 4.4 | 2.8 | 1.7 | 1.9 | 0.0 |
| | 187 | 0.0 | 0.4 | 2.5 | 1.3 | 15.6 | 3.2 | 34.9 | 8.4 | 35.0 | 6.2 | 27.4 | 7.1 |
| | 188 | 0.0 | 0.3 | 7.3 | 0.3 | 31.1 | 6.4 | 41.3 | 8.2 | 54.3 | 8.8 | 64.2 | 7.0 |
| PEP | 167 | 100 | 3.0 | 88.6 | 6.0 | 48.4 | 1.5 | 21.0 | 4.6 | 11.0 | 5.4 | 7.1 | 6.2 |
| | 168 | 0.0 | 0.2 | 0.0 | 1.2 | 1.8 | 2.5 | 1.7 | 1.4 | 1.6 | 2.0 | 0.3 | 0.2 |
| | 169 | 0.0 | 2.5 | 3.4 | 3.6 | 21.2 | 2.6 | 34.4 | 6.1 | 32.0 | 5.4 | 31.2 | 4.8 |
| | 170 | 0.0 | 0.0 | 7.9 | 4.0 | 28.6 | 5.4 | 42.9 | 4.7 | 55.4 | 3.5 | 61.5 | 4.6 |
| S7P | 289 | 100 | 0.8 | 24.4 | 4.4 | 13.2 | 6.5 | 13.7 | 4.5 | 10.4 | 5.9 | 5.3 | 1.8 |
| | 290 | 0.0 | 0.0 | 3.1 | 1.4 | 1.4 | 0.8 | 0.7 | 7.4 | 0.6 | 1.0 | 0.0 | 0.2 |
| | 291 | 0.0 | 0.5 | 13.2 | 4.7 | 3.9 | 1.6 | 0.3 | 0.4 | 0.4 | 0.1 | 0.2 | 0.3 |
| | 292 | 0.0 | 0.0 | 9.4 | 0.3 | 6.0 | 1.8 | 2.6 | 3.7 | 1.0 | 0.3 | 0.2 | 0.3 |
| | 293 | 0.0 | 0.0 | 16.8 | 4.8 | 18.9 | 3.4 | 8.6 | 3.6 | 2.6 | 0.2 | 2.6 | 0.6 |
| | 294 | 0.0 | 0.0 | 9.3 | 3.9 | 8.6 | 2.9 | 8.6 | 5.0 | 3.9 | 1.1 | 4.7 | 1.1 |
| | 295 | 0.0 | 0.0 | 6.7 | 2.5 | 14.8 | 1.3 | 18.9 | 0.8 | 22.5 | 3.8 | 24.7 | 3.4 |
| | 296 | 0.0 | 0.8 | 17.0 | 2.3 | 33.3 | 2.3 | 46.5 | 9.4 | 58.4 | 1.8 | 62.3 | 4.7 |

[a]The data were the average of 3 independent experiments.
[b]ID, isotopomer distribution: the percentage of the isotopomer relative to the total amount of the compound. SD, standard deviation.

Toward accABCD Overexpression.

Figure 12:
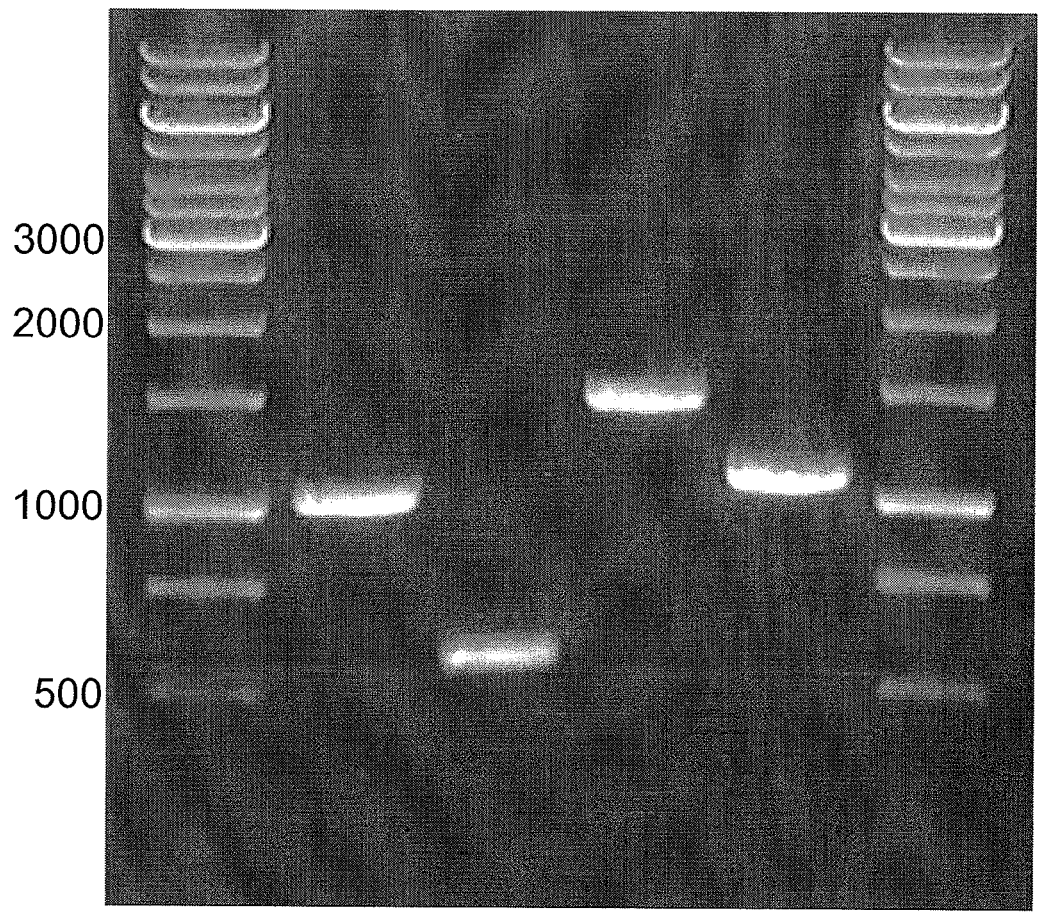
FIG. 12. PCR products representing the amplified accA, accB, accC, and accD genes from *Synechocystis*, together coding for the ACC complex.
Figure 13:
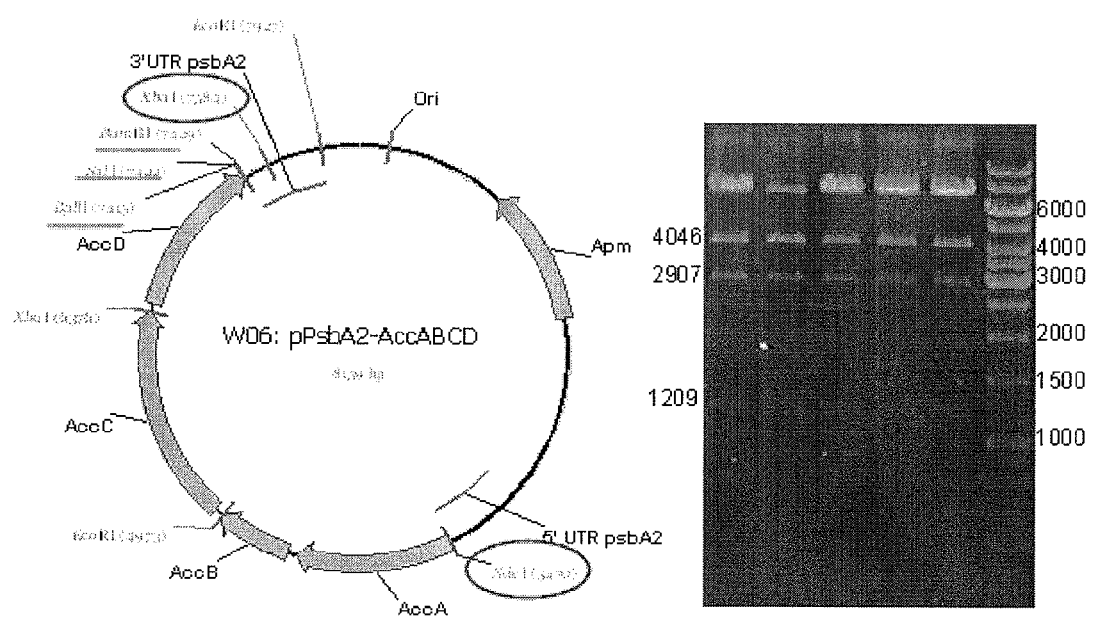
FIG. 13. Plasmid construct containing all acc genes, with flanking regions designed for insertion into the psbA2 locus of the *Synechocystis* genome. The neighboring gel illustrates that multiple transformants carried the desired plasmid.

A first step in metabolic engineering toward increased lipid biosynthesis is to overexpress components of the acetyl-CoA carboxylase enzyme, AccABCD. The coding regions of the accA, accB, accC, and accD genes from *Synechocystis* sp. PCC 6803 were PCR-amplified (FIG. 12) and a plasmid for concerted expression of these genes in the *Synechocystis* genome is indicated in FIG. 13.

Example 3

Modified Cyanobacteria for Increasing the PHB (Bioplastic) Content

1. Material and Methods
Bacterial Strains and Culture Conditions
To understand the physiological role of PHB synthesis in *Synechocystis* sp. PCC 6803, a series of mutants with altered metabolic pathways resulting in significantly different PHB content were compared under various culture conditions. A mutant lacking the three terminal oxidases (a cytochrome aa$_3$-type cytochrome c oxidase (CtaI), a putative cytochrome bo-type quinol oxidase (CtaII) and a quinol oxidase of the cytochrome bd-type (Cyd)) has been described in (Howitt et al., 1998). A PS II-less/oxidase-less mutant lacking both photosynthetic oxygen evolution and respiratory oxygen consumption was established later (Howitt et al., 2001) by additional deletion of psbB encoding the CP47 protein of photosystem II. CyanoRubrum, a gift from Dr. Michael Gurevitz (Tel-Aviv University, Israel), is a mutant in which the original cyanobacterial RuBisCO genes were replaced with the corresponding gene from *Rhodospirillum rubrum*, an organism carrying out anoxygenic photosynthesis (Amichay et al., 1992). Because *R. rubrum* RuBisCO has a relatively high oxygenation vs. carboxylation activity, the mutant can grow only at increased $CO_2$ concentration. The ndhB$^-$ strain lacking the type I NADPH-preferring dehydrogenase (NDH-1), a gift from Dr. Teruo Ogawa (formerly at the University of Nagoya, Japan), also requires air enriched in $CO_2$ for growth because of impaired $C_i$ transport (Ogawa, 1991). The strain lacking the NADH-oxidizing type II dehydrogenase (NDH-2) was constructed by deletion of the three corresponding genes (ndbA, ndbB, and ndbC) found in *Synechocystis* sp. PCC 6803 (Howitt et al., 1999).

The *Synechocystis* sp. PCC 6803 wild type, terminal oxidase-less, PS II-less/oxidase-less and NDH-2-less mutants were grown in BG-11 medium and bubbled at 30° C. with air; the CyanoRubrum and NDH-1-less stains were bubbled with air enriched with 2% $CO_2$. The BG-11 medium was buffered with 5 mM TES [N-tris(hydroxymethyl)methyl-2-aminoethanesulfonic acid]-NaOH (pH 8.0) except that 10 mM TES-NaOH (pH 8.0) was added to the PS II-less/oxidase-less cultures. Because the PS II-less/oxidase-less has lost the ability to grow photoautotrophically, it was supplied with 5 mM glucose in the medium in all conditions. Where indicated, NaNO3 was omitted from BG-11 and replaced with 10 mM NH4Cl ("N-reduced"). Nitrogen- or phosphorus-starved cultures were obtained by washing and transferring pelleted cells grown in normal BG-11 medium into BG-11 from which NaNO3 or K2HPO4, respectively, had been omitted. In nitrogen- or phosphorous-limited conditions, the respective source in the medium was reduced to 10% of the original concentration. Where indicated, 6-diazo-5-oxo-L-norleucine (DON), a specific inhibitor of glutamate synthase (also known as glutamate synthase-glutamine (amide)-2-oxoglutarate aminotransferase (GOGAT)) was added to BG-11 medium to a final concentration of 0.5 mM.

For growth on plates, 1.5% (w/v) agar and 0.3% (w/v) sodium thiosulfate were added, and BG-11 was supplemented with antibiotics to which a particular strain was resistant due to the presence of antibiotic resistance markers introduced with gene inactivation. Concentrations used were: 20 µg of zeocin ml$^{-1}$, 25 µg of kanamycin ml$^{-1}$, 25 µg of erythromycin ml$^{-1}$, 25 µg of spectinomycin ml$^{-1}$ and/or 14 µg of chloramphenicol ml$^{-1}$.

Strains were grown photoautotrophically at a light intensity of 50 mmol photons m$^{-2}$ s$^{-1}$, unless indicated otherwise. Growth was monitored by measuring the optical density of cultures at 730 nm with a Shimadzu UV-160 spectrophotometer. Mid-exponential phase cultures were acquired at $OD_{730}$~0.5; stationary phase cultures were harvested after 7 days of growth.

Light and Electron Microscopy:

To observe PHB granules by light microscopy, 50 µl of a filter-sterilized 1% aqueous solution of the oxazine dye Nile blue A was added to a 2 ml aliquot of *Synechocystis* culture, and the cells were grown for 12 h under standard conditions before observation. Then cells were pelleted by centrifugation and washed twice with BG-11 medium. Cells were immobilized on a microscope slide with a thin layer of 1% (w/v) BG-11 agar, and were covered immediately with a cover slip. Slides were examined under either a Zeiss epifluorescence microscope (Axioskop) or a Leica TCS SP2 multi-photon confocal laser scanning microscope, with excitation at 488 nm and fluorescence emission detected between 560 nm and 620 nm. The cell morphology was monitored in differential interference contrast (DIC) mode or fluorescence mode after staining (Excitation filter: BP 450-490. Beam filter: FT 510. Barrier filter: BP 515-565). Transmission electron microscopy was performed essentially as described previously (Mohamed et al., 2005). Cells were cryofixed using a Balzers high-pressure freezer. Freeze-substitution took place over 48-72 hours at −85° C. using 1% glutaraldehyde and 2% tannic acid in acetone with further fixation in 1% OsO4 in acetone for 8 hours. Cells were embedded in Spurrs resin and cut into 70 nm thick sections; these sections were then poststained with uranyl acetate and lead citrate. Cells were viewed at 80 kV using a Philips CM12 scanning-transmission electron microscope.

PHA Analysis and Quantification:

The intracellular PHA content of different strains was analyzed by gas chromatography-mass spectrometry (GC/MS). Cell cultures (200-400 ml) at $OD_{730}$=0.5 (representing exponential phase) or $OD_{730}$>1.0 (representing stationary phase; cultured for 7 days) were collected by centrifugation (10 min, 3,200×g, 4° C.) or filtration through 1 µm pore size membranes, and cells were washed twice with water. The resulting pellet was frozen in liquid nitrogen, stored at −80° C. and lyophilized for at least 24 hours. Cells were then dried at 105° C. for 4 h. Dry cells (10-30 mg) were disrupted with a Mini-BeadBeater™ (Biospec Products, Bartlesville, Okla.) in 1.5 ml chloroform (3×60 s) with 30 s incubations on ice in between. A one-ml aliquot was taken out and combined with 1 ml acidified methanol (20% HCl v/v) for methanolysis. Samples and PHB standards (0.1-10 mg/ml) were heated for 2.5 h at 95° C. in 15 ml Pyrex test tubes with Teflon-lined caps. Subsequently, samples were cooled by incubation on ice for 5 min. Further purification was achieved by transferring 0.5 ml of the denser chloroform phase to another 10 ml Pyrex tube containing 0.5 ml $H_2O$. After vigorous shaking for 3 min and centrifugation (1,500×g for 3 min), 2 µl of the chloroform phase containing the PHB methyl ester was injected onto the GC column for analysis.

GC/MS analysis was performed on a Shimadzu 17-A gas chromatograph with a DB-5 MS column (30 m by 0.25 µm inside diameter, 0.25 µm film thickness) and a Shimadzu QP5000 mass spectrometer linked to a data processor (GC-MSsolutions software; Shimadzu, Japan). At 200° C. the linear velocity was 20 to 30 cm/s with helium as the carrier gas. The temperature of the injection port was set to 210° C. and the interface temperature was set to 250° C. The following GC oven temperature profile was used: 1 min at 60° C., followed by a temperature increase rate of 8° C./min up to 160° C., then 5 min isothermal heating at 160° C. and a post-run of 4 min at 200° C. The equilibration time was 2 min at 60° C. The Single Ion Monitoring (SIM) mode was used following each detection in total ion scan mode for higher quantification accuracy.

Nicotinamide Nucleotide Assay:

Two independent methods were adapted to analyze nicotinamide nucleotide levels in each strain. First, the reduction level of NAD and NADP was determined spectrophotometrically by an enzymatic reaction method modified from (Zhang et al., 2000). About 400-500 ml of liquid culture was harvested by centrifugation at 4° C. The pellet was washed twice with $H_2O$ and resuspended in 1 ml extraction buffer containing 0.1 M Tris-HCl, pH 8.0, 0.01 M EDTA, and 0.05% (v/v) Triton X-100. Approximately a half volume of glass beads (70-100 μm diameter) was added and cells were broken using a Mini-BeadBeater™ (4×30 s with a one-minute incubation on ice between shakings). Following breakage, all steps were carried out in darkness to avoid photodegradation of the pyridine nucleotides. The mixture was spun at 14,000 rpm in an Eppendorf microcentrifuge for 3 min, and the supernatant was transferred to a new tube. The supernatant was extracted twice with half a volume of chloroform to remove lipids and most protein. Readings of the absorbance at 340 nm were taken under four different conditions as follows. The total (NADPH+NADH) level was determined by adding 20 μl extract to the original extraction buffer to a final volume of 1 ml (A1). By adding another 20 μl of the extract to a 1 ml of reaction mixture containing 0.1 M Tris-HCl (pH 8.0), 0.01 M $MgCl_2$, 0.05% (v/v) Triton X-100, 5 mM glucose-6-phosphate, and 5.0 IU NADP-specific glucose-6-phosphate dehydrogenase (G6PD; Sigma Chemical Co., G-4134) and incubating at 37° C. for 5 min, all $NADP^+$ in sample was converted to NADPH (A2). A third aliquot of 20 μl extract was incubated in a reaction mixture containing 0.1 M phosphate buffer (pH 7.6), 0.05% (v/v) Triton X-100, 5 mM glutathione (GSSG) and 5.0 IU glutathione reductase (GR; Sigma), at 25° C. for 5 min, converting all NADPH to $NADP^+$ (A3). The fourth reading was taken after reaction of 20 μl extract in a 1 ml mixture of 0.1 M Tris-HCl, pH 8.0, 1% (w/v) bovine serum albumin, 7% ethanol, 5.0 IU NAD-specific alcohol dehydrogenase at 25° C. for 5 min (A4), converting $NAD^+$ to NADH. All reaction mixtures were preincubated at the corresponding temperature for 5 min before the extract was added. A1-A3 represents the total amount of NADPH in the sample; A2-A1 represents the total amount of $NADP^+$; A3 represents the total amount of NADH; and A4-A1 represents the total amount of $NAD^+$. The molar extinction coefficient of NAD(P)H was taken to be $6.3 \times 10^3$ $cm^{-1}$ (Bergmeyer, 1975).

A fluorescence-based high-pressure liquid chromatography (HPLC) method adapted from that of Klaidman et al. (1995) was previously described (Cooley et al., 2001) to extract and detect NADP-NADPH and NAD-NADH after derivatization. First, one liter of cells ($OD_{730}$=0.5) was pelleted and resuspended to 1 ml in a mixture containing 0.06 mM KOH, 0.2 mM KCN, and 1 mM bathophenanthrolinedisulfonic acid. In this solution, the oxidized forms of NAD and NADP are derivatized with CN, making the oxidized form visible by fluorescence (emission at 460 nm upon excitation at 330 nm) at an efficiency nearly equivalent to that of the reduced form (Klaidman et al., 1995). Glass beads were added to a total volume of 1.5 ml, and the cells were broken as described above. Samples were spun at 14,000 rpm for 5 min in an Eppendorf 5415 microcentrifuge to remove the insoluble matter, and the supernatant was extracted with 0.5 volume of chloroform to ensure the removal of lipids. Samples were spun through a 0.45-μm-pore-size microcentrifuge spin filter before loading. Concentrations and ratios of the oxidized and reduced foul's of NAD and NADP were monitored by HPLC with fluorescence detection using an HP1100 LC with an Agilent 1100 fluorescence detector and a Supelco Supelcosil 5 μm C18 column (4.6- by 250-mm analytical column designed for efficient separation of nucleotides).

2. Results

Visual Identification of PHA Granules:

Direct observation of PHA granules with phase contrast light microscopy is commonly used as a viable screening method for PHA in bacteria (McCool et al., 1999). However, this method is not applicable to cyanobacteria due to the presence of thylakoid membranes as well as inclusions such as cyanophycin and polyphosphate. To enhance the visibility of PHA granules, cells were stained with the lipophilic oxazine dye Nile blue A. Nile pink, the oxazone form of the dye, is formed by the spontaneous oxidation of Nile blue A in aqueous solution. Traditionally, Nile blue staining includes a heat fixation of the cells onto the slide, which kills the cells, and staining with a relatively high concentration of dye (Ostle et al., 1982). However, in cyanobacteria, this treatment leads to high background fluorescence due to the presence of pigments. Instead, living cyanobacterial cells were stained by adding 0.04% (w/v; final concentration) Nile blue A in aqueous solution to 2 ml aliquots of cultures in early-exponential phase and the cultures were grown for an additional 12 hours before sampling. Control experiments indicated that up to 0.25% (w/v) of the dye did not affect the rate of cell growth or the maximum cell density (data not shown). The agar-embedded cells on the microscope slides could survive under these conditions for at least 3 to 4 hours without much reduction in the Nile blue/Nile red fluorescence yield.

Figure 9:
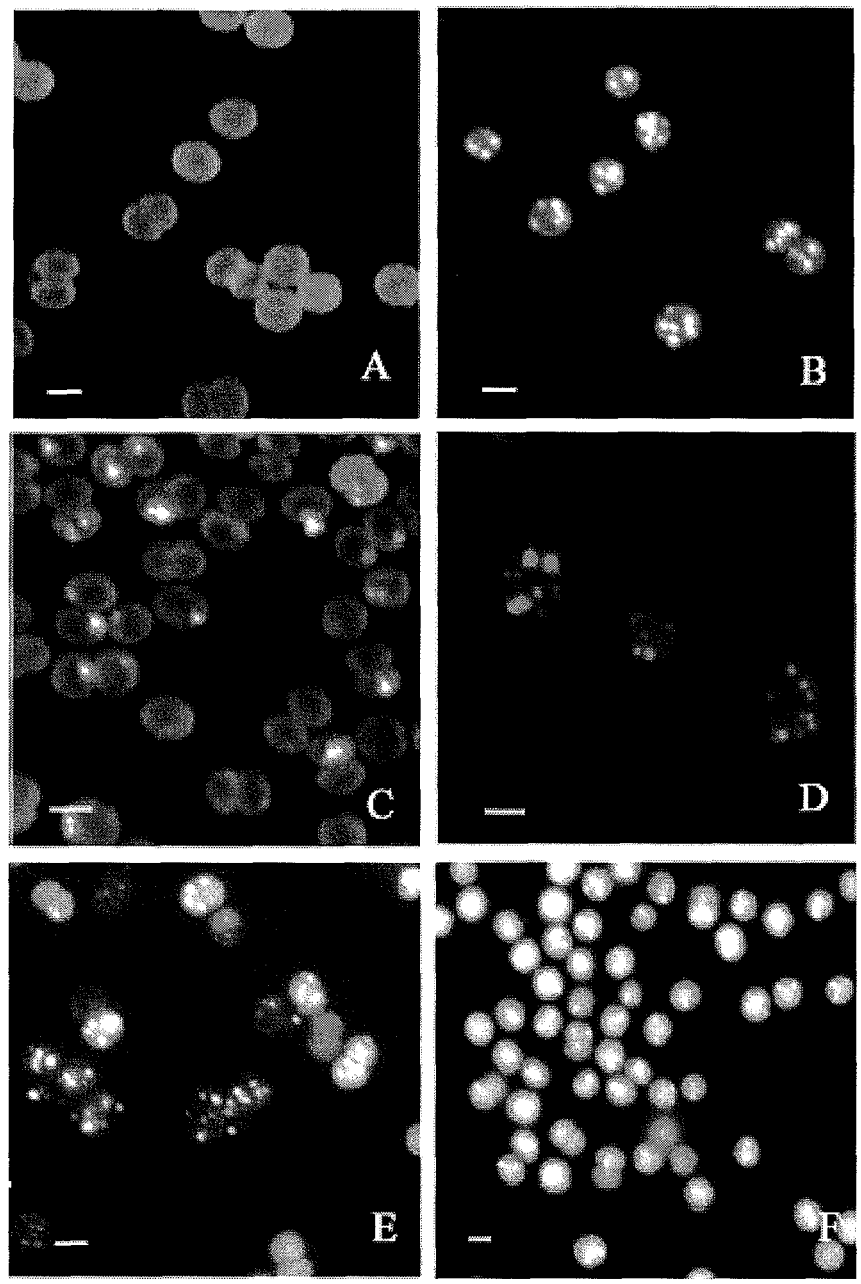
FIG. 9: *Synechocystis* sp. PCC 6803 cells after in vivo staining with 0.04% Nile blue (FIG. 9A) for 12 h. Images were obtained using a confocal laser scanning microscope with excitation at 488 nm and detection between 560 and 620 nm (FIGS. 9A-D) or using a epi-fluorescent light microscope (FIGS. 9E-F).

Upon excitation, PHA granules were visible as bright orange spots on the red auto-fluorescence background of *Synechocystis* cells (FIG. 9). Under nutrition-balanced conditions in normal BG-11 medium, few PHB granules were detected in cells of the wild type (FIG. 9A) or of the CyanoRubrum or NDH-2-less strains (not shown) until late in the stationary phase. However, multiple granules were observed in cells of the PS II-less/oxidase-less (FIG. 9D), oxidase-less (FIG. 9E) and NDH-1-less mutants (FIG. 9F), even during the exponential growth phase in BG-11 medium. After transfer to nitrogen-limited medium in which the nitrogen source was reduced to 10% of the original concentration, wild type started to accumulate PHA almost immediately and an average about 4 granules per cell can be seen in stationary phase (FIG. 9B). When a reduced nitrogen source such as ammonium chloride was supplied to the growth medium replacing nitrate, photoautotrophically grown wild type accumulated PHA during exponential growth (FIG. 9C). After replacement of nitrate by ammonium the culture grew at a normal rate and retained its normal appearance.

The results presented in the previous paragraph suggest that a reduced fixed-nitrogen source leads to accumulation of PHA, possibly because of a decreased demand for NADH/NADPH used for nitrate reduction. However, an alternate explanation would be that low nitrogen availability by itself leads to PHA accumulation: 16.7 mM nitrate was replaced by 10 mM ammonium as higher ammonium concentrations are toxic. To test this possibility, 0.5 mM (final concentration) of a specific inhibitor of glutamate synthase, DON, was added to an exponentially growing wild-type culture in BG-11 media. As nitrogen assimilation was blocked the color of the culture quickly changed from blue-green to yellow-brown, reflecting the degradation of phycobilin proteins. However, the number of PHA granules found in wild type in the presence and absence of DON was very similar at one or less per cell (data not shown). Therefore, a lack of nitrogen assimilation by itself does not lead to PHA accumulation.

Figure 10:
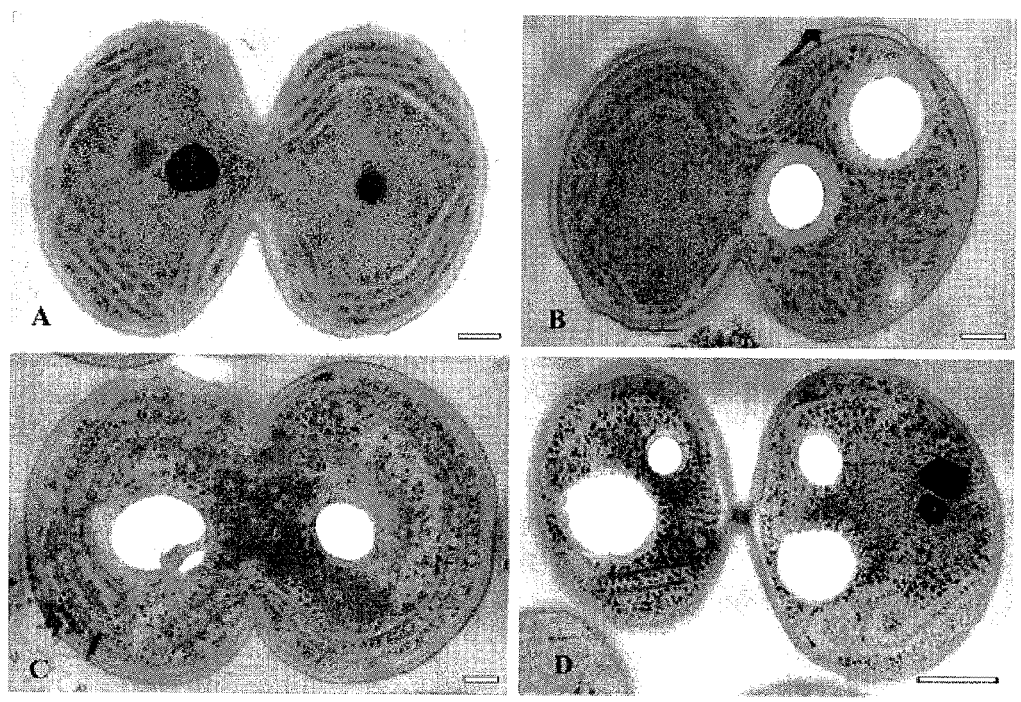
FIG. 10. Ultrastructure of *Synechocystis* sp. PCC 6803 strains in early exponential phase grown under photoautotrophic conditions, except for the PSII-less/oxidase-less strain that was grown photomixotrophically in the presence of 5 mM glucose.

Electron Microscopy:

In order to verify that the Nile blue A-stained fluorescent granules indeed correspond to inclusions resembling PHA granules, electron microscopy was performed on exponential-phase wild-type *Synechocystis* sp. PCC 6803 that was grown in standard BG-11 and that showed very few fluorescent granules, as well as on two other strains (the oxidase-less and the PS II-less/oxidase-less mutants) and on wild type after N-limitation (FIG. 10). In the latter three cases, increasing levels of Nile blue staining granules were observed. Indeed, the number of Nile blue A fluorescent granules correspond very well to the number of open spaces within the cell, taking into account that the thickness of slices for transmission electron microscopy (70 nm) is less than the projection of the fluorescence focal field along the z axis across the cell (600-800 nm). PHA granules generally are visible as electron-transparent inclusions upon electron microscopy (Ballard et al., 1987), possibly because PHA is washed out during sample preparation. A survey of multiple sections showed that in wild type grown under normal conditions only about 20% of the sectioned cells contained such granules and the number in each sectioned cell was no more than three (Table 7). However, in the PS II-less/oxidase-less mutant, the vast majority of sectioned cells contained at least one granule and the granule size was much larger (average 145 nm in diameter) compared to that in wild type grown under normal conditions (about 75 nm in diameter). Note that for granules with a diameter exceeding the thickness of the section, the granule diameter may be underestimated depending on how the granule was cut during sample preparation. In nitrogen-limited wild-type cells, the thylakoid structure was less organized (FIG. 10D) and the average number of granules per cell increased by an order of magnitude. As shown in FIGS. 10C and D, in *Synechocystis* the granules usually were not found to be associated with thylakoids or the cytoplasmic membrane, in contrast to the situation in *Synechococcus* MA19, where it is known that PHB granules are found to be very close to or surrounded by thylakoid membranes, or in a *Synechocystis* mutant deficient in glycogen biosynthesis, where occasionally granules were found to be closely associated with the cytoplasmic membrane.

TABLE 7

Average number and diameter of PHA granules found in electron microscopy thin (70 nm) sections of *Synechocystis* strains.

| Strain | Growth conditions | Number of granules[a] | Diameter (nm)[b] |
|---|---|---|---|
| wild type | BG-11 | 0.4 | 75 ± 26 |
| wild type | N-limited | 3.8 | 85 ± 21 |
| oxidase-less | BG-11 | 2.3 | 100 ± 34 |
| oxidase-less | N-limited | 3.1 | 95 ± 28 |
| PS II-less/oxidase-less | BG-11 + glucose | 1.5 | 145 ± 54 |
| Cyanorubrum | BG-11 | 1.7 | 105 ± 44 |
| NDH-1-less | BG-11 | 1.4 | 85 ± 32 |

[a] The survey was on a section through at least 50 cells; the number of granules represents the average number of granules per sectioned cell.
[b] The diameter of the granules was averaged over all granules counted in each strain.

Figure 11:
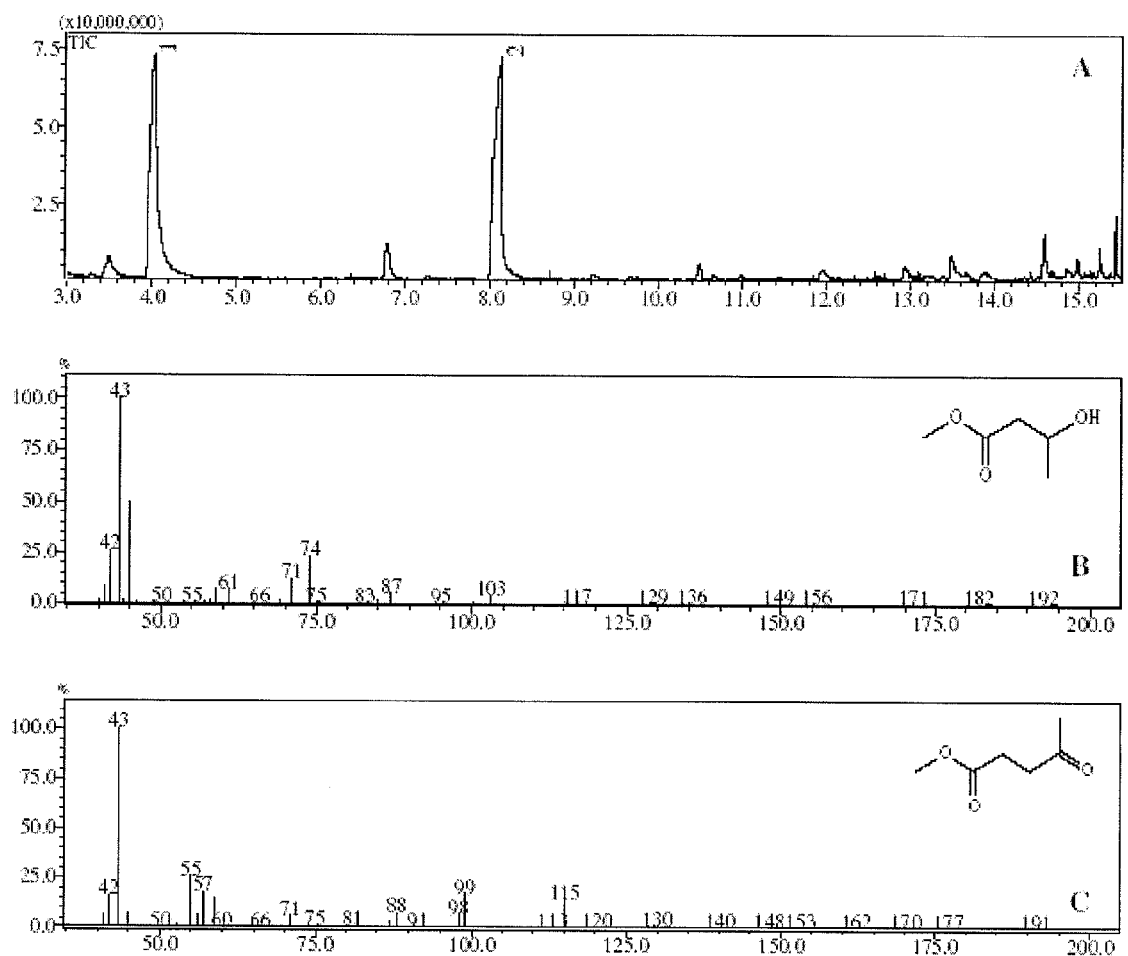
FIG. 11 Whole cell methanolysis product isolated from the PS II-less/oxidase-less strain grown under photomixotrophic conditions and analyzed by GC/MS (FIG. 11A). Two major peaks were detected. The GC/MS fingerprint of peaks 1 and 2 are presented in FIGS. 11B-C, respectively. The mass fragmentation pattern of peak 1 matches with that of 3-hydroxybutyrate methyl ester, the methanolyzed product of PHB (FIG. 11B), and the mass pattern of peak 2 suggested formation of a possible degradation product of glucose or glycogen, levulinic acid methyl ester, after extended methanolysis (FIG. 11C).

PHA can vary in its composition, and GC/MS was used to determine the chemical nature of these inclusions. To do so, cells were harvested at specific culture stages and dried by freeze drying followed by baking at 105° C. to remove residual water content. After breaking the cells, the material was subjected to methanolysis for 2.5 hours in chloroform. The mass pattern of one of the main methanolysis products (peak 1 in FIG. 11A) matched solely with the methyl ester of 3-hydroxybutyrate (FIG. 11B), whereas no evidence of hydroxyvalerate or other esters was obtained. The second main peak observed was identified as the methyl ester of levulinic acid (FIG. 11C), which was later verified as an artifact introduced by the presence of glucose or glycogen in dried cells (data not shown). These data indicate that the only PHA that *Synechocystis* sp. PCC 6803 is capable of producing is the PHB homopolyester.

PHB Content:

As shown in previous sections, the accumulation of PHB not only is determined by the genotype of the strains, but also is related to the stage or conditions of cell growth. The amount of PHB accumulation under different conditions and in different strains is listed in Table 8. The PHB content was determined by GC/MS after extraction and methanolysis of PHB from dried cells, using PHB purchased from Sigma as a standard. The PHB content (% of dry weight) was consistently lower than might be expected from fluorescence and electron microscopy visualization (FIGS. 9 and 10). This may be caused by incomplete PHB extraction and/or methanolysis. Therefore, the PHB content listed in Table 8 represent a lower limit for PHB quantity. However, the extraction efficiency is expected to be similar for all cells and conditions, and therefore the PHB content can be quantitatively compared between strains and conditions. Under normal growth conditions in medium with balanced nutrients, wild type as well as the NDH-2-less and the CyanoRubrum strains synthesized little PHB and had a PHB content of 0.3% or less. However, the oxidase-less mutant and the NDH-1-less mutant accumulated an order of magnitude more PHB under these conditions, and the PS II-less/oxidase-less mutant accumulated even twice the amount of PHB than the oxidase-less and NDH-1-less strains.

TABLE 8

PHB accumulation in *Synechocystis* sp. PCC 6803 and its mutants under various growth conditions. Cultures were grown for seven days under the conditions listed before the PHB content was analyzed. Results shown are the average of three independent experiments.

| | PHB content (% of cell dry weight) | | | | | |
|---|---|---|---|---|---|---|
| Culture conditions[a] | Wild type | Oxidase-less | PS II-less/oxidase-less[e] | NDH-1-less[f] | NDH-2-less | Cyano-Rubrum[f] |
| BG-11 | 0.1 ± 0.0 | 2.2 ± 0.5 | 3.8 ± 0.4 | 1.9 ± 0.8 | 0.3 ± 0.1 | 0.2 ± 0.1 |
| N-limited[b] | 2.8 ± 0.1 | 5.9 ± 0.3 | 6.5 ± 0.6 | 4.7 ± 0.7 | 2.3 ± 0.2 | 3.2 ± 0.2 |

TABLE 8-continued

PHB accumulation in *Synechocystis* sp. PCC 6803 and its mutants under various growth conditions. Cultures were grown for seven days under the conditions listed before the PHB content was analyzed. Results shown are the average of three independent experiments.

| | PHB content (% of cell dry weight) | | | | | |
|---|---|---|---|---|---|---|
| Culture conditions[a] | Wild type | Oxidase-less | PS II-less/oxidase-less[e] | NDH-1-less[f] | NDH-2-less | Cyano-Rubrum[f] |
| N-reduced[c] | 3.0 ± 0.5 | 3.8 ± 0.8 | 6.2 ± 0.7 | 4.6 ± 0.5 | 2.2 ± 0.2 | 2.8 ± 0.3 |
| Acetate[d] | 4.7 ± 0.6 | 3.2 ± 0.4 | 5.0 ± 0.4 | ND | ND | 1.2 ± 0.1 |

[a]Unless stated otherwise, cultures were grown photoautotrophically at 50 µmol photons $m^{-2}s^{-1}$ in BG-11 medium supplemented with 5 mM TES-NaOH (pH 8.0).
[b]Nitrate in BG-11 was reduced to 1.67 mM (10% of the original concentration).
[c]Nitrate in BG-11 was replaced by 10 mM $NH_4Cl$.
[d]BG-11 was supplemented with 10 mM sodium acetate.
[e]BG-11 was supplemented with 10 mM TES-NaOH (pH 8.0) buffer and 5 mM glucose.
[f]Bubbled with 2% $CO_2$ enriched air.
ND: Not determined.

Under nitrogen-limited conditions, all strains accumulated a high level of PHB: amounts were roughly comparable to those in the PS II-less/oxidase-less strain under normal conditions. Similar results were obtained when cells were provided with a reduced nitrogen source in the form of ammonia.

As PHB seemed to accumulate under conditions of reduced NADP and NAD(P)H is used for acetoacetyl-CoA reduction, PHB might be a fermentation product to regenerate NADP, and therefore PHB levels were determined in several strains upon growth under micro-aerobic conditions. PHB levels in these strains were similar to those in the controls grown under normal conditions (data not shown) and therefore, PHB does not appear to be a fermentation product in *Synechocystis*.

To determine whether metabolite levels near the start of the PHB pathway affected PHB synthesis, 10 mM Na-acetate was added to cultures. As shown in Table 8, wild-type cells accumulated as much as 4.7% PHB, suggesting that the level of acetate (or a derived metabolite) in the cell significantly influences PHB levels.

One additional factor to take into account is the growth rate of the cultures, as in batch culture a strain with a higher growth rate will produce more PHA than a slower growing strain, if the PHB content per cell is similar at the end of the exponential phase. The growth of the different strains under various conditions is compared in Table 9. Under control conditions all mutants except the oxidase-less strain grew slower than the wild type. Under nitrogen-limited conditions, all strains grew with a doubling time of 16-21 hours. In the presence of acetate or ammonium, strains grew essentially at the same rate as in standard BG-11. Therefore, the large differences in PHB accumulation in the various mutants and under various conditions cannot be explained simply by differences in growth rates.

TABLE 9

Doubling times of wild type and mutants of *Synechocystis* sp. PCC 6803 grown under various culture conditions. Data shown are the average of at least three independent determinations.

| | Doubling time (h) | | | | | |
|---|---|---|---|---|---|---|
| Culture conditions[a] | WT | Oxidase-less | PS II-less/oxidase-less[e] | NDH-1-less[f] | NDH-2-less | Cyano-rubrum[f] |
| BG-11 | 10.3 ± 1.8 | 11.0 ± 2.5 | 19.5 ± 2.3 | 17.2 ± 3.1 | 15.4 ± 2.1 | 16.8 ± 3.2 |
| N-limited[b] | 19.0 ± 2.5 | 21.4 ± 1.2 | 21.0 ± 1.3 | 21.2 ± 2.4 | 15.8 ± 2.0 | 18.0 ± 1.7 |
| N-reduced[c] | 10.6 ± 2.1 | 15.1 ± 1.7 | 16.1 ± 2.1 | 16.5 ± 1.5 | 13.2 ± 3.3 | 19.1 ± 2.9 |
| Acetate[d] | 12.2 ± 2.6 | 11.1 ± 1.9 | 20.2 ± 1.8 | 16.4 ± 2.2 | 18.3 ± 1.7 | 21.4 ± 1.2 |

[a]Unless stated otherwise, cultures were grown photoautotrophically at 50 µmol photons m-2s-1 in BG-11 medium supplemented with 5 mM TES-NaOH (pH 8.0).
[b]Nitrate in BG-11 was reduced to 1.67 mM (10% of the original concentration).
[c]Nitrate in BG-11 was replaced by 10 mM NH4Cl.
[d]BG-11 was supplemented with 10 mM sodium acetate.
[e]BG-11 was supplemented with 10 mM TES-NaOH (pH 8.0) buffer and 5 mM glucose.
[f]Bubbled with 2% $CO_2$ enriched air.
ND: Not determined.

Redox Cofactor Levels:

The results thus far seem to indicate that PHB accumulation occurs under specific conditions, including in the presence of added acetate. One other possible factor that is important for PHB synthesis is the NADPH level in the cell, as NADPH is used for PHB synthesis and as a high NADP reduction level appears to inhibit isocitrate dehydrogenase in the TCA cycle (Cooley et al., 2000) and therefore may lead to a high acetate level. To determine the relationship between PHB accumulation and the redox state of the cell, the levels of the reduced/oxidized nicotinamide nucleotides were measured and compared as an indication of the redox state of cytoplasm. The NADPH/NADP and NADH/NAD levels were determined using two independent methods, by spectrophotometric detection at 340 nm after specific treatments and by HPLC with fluorescence detection. The spectrophotometric method is fast but may not be fully specific, while the HPLC method is slower (thus allowing more time for artifactual interactions) but more specific. The two resulting sets of data were comparable with less than 20% difference (data not shown); therefore, only the HPLC data are presented here (Table 10). For these determinations, all cultures were harvested at mid-exponential phase and extracted within 30 minutes before further experiments.

ratio did not change much in the presence of ammonia or with a limiting amount of nitrate, but in the three strains tested under these conditions, the NADPH/NADP(total) ratio increased 5 to 6-fold in wild type, to levels comparable to the high reduction levels in the oxidase-less and the PS II-less/oxidase-less mutants (Table 10).

Comparing the results reported in Table 4 with the PHB content data listed in Table 2, it is clear that a high NADPH/NADP(total) ratio in all cases was correlated with a high PHB content in *Synechocystis* sp. PCC 6803. No such correlation was apparent for the NADH/NAD(total) ratio and PHB accumulation.

TABLE 10

Steady-state pyridine nucleotide levels and ratio of reduced/total cofactors in various strains in exponential phase growing in BG-11 and under nitrogen-limited and reduced-nitrogen (NH$_4$Cl) conditions (concentrations in μM/OD$_{730}$).

| Culture conditions$^a$ | Cofactor | WT | Oxidase less | PS II-less/ oxidase-less$^f$ | NDH-1-less$^g$ | NDH-2-less | Cyano- Rubrum$^g$ |
|---|---|---|---|---|---|---|---|
| BG-11 | NAD + NADH | 0.06 ± 0.02 | 0.08 ± 0.03 | 0.15 ± 0.04 | 0.03 ± 0.02 | 0.07 ± 0.02 | 0.13 ± 0.03 |
| | NADP + NADPH | 0.26 ± 0.03 | 0.12 ± 0.08 | 0.76 ± 0.07 | 0.07 ± 0.02 | 0.32 ± 0.07 | 0.31 ± 0.05 |
| | NADH/(NAD + NADH) | 0.56 ± 0.21 | 0.38 ± 0.13 | 0.69 ± 0.11 | 0.55 ± 0.24 | FR | 0.68 ± 0.18 |
| | NADPH/(NADP + NADPH) | 0.12 ± 0.05 | 0.41 ± 0.17 | 0.71 ± 0.23 | FR | 0.07 ± 0.05 | 0.16 ± 0.06 |
| N-limited$^b$ | NAD + NADH | 0.04 ± 0.02 | 0.06 ± 0.02 | 0.23 ± 0.05 | ND | ND | ND |
| (1.67 mM) | NADP + NADPH | 0.21 ± 0.03 | 0.38 ± 0.04 | 0.72 ± 0.24 | ND | ND | ND |
| | NADH/(NAD + NADH) | 0.33 ± 0.12 | 0.36 ± 0.13 | 0.75 ± 0.18 | ND | ND | ND |
| | NADPH/(NADP + NADPH) | 0.71 ± 0.30 | 0.62 ± 0.25 | 0.88 ± 0.31 | ND | ND | ND |
| N-reduced$^c$ | NAD + NADH | 0.09 ± 0.03 | 0.17 ± 0.05 | 0.26 ± 0.12 | ND | ND | ND |
| | NADP + NADPH | 0.32 ± 0.06 | 0.54 ± 0.10 | 1.15 ± 0.55 | ND | ND | ND |
| | NADH/(NAD + NADH) | 0.44 ± 0.18 | 0.29 ± 0.12 | 0.66 ± 0.17 | ND | ND | ND |
| | NADPH/(NADP + NADPH) | 0.63 ± 0.19 | 0.75 ± 0.24 | 0.83 ± 0.25 | ND | ND | ND |

$^a$Unless stated otherwise, cultures were grown photoautotrophically at 50 μmol photons m$^{-2}$s$^{-1}$ in BG-11 medium supplemented with 5 mM TES-NaOH (pH 8.0).
$^b$Nitrate in BG-11 was limited to 1.67 mM (10% of the original concentration).
$^c$Nitrate in BG-11 was replaced by 10 mM NH$_4$Cl.
$^d$BG-11 was supplemented with 10 mM sodium acetate.
$^e$BG-11 was supplemented with 10 mM TES-NaOH (pH 8.0) buffer and 5 mM glucose.
$^f$Bubbled with 2% CO$_2$ enriched air.
FR: Fully reduced.
ND: Not determined.

The total amount of NAD(H) and NADP(H) among different *Synechocystis* sp. PCC 6803 strains varied up to about ten-fold. However, for each strain the NAD(H) and NADP(H) amounts varied only up to three to four-fold when growing in different media (Table 10). Whereas the NAD(H) level in all strains was relatively low, and the standard deviation in the data was correspondingly large, the NADP pool size was larger and varied up to 10-fold between different strains (Table 10). Consistent with earlier observations (Cooley et al., 2001), the NAD and NADP reduction states depended greatly on the strains. NAD was fully reduced in the NDH-2-less strain and between 35 and 70% of NAD was reduced in the other strains. The NDH-1-less mutant had a virtually fully reduced NADP(H) pool whereas NADP was 40-70% reduced in the oxidase-less mutants. In contrast, the NADP pool was rather oxidized in the wild type, CyanoRubrum, and the NDH-2-less mutant. The latter parameter (NADP reduction state) therefore seems to correlate with levels of PHB accumulation.

To probe a possible correlation between the NADP reduction state and the amount of PHB accumulation further, the NADP and NAD levels and reduction states were determined in the wild type, as well as in the oxidase-less and the PS II-less/oxidase-less mutants, as a function of fixed-nitrogen limitation and presence of a reduced nitrogen source (ammonia). When cultured in BG-11 medium with limiting nitrate levels or in the presence of ammonia, the NADH/NAD(total)

REFERENCES

The following references, to the extent that they provide exemplary procedural or other details supplementary to those set forth herein, are specifically incorporated herein by reference.

U.S. Pat. No. 4,413,058
U.S. Pat. No. 4,242,455
U.S. Pat. No. 4,350,765
U.S. Pat. No. 4,458,066
U.S. Pat. No. 4,683,202
U.S. Pat. No. 5,220,007
U.S. Pat. No. 5,221,605
U.S. Pat. No. 5,238,808
U.S. Pat. No. 5,284,760
U.S. Pat. No. 5,322,783
U.S. Pat. No. 5,354,670
U.S. Pat. No. 5,366,878
U.S. Pat. No. 5,380,721
U.S. Pat. No. 5,384,253
U.S. Pat. No. 5,389,514
U.S. Pat. No. 5,538,877
U.S. Pat. No. 5,538,880
U.S. Pat. No. 5,550,318
U.S. Pat. No. 5,563,055
U.S. Pat. No. 5,580,859
U.S. Pat. No. 5,589,466

U.S. Pat. No. 5,610,042
U.S. Pat. No. 5,635,377
U.S. Pat. No. 5,656,610
U.S. Pat. No. 5,702,932
U.S. Pat. No. 5,736,524
U.S. Pat. No. 5,780,448
U.S. Pat. No. 5,789,166
U.S. Pat. No. 5,789,215
U.S. Pat. No. 5,798,208
U.S. Pat. No. 5,830,650
U.S. Pat. No. 6,945,100
U.S. Pat. No. 5,981,274
U.S. Pat. No. 5,994,624
U.S. Publication 2002/0042111
U.S. Publication 2002/0072109
Aichi et al., *J. Bacteriol.*, 183:5840-5847, 2001.
Allen, *Ann. Rev. Microbiol.*, 38:1-25, 1984.
Amichay et al., *Mol. Gen. Genetics*, 235:247-252, 1992.
Anderson and Dawes, *Microbiol. Rev.*, 54:450-472, 1990.
Aresta et al., *Environ. Chem. LTRS.*, 3(3):136-139, 2005.
Asada et al., *Int. J. Biol. Macromol.*, 25:37-42, 1999.
Asato and Ginoza, *Nat. New Biol.*, 244(135):132-133, 1973.
Ausubel et al., In: *Current Protocols in Molecular Biology*, John, Wiley & Sons, Inc, NY, 1994.
Ballard et al., In: *Recent Advances in Mechanistic and Synthetic Aspects of Polymerization*, Fontanille and Guyot (Eds.), 215:293-314, Reidel (Kluwer) Publishing Co., Lancaster, U.K, 1987.
Barringer et al., *Gene*, 89:117, 1990.
Beaucage et al., *Tetra. Lett.*, 22: 1859-1862, 1981.
Berger and Kimmel, In: *Guide to Molecular Cloning Techniques*, Methods in Enzymology, 152, Academic Press, Inc., San Diego, Calif.
Bergmeyer, *Z. Klin. Chem. Klin. Biochem.*, 13:507-508, 1975.
Blackburn et al., *J. Lipid. Res.*, 32(12):1911-1918, 1991.
Boocock et al., *J. Am. Oil Chemists Soc.* 75:1167-1172, 1998.
Boothman et al., *Cancer Res.*, 49(11):2871-2878, 1989.
Brock in Biotechnology: A Textbook of Industrial Microbiology, Second Edition (1989) Sinauer Associates, Inc., Sunderland, Mass., or Deshpande, Mukund V., Appl. Biochem. Biotechnol., 36, 227, (1992).
Borek, *Carcinog. Compr. Surv.*, 10:303-316, 1985.
Brown et al., *Meth. Enzymol.*, 68:109-151, 1979.
Bryant et al., *Nature*, 279(5716):795-796, 1979.
Burks et al., *Proc. Natl. Acad. Sci. USA*, 94(2):412-417, 1997.
Burton and Barbas, *Adv. Immunol.*, 57:191-280, 1994.
Cadwell and Joyce, *PCR Methods Appl.*, 2(1):28-33, 1992.
Campbell et al., *J. Bacteriol.*, 149:361-363, 1982.
Carbonelli et al., *FEMS Microbiol. Lett.*, 177(1):75-82, 1999.
Carr, *Biochim. Biophys. Acta*, 120:308-310, 1966.
Chandler et al., *Proc. Natl. Acad. Sci. USA*, 94(8):3596-601, 1997.
Chen and Okayama, *Mol. Cell. Biol.*, 7(8):2745-2752, 1987.
Cisneros et al., *J. Chrom. B-Anal. Tech. Biomed. Life Sci.*, 807(1):105-110, 2004.
Cocea, *Biotechniques*, 23(5):814-816, 1997.
Cooley and Vermaas, *J. Bacteriol.*, 183:4251-4258, 2001.
Cooley et al., *J. Bacteriol.*, 182:714-722, 2000.
Cooley et al., *Science*, 239(4844):1121-1128, 1988.
Cunningham and Wells, *Science*, 244(4908):1081-1085, 1989.
Dahlqvist et al., *Proc. Natl. Acad. Sci. USA*, 2000; 97:6487-92.
Dawes and Senior, *Adv. Microb. Physiol.*, 10:135-266, 1973.
De Philippis et al., *FEMS Microbiol. Rev.*, 103:187-194, 1992.
De Philippis et al., *J. Gen. Microbiol.*, 138:1623-1628, 1992.
Deutscher, In: *Methods in Enzymology*, Vol. 182, Academic Press, Inc. NY, 1990.
Edwards and Gantt, *J. Cell Biol.*, 50(3):896-900, 1971.
Fechheimer, et al., *Proc Natl. Acad. Sci. USA*, 84:8463-8467, 1987.
Fraley et al., *Proc. Natl. Acad. Sci. USA*, 76:3348-3352, 1979.
Gantt and Conti, *J. Bacteriol.*, 97(3):1486-1493, 1969.
Goeddel, In: *Gene Expression Technology: Meth. in Enzymol.*, 185, Academic Press, San Diego, Calif., 1990
Gopal, *Mol. Cell. Biol.*, 5:1188-1190, 1985.
Graham and Van Der Eb, *Virology*, 52:456-467, 1973.
Grigorieva and Shestakov, FEMS Microbiol. LETT., 13:367-370, 1982.
Guatelli et al., *Proc. Natl. Acad. Sci. USA*, 87:1874, 1990.
Hall et al., *Radiat. Res.*, 114(3):415-424 1988.
Harland and Weintraub, *J. Cell Biol.*, 101(3):1094-1099, 1985.
He et al., *Europ. J. Biochem.*, 263(2):561-570, 1999.
Hein et al., *Arch. Microbiol.*, 170:162-170, 1998.
Herrero et al., *J. Bacteriol.*, 145:175-180, 1981.
Hilton et al., *J. Biol. Chem.*, 271(9):4699-4708, 1996.
Howitt and Vermaas, *Biochemistry*, 37:17944-17951, 1998.
Howitt et al., *J. Bacteriol.*, 181:3994-4003, 1999.
Howitt et al., *Planta*, 214:46-56, 2001.
Innis, et al., In: *PCR Protocols. A Guide to Methods and Application*, Academic Press, Inc. San Diego, 1990.
Inouye and Inouye, *Nucleic Acids Res.*, 13:3101-3109, 1985.
Jensen and Sicko, *J. Bacteriol.*, 106(2):683-686, 1971.
Jordan and Ogren, *Nature*, 291:513-515, 1981.
Journal of NIH Research, 3:81-94, 1991.
Kaneda et al., *Science*, 243:375-378, 1989.
Kaneko et al., *DNA Res.* 3(3):109-136, 1996.
Kato et al, *J. Biol. Chem.*, 266:3361-3364, 1991.
Klaidman et al., *Anal. Biochem.*, 228:312-317, 1995.
Koksharova et al., *Plant Mol. Biol.*, 36:183-194, 1998.
Koncz et al., *EMBO J.*, 9(5):1337-1346, 1990.
Kwoh et al., *Proc. Natl. Acad. Sci. USA*, 86:1173, 1989.
Lagarde et al., *Appl. Environ. Microb.*, 66(1):64-72, 2000.
Lama et al., *Phytochemistry*, 42:655-659, 1996.
Lambert and Borek, *J. Natl. Cancer Inst.*, 80(18):1492-1497, 1988.
Lemoigne, *Bull. Soc. Chim. Biol.*, 8:770-782, 1926.
Levenson et al., *Hum. Gene Ther.*, 9(8):1233-1236, 1998.
Li and Golden, *Proc. Natl. Acad. Sci. USA*, 90:11673-11682, 1993.
Liebergesell et al., *Eur. J. Biochem.*, 226:71-80, 1994.
Lomell et al., *J. Clin. Chem.*, 35:1826, 1989.
Landegren et al., *Science*, 241:1077-1080, 1988.
Van Brunt, *Biotechnology*, 8:291-294, 1990. needs alphabetized
Manchak and Page, *Microbiol.*, 140:953-963, 1994.
Maniatis, et al., Molecular Cloning, A Laboratory Manual, Cold Spring Harbor Press, Cold Spring Harbor, N.Y., 1989.
Marks et al., *J. Mol. Biol.* 222: 581-597, 1991.
Marland et al., In: *Global, Regional, and National $CO_2$ Emissions. In Trends: A Compendium of Data on Global Change*, 2006.
McCann et al., *Proc. Natl. Acad. Sci. USA*, 72(3):979-983, 1975.
McCool and Cannon, *J. Bacteriol.*, 181:585-592, 1999.
McGinn et al., *Plant Physiology*, 132(1):218-229, 2003.
Mérida et al., *J. Bacteriol.*, 173:4095-4100, 1991.
Miyake et al., *Appl. Biochem. Biotech.*, 84:991-1002, 2000.
Miyake et al., *J. Ferment. Bioeng.*, 82:516-518, 1996.
Mohamed et al., *J. Bacteriol.*, 187:6883-6892, 2005.
Nabel et al., *Science*, 244(4910):1342-1344, 1989.

Nakamura et al. *DNA Res.*, 9(4):123-130, 2002.
Nandi et al., *Crit. Rev. Microbiology*, 24(1):61-84, 1998.
Narang et al., *Meth. Enzymol.*, 68:90-99, 1979.
Nicolau and Sene, *Biochim. Biophys. Acta*, 721:185-190, 1982.
Nicolau et al., *Methods Enzymol.*, 149:157-176, 1987.
Nobre et al., *Europ. Food Res. Technology*, 223(6):787-790, 2006.
Oelkers et al., *J. Biol. Chem.* 2000; 275:15609-12.
Ogawa, *Proc. Natl. Acad. Sci. USA*, 88:4275-4279, 1991.
Oppenheimer et al., *Cell*, 67(3):483-493, 1991.
Ostle and Holt, *Appl. Environ. Microbiol.*, 44:238-241, 1982.
PCT Appln. WO 94/09699
PCT Appln. WO 95/06128
PCT Appln. WO/88/09379
Potter et al., *Proc. Natl. Acad. Sci. USA*, 81:7161-7165, 1984.
Prince et al., *Crit. Rev. Microbiology*, 31(1):19-31, 2005.
Reusch, Can. *J. Microbiol.*, 41:50-54, 1995.
Rippka et al., *J. Gen. Micro.*, 111:1-61, 1979.
Rippe, et al., *Mol. Cell. Biol.*, 10:689-695, 1990.
Ris and Singh, *J. Biophys. Biochem. Cytol.*, 9:63-80, 1961.
Rito-Palomares, *J. Chrom. B-Anal. Tech. Biomed. Life Sci.*, 807(1):3-11, 2004.
Roberts and Koths, *Cell*, 9(4 Pt 1):551-557, 1976.
Rubio et al., *Plant Mol. Biol.*, 30:845-850, 1996.
Saka et al., *J. Scient. Indust. Res.*, 65(5):420-425, 2006.
Sambrook et al., In: *DNA microaarays: a molecular cloning manual*, Cold Spring Harbor Laboratory Press, Cold Spring Harbor, N.Y., 1989; 2001.
Schmidt et al., *Science*, 238(4829):960-963, 1987.
Scopes, In: *Protein Purification*, Springer-Verlag, NY; 1982.
Serrano-Carreon et al., *Appl. Microb. Biotech.*, 58(2):170-174, 2002.
Shi et al., *J. Biosci. Bioeng.*, 87:666-677, 1999.
Smith, *Ann. Microbiol.*, 134B:93-113, 1983.
Sommer et al. *EMBO J.*, 9(3):605-613, 1990.
Stal, *FEMS Micro. Rev.*, 103:169-180, 1992.
Stanier and Cohen-Bazire, *Annu. Rev. Microbiol.*, 31:225-274, 1977.
Steinbüchel and Füchtenbusch, *Trends Biotechnol.*, 16:419-427, 1998.
Steinbüchel and Valentin, *FEMS Microbiol. Lett.*, 128:219-228, 1995.
Steinbüchel, In: *Biomaterials*, 123-213, Byrom (Ed), Macmillan, London, 1991.
Sudesh et al., *Int. J. Biol. Macromol.*, 30:97-104, 2002.
Takahashi et al., *Biotech. Lett.*, 20:183-186, 1998.
Taroncher et al., *Appl. Environ. Microbiology*, 66(10):4440-4448, 2000.
Taroncher-Oldenberg et al., *Appl. Environ. Microbiol.*, 66:4440-4448, 2000.
Tasaka et al., *EMBO J.*, 15(23):6416-6425, 1996.
Topal et al., *J. Agric. Food Chem.*, 54(15):5604-5610, 2006.
Tur-Kaspa et al., *Mol. Cell. Biol.*, 6:716-718, 1986.
Van de Meene et al., *Arch Microbiol.*, 184(5):259-270, 2006.
Vincenzini et al., *J. Bacteriol.*, 172:2791-2792, 1990.
Vinnemeier et al., *FEMS Microb. LTRS*, 169(2):323-330, 1998.
Warren et al., *Biochemistry*, 35(27):8855-8862, 1996.
Waeltermann et al., *Mol. Microbiol.* 2005; 55:750-63.
Waeltermann et al., *Microbiol.* 2000; 146:1143-9.
White, In: *The Physiology and Biochemistry of Prokaryotes*, Oxford University Press, Inc. New York, 2000.
Williams, *Methods Enzymol.*, 167:766-768, 1988.
Wilson et al., *Science*, 244:1344-1346, 1989.
Witte et al., *Cancer Res.*, 49(18):5066-5072, 1989.
Wong et al., *Gene*, 10:87-94, 1980.
Wu and Wallace, *Gene*, 4:560, 1989.
Wu and Wu, *Biochemistry*, 27: 887-892, 1988.
Wu and Wu, *J. Biol. Chem.*, 262:4429-4432, 1987.
Wu et al., *Bioresour. Technol.*, 76:85-90, 2001.
Wu et al., *Enzyme Microb. Technol.*, 30:710-715, 2002
Yagi, *Biochim. Biophys. Acta*, 1364:125-133, 1998.
Yelton et al., *J. Immunol.*, 155(4):1994-2004, 1995.
Zeng et al., *Biochemistry*, 35(40):13157-13164, 1996.
Zhang et al., *J. Biolog. Chem.*, 269(7):5036-5042, 1994.
Zhang, *Anal. Biochem.*, 285:163-167, 2000.
Zhou et al., *Biotech. LTRS*, 27(23-24):1891-1896, 2005.
Zou et al., *Plant J.* 1999; 19:645-53.

---

The invention claimed is:

1. A purified genetically engineered *Synechocystis* sp. PCC 6803 cyanobacterium, wherein the engineered cyanobacterium has been transformed with a plasmid vector comprising a first nucleotide sequence encoding acetyl-CoA carboxylase A (accA) (sll0728), acetyl-CoA carboxylase B (accB) (slr0435), acetyl-CoA carboxylase C (accC) (slr0053), and acetyl-CoA carboxylase D (accD) (sll0336), and a second nucleotide sequence encoding vesicle-inducing protein in plastids 1 (VIPP1) (sll0617) constitutively linked to a psbA3 promoter, wherein the first nucleotide sequence replaces the endogenous psbA2 gene of the said host genome and the second nucleotide sequence replaces the endogenous psbA3 gene of the said host genome wherein the plasmid is designed for insertion into *Synechocystis* genome psbA2 locus and wherein the purified genetically engineered *Synechocystis* sp. PPC 6803 cyanobacterium has an increased expression of *Synechocystis* sp. PCC 6803 acetyl-CoA (ACC) and an increased production of fatty acids or lipids as compared to a native *Synechocystis* sp. PCC 6803 cyanobacterium, and wherein the increased production in fatty acids or lipids content is at least 47% of the said purified genetically engineered *Synechocystis* sp. PPC 6803 cyanobacterium's dry weight.

2. The purified genetically engineered *Synechocystis* cyanobacterium of claim 1, wherein the increased production of fatty acids or lipids are produced by subjecting the bacterium to light.

3. The purified genetically engineered *Synechocystis* cyanobacterium of claim 1, wherein expression of one or more additional genes are altered with the genetic transformation, the additional gene being selected from the group consisting of a pspA gene, a yidC/oxal homologue, a plastoglobulin gene, a transacetylase gene, a desaturase gene, a PEP carboxylase gene, a citrate synthase gene, a fatty acid biosynthesis gene, a protease gene, a gene involved in cyanophycin biosynthesis or degradation, a phosphatidic acid phosphatase gene, and an acyltransferase gene.

4. The purified genetically engineered *Synechocystis* cyanobacterium of claim 1, wherein expression of one or more additional genes are altered with the genetic transformation, the additional gene being selected from the group consisting of sll1568, sll1848, slr2060, sll0617, slr1471, sll1463, slr0228, slr1024, slr1390, slr1604, slr0156, slr1641, slr0542, slr0165, slr2023, slr1511, sll1069, slr1332, slr0886, sll1605, slr1051, slr1176, slr1188, slr1024, sll1568, slr1829, slr1830, slr2001, slr2002, slr1350, sll1441, sll0541, sll0262, sll0920, sll0401, sll0534, sll0545, slr0348, sll1556, slr1254, slr0940, slr1293, sll0254 and sll1468 genes, and their homologues.

5. The purified genetically engineered *Synechocystis* cyanobacterium of claim 1, wherein at least one of the genes encoding all subunits of *Synechocystis* sp. PCC 6803 heterohexamer ACC is operably linked to a cyanobacteria-derived constitutive promoter or a cyanobacteria-derived inducible promoter.

6. A purified genetically engineered *Synechocystis* sp. PCC 6803 cyanobacterium transformed with a plasmid comprising a nucleotide sequence encoding acetyl-CoA carboxylase A (accA) (sll0728), acetyl-CoA carboxylase B (accB) (slr0435), acetyl-CoA carboxylase C (accC) (slr0053), and acetyl-CoA carboxylase D (accD) (sll0336), and a nucleotide sequence encoding vesicle-inducing protein in plastids 1 (VIPP1) (sll0617), the purified genetically engineered *Synechocystis* sp. PCC 6803 cyanobacterium being produced by a method comprising:
  transforming *Synechocystis* sp. PCC 6803 cyanobacterium with a first plasmid comprising a nucleotide sequence encoding accA (sll0728), accB (slr0435), accC (slr0053), and accD (sll0336), wherein the first plasmid is designed for insertion into *Synechocystis* genome psbA2 locus; and
  further transforming the transformed *Synechocystis* sp. PCC 6803 cyanobacterium with a second plasmid comprising a nucleotide sequence encoding VIPP1 (sll0617) constitutively linked to a psbA3 promoter;
wherein the purified genetically engineered *Synechocystis* sp. PPC 6803 cyanobacterium has an increased expression of *Synechocystis* sp. PCC 6803 acetyl-CoA (ACC) and an increased production of fatty acids or lipids as compared to a native *Synechocystis* sp. PCC 6803 cyanobacterium, and wherein the increased production in fatty acids or lipids content is at least 47% of the said purified genetically engineered *Synechocystis* sp. PPC 6803 cyanobacterium's dry weight.

* * * * *

SEQUENCE LISTING

```
<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: Synthetic Primer

<400> SEQUENCE: 1
gaggataagt aagtcatgag attatttgac                                      30

<210> SEQ ID NO 2
<211> LENGTH: 35
<212> TYPE: DNA
<213> ORGANISM: Artificial Sequence
<220> FEATURE:
<223> OTHER INFORMATION: Synthetic Primer

<400> SEQUENCE: 2
ctggctgagt taatgcattt acagattatt taacc                                35

<210> SEQ ID NO 3
```

-continued

```
<211> LENGTH: 25
<212> TYPE: DNA
<213> ORGANISM: Artificial Sequence
<220> FEATURE:
<223> OTHER INFORMATION: Synthetic Primer

<400> SEQUENCE: 3
gacaaataca taaggaatta taacc                                             25

<210> SEQ ID NO 4
<211> LENGTH: 21
<212> TYPE: DNA
<213> ORGANISM: Artificial Sequence
<220> FEATURE:
<223> OTHER INFORMATION: Synthetic Primer

<400> SEQUENCE: 4
gccaaaacag ccaagcttgg c                                                 21
```